United States Patent
Tonks et al.

(10) Patent No.: US 12,178,825 B2
(45) Date of Patent: Dec. 31, 2024

(54) METHOD AND COMPOSITIONS FOR FORMING A COPPER-CONTAINING COMPLEX AND USES THEREOF

(71) Applicants: COLD SPRING HARBOR LABORATORY, Cold Spring Harbor, NY (US); DEPYMED, INC., Farmingdalge, NY (US)

(72) Inventors: Nicholas Tonks, Cold Spring Harbor, NY (US); Navasona Krishnan, Hawthorn Woods, IL (US); Andreas Grill, Farmingdale, NY (US); Howard Sard, Woburn, MA (US)

(73) Assignees: Cold Spring Harbor Laboratory, Cold Spring Harbor, NY (US); Depymed, Inc., Farmingdale, NY (US)

( * ) Notice: Subject to any disclaimer, the term of this patent is extended or adjusted under 35 U.S.C. 154(b) by 262 days.

(21) Appl. No.: 17/866,724

(22) Filed: Jul. 18, 2022

(65) Prior Publication Data

US 2022/0370479 A1    Nov. 24, 2022

Related U.S. Application Data

(62) Division of application No. 16/761,631, filed as application No. PCT/US2018/059450 on Nov. 6, 2018, now Pat. No. 11,406,647.

(60) Provisional application No. 62/582,045, filed on Nov. 6, 2017.

(51) Int. Cl.
  *A61K 31/58*   (2006.01)
  *A61K 31/4184*   (2006.01)

(52) U.S. Cl.
  CPC .......... *A61K 31/58* (2013.01); *A61K 31/4184* (2013.01)

(58) Field of Classification Search
  None
  See application file for complete search history.

(56) References Cited

U.S. PATENT DOCUMENTS

| | | |
|---|---|---|
| 9,365,608 B2 | 6/2016 | McLane et al. |
| 9,546,194 B2 | 1/2017 | McLane et al. |
| 2010/0099726 A1 | 4/2010 | Cantley et al. |
| 2015/0099727 A1 | 4/2015 | McLane et al. |
| 2020/0376006 A1 | 12/2020 | Tonks et al. |

FOREIGN PATENT DOCUMENTS

| | | |
|---|---|---|
| WO | 2009033293 A1 | 3/2009 |
| WO | 201358970 A2 | 10/2013 |
| WO | 2015154897 A1 | 10/2015 |

OTHER PUBLICATIONS

Liao et al. "Protein Tyrosine Phosphatase 1B Expression Contributes to the Development of Breast Cancer". Journal of Zhejiang University—Science B (Biomedicine & Biotechnology). Apr. 2017; 18(4):334-342. (Year: 2017).*
Bollu et al. "Molecular Pathways: Targeting Protein Tyrosine Phosphatases in Cancer". Clin Cancer Res. May 1, 2017; 23(9):2136-2142. (Year: 2017).*
Gao et al. "Targeting Inhibition of Extracellular Signal-Regulated Kinase Kinase Pathway with AZD6244 (ARRY-142886) Suppresses Growth and Angiogenesis of Gastric Cancer". Scientific Reports. 2015; 5: Article No. 16382. (Year: 2015).*
Wu Xialei et al: "Ferulic acid alleviates lipopolysaccharide-induced acute lung injury through inhibiting TLR4/NF-[kappa]B signaling pathway", Journal of Biochemical and Molecular Toxicology,vol. 35, No. 3, Nov. 2, 2020.
Wu Jianzhi et al.: "Ferulic Acid Ameliorates Hepatic Inflammation and Fibrotic Liver Injury by Inhibiting PTP1 B Activity and Subsequent Promoting AMPK Phosphorylation", Frontiers in Pharmacology,vol. 12, Sep. 8, 2021.
Smith Ashley M. et al: "The protein tyrosine phosphatase 1 B inhibitor MSI-1436 stimulates regeneration of heart and multiple other tissues",NPJ Regenerative Medicine, vol. 2, No. 1, Mar. 3, 2017.
He Rong-Jun et al: "Protein tyrosine phosphatases as potential therapeutic targets",ACTA Pharmacologica Sinica, vol. 35, No. 10, Sep. 15, 2014 (Sep. 15, 2014), pp. 1227-1246.
International Search Report and Written Opinion of the International Searching Authority for International Application No. PCT/US2018/059450 mailed on Jan. 16, 2019.
Balavenkatraman, K.K., et al., "Epithelial Protein-Tyrosine Phosphatase 1B (PTP1B) Contributes to the Induction of Mammary Tumors by HER2/Neu but is not Essential for Tumor Maintenance", Mol. Cancer Res., vol. 9, No. 10, pp. 1377-1384 (2011).

(Continued)

*Primary Examiner* — Leslie A. Royds Draper
(74) *Attorney, Agent, or Firm* — Heslin Rothenberg Farley & Mesiti P.C.

(57) ABSTRACT

Provided is a method of forming a copper-containing complex, including contacting a sample containing copper with a compound of Formula I:

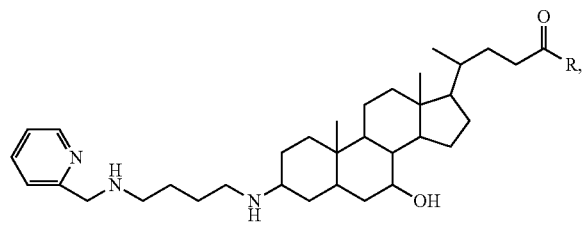

wherein R is —OH or —O—CH₃. Also provided is a method of inhibiting enzymatic activity of a kinase in a sample, including contacting the sample with a compound of Formula I. Further provided is a method of administering to a subject a pharmaceutical composition including a compound of Formula I optionally complexed with copper. Also provided is a pharmaceutical composition including copper complexed with a compound of Formula I.

8 Claims, 35 Drawing Sheets

(56) References Cited

OTHER PUBLICATIONS

Barr, A.J., et al., "Protein tyrosine phosphatases as drug targets: strategies and challenges of inhibitor development", Future Med. Chem., vol. 2, No. 10, pp. 1563-1576 (2010).
Bentires-Alj, M., et al., "Protein-Tyrosine Phosphatase 1B Is Required for HER2/Neu-Induced Breast Cancer", Cancer Res, vol. 67, No. 6, pp. 2420-2424 (2007).
Bollu, L.R., et al., "Molecular Pathways: Targeting Protein Tyrosine Phosphatases in Cancer", Clinical Cancer Res, vol. 23, No. 9, pp. 2136-2142 (2017).
Brady, D.C., et al., "Copper is required for oncogenic BRAF signaling and tumorigenesis", Nature, vol. 509, No. 7501, pp. 2-25 (2014).
Carboni, E., et al., "Insights on the interaction of alpha-synuclein and metals in the pathphysiology of Parkinson's disease", Metallomics, vol. 7, pp. 395-404 (2015).
Cooper, G.J.S., "Therapeutic Potential of Copper Chelation with Triethylenetetramine in Managing Diabetes Mellitus and Alzheimer's Disease", Springer Link, pp. 1-65 (2017).
Hoekstra, E., et al., "Meeting Report Europhosphatase 2015: Phosphatases as Drug Targets in Cancer", American Association of Cancer Research, vol. 76, pp. 193-196 (2016).
Hoekstra, E., et al., "Increased PTP1B expression and phosphatase activity in colorectal cancer results in a more invasive phenotype and worse patient outcome", Oncotarget, vol. 7, No. 16, pp. 21922-21938 (2016).
Julien, S.G., et al., "Protein tyrosine phosphatase 1B deficiency or inhibition delays ErbB2-induced mammary tumorigenesis and protects from lung metastasis", Nature Genetics, vol. 39, abstract only (2007).
Krishnan, N., "Abstract LB-022: PTP1B directed therapeutics for HER2 positive breast cancer", Cancer Research, vol. 77, Issue 13 Supplement (2017).
Krishnan, N., et al., "Targeting the disordered C-terminus of PTP1B with an allosteric inhibitor", Nat Chem Biol. vol. 10, No. 7, pp. 558-566 (2014).
Krishnan, N., et al., "DPM-1001 decreased copper levels and ameliorated deficits in a mouse model of Wilson's disease", Genes & Development, vol. 32, pp. 944-952 (2018).
Krishnan, N., et al., "A potent, selective, and orally bioavailable inhibitor of the protein-tyrosine phosphatase PTP1B improves insulin and leptin signaling in animal models", J. Biol. Chem., vol. 293, No. 5, pp. 1517-1525 (2018).
Lavaud, P., et al., "Strategies to overcome trastuzumab resistance in HER2-overexpressing breast cancers: focus on new data from clinical trials", BMC Medicine, vol. 12, No. 132, pp. 1-10 (2014).
Lessard, L., et al., "PTP1B Is an Androgen Receptor-Regulated Phosphatase That Promotes the Progression of Prostate Cancer", American Association for Cancer Research, vol. 72, No. 6, pp. 1530-1537 (2012).
Liu, H., et al., "PTP1B promotes cell proliferation and metastasis through activating src and ERK1/2 in non-small cell lung cancer", Cancer Letters, vol. 359, No. 2, abstract only (2015).
Moasser, M.M., et al., "Abstract ES2-1: Mechanisms of HER2 signaling, targeting, and resistance", Cancer Research (2015).
Nunes-Xavier, C.E., et al., "Protein tyrosine phosphatases as novel targets in breast cancer therapy", Biochimica et Biophysica Acta, vol. 1836, pp. 211-226 (2013).
Soysal, S., et al., "PTP1B expression is an independent positive prognostic factor in human breast cancer", Breast Cancer Research and Treatment vol. 137, Issue 2, pp. 637-644 (2013).
Tonks, N.K., et al., "A Brake Becomes an Accelerator: PTP1B-A New Therapeutic Target for Breast Cancer", Cancer Cell, vol. 11, pp. 214-216 (2007).
MSI-1436C—CMC Information [Trodusquemine HCI] IND Update, IND # 75, 164 & 100,889 (references for Investigator IND), Date: Jul. 21, 2015.
Turski, M.L., et al., "New Roles for Copper Metabolism in Cell Proliferation, Signaling, and Disease", The Journal of Biological Chemistry, vol. 284, No. 2, pp. 717-721 (2009).
Wang, J., et al., "Suppression of PTP1B in gastric cancer cells in vitro induces a change in the genome-wide expression profile and inhibits gastric cancer cell growth", Cell Biol Int., vol. 34, No. 7, pp. 747-753 (2010).
Filomeni, G., et al. "The isatin-Schiff base copper(II) complex Cu(isaepy)2 acts as delocalized lipophilic cation, yields widespread mitochondrial oxidative damage and induced AMP-activated protein kinase-dependent apoptosis," Carcinogenesis, vol. 30, No. 7, pp. 1115-1124 (2009).
Anderegg, G., et al., "Pyridine derivatives as complexing agents X thermodynamics of complex formation of N,N'-bis-(2-piridylmethyl)-ethylenediamine and of two higher homologues," J. Coord. Chem., vol. 4, pp. 267-275 (1975).
Supplementary European Search Report dated Jun. 24, 2021, and Written Opinion in connection with European Patent Application No. EP18873054.
Tanaka, A., et al., "Role of Copper Ion in the Pathogenesis of Type 2 Diabetes," Endocr. J., vol. 56, No. 5, pp. 699-706 (2009).
Wang, Q., et al., "Potent Inhibition of Protein Tyrosine Phosphatase 1 B by Copper Complexes: Implications for Copper Toxicity in Biological Systems," Chemm Commun, vol. 46, No. 20, pp. 3547-3549 (2010).

\* cited by examiner

METHOD AND COMPOSITIONS FOR FORMING A COPPER-CONTAINING COMPLEX AND USES THEREOF

CROSS REFERENCE TO RELATED APPLICATIONS

This application is a divisional of U.S. patent application Ser. No. 16/761,631, filed on May 5, 2020, as a national stage filing under 35 U.S.C. § 371 of International Application No. PCT/US2018/059450, filed on Nov. 6, 2018, and claims priority to U.S. provisional patent application No. 62/582,045, filed Nov. 6, 2017. The entire contents of the said applications are incorporated herein by reference in their entireties.

GOVERNMENT RIGHTS STATEMENT

This invention was made with Government support under grant numbers CA053840 and GM055989 awarded by the National Institutes of Health. The Government has certain rights in the invention.

FIELD OF THE INVENTION

The subject matter disclosed herein relates to compounds for complexing with copper ions, and compounds complexed with copper ions, and uses thereof. More particularly, disclosed are 3-(substituted amino)-7-hydroxy-cholanic acid derivatives that form a complex with copper, and their uses as copper chelators, inhibitors of enzymatic activity, and treatment of disease.

BACKGROUND OF THE INVENTION

The aberrant regulation of signal transduction pathways, and the accompanying disruption of the normal patterns of protein phosphorylation, has been implicated in the etiology of a variety of major human diseases, including diabetes, obesity, and cancer. The ability to target such signaling pathways selectively holds enormous therapeutic potential. In the last decade protein kinases have emerged as a major class of druggable targets. In particular, several drugs directed against protein kinases have had a considerable impact on the treatment of various cancers. Nevertheless, the focus on kinases for drug development has encountered several challenges, including intrinsic and acquired resistance to such therapies. Consequently, additional targets and approaches are required. In this context, it is important to remember that protein phosphorylation is a reversible process, in which the coordinated and competing activities of kinases and phosphatases are important for determining signaling outcome. The protein tyrosine phosphatases (PTPs), which represent a large family of proteins that work in coordination with kinases to control cell signaling, have also been implicated in the etiology of several human diseases. Nevertheless, PTPs remain underexploited as therapeutic targets. Of particular importance is the development of treatments for diabetes, obesity, and cancer by targeting the activity of phosphatases and kinases.

Furthermore, copper has been implicated in the regulation of signal transduction through control of the activity of kinases such as MEK, linking copper to the control of cell growth, and its disruption in tumorigenesis and metastasis Physiological levels of copper are under complex homeostatic control, including transporters that control influx and efflux, together with specialized chaperones that deliver the metal to its sites of action. Disruption of these homeostatic mechanisms is associated with a variety of disease states. Mutations in ATP7B, which functions in copper excretion, lead to accumulation of the metal resulting in Wilson's disease, a severe autosomal recessive disorder. The physical burden of the disease is felt in the liver, in particular, as this tissue expresses high levels of ATP7B. It begins with a presymptomatic period, during which copper accumulates in the liver. A variety of hepatic problems are encountered from enlargement of the liver, to hepatitis and cirrhosis, and even acute liver failure. As the disease progresses it results in the development of neuropsychiatric symptoms, including speech and cognitive impairment, particular tremors and dystonia, as well as ataxia and Parkinsonism. In addition, psychiatric problems including personality changes, antisocial behavior, anxiety and depression appear in Wilson's patients at some time during the course of the disease. Current treatment strategies depend on chelators that act as "de-coppering" agents, the goal of which is to decrease the level of the metal and to try and re-establish normal homeostasis. Unfortunately, penicillamine and trientine, which are the pharmacological agents that are used most frequently, are associated with severe adverse effects. Consequently, new potent and specific copper-chelators are needed for the treatment of Wilson's disease.

The present disclosure is directed to overcoming these and other deficiencies in the art.

SUMMARY OF THE INVENTION

In an aspect, disclosed is a method of forming a copper-containing complex, including contacting a sample containing copper with a compound of Formula I:

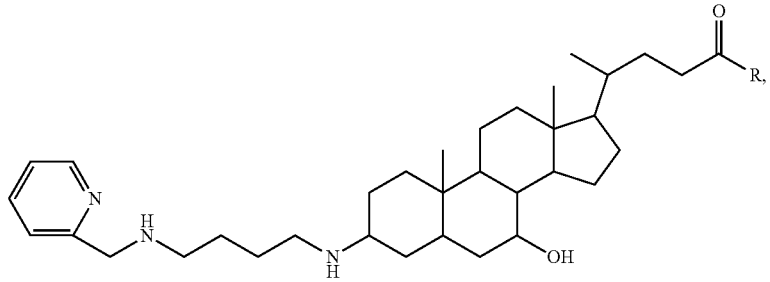

wherein R is —OH or —O—CH$_3$. In some embodiments, the sample containing copper is an abiotic solution or suspension. In other embodiments, the sample containing copper is a biological solution, suspension, tissue or organism. For example, contacting a sample may include administering said compound to a subject. In another example, administering said compound reduces a cytotoxic effect of copper. In yet another example, the subject is a human diagnosed with a disorder that is associated with elevated physiological levels of copper. In an example, the disorder is Wilson's disease. Another embodiment includes inhibiting the catalytic activity of an enzyme by forming the copper-containing complex, and the enzyme is selected from pyruvate kinase M (PKM), mitochondrial adenylate kinase 2 (AK2), creatine kinase B (CKB), p21-activated kinase (PAK), TP53-regulating kinase (TP53RK), phosphoglycerate kinase 1 (PGK1), pyridoxal kinase (PDXK), mitochondrial creatine kinase U-type (CKMT1B), mitogen-activated protein kinase kinase (MEK), tyrosine kinase CSK, protein tyrosine phosphatase 1B (PTP1B), and any combination of two or more of the foregoing.

In another aspect, disclosed is a method of inhibiting enzymatic activity of a kinase in a sample, including contacting the sample with a compound of Formula I.

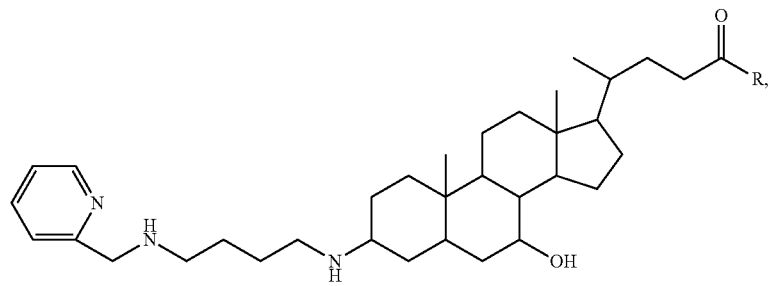

wherein R is —OH or —O—CH$_3$, and wherein the kinase is selected from pyruvate kinase M (PKM), mitochondrial adenylate kinase 2 (AK2), creatine kinase B (CKB), p21-activated kinase (PAK), TP53-regulating kinase (TP53RK), phosphoglycerate kinase 1 (PGK1), pyridoxal kinase (PDXK), mitochondrial creatine kinase U-type (CKMT1B), mitogen-activated protein kinase kinase (MEK), tyrosine kinase CSK, and any combination of two or more of the foregoing. In an embodiment, the sample includes a subject in need of medical treatment and contacting the sample includes administering said compound to the subject. In an example, the subject has gastric cancer. In another example, the subject has a HER2-negative breast cancer. For example, the HER2-negative cancer may be estrogen-receptor negative cancer, progesterone-receptor negative cancer, or triple-negative breast cancer. In a further example, the subject has triple-negative breast cancer. Other examples include administering to the subject AZD6244. In an example, administration to the subject of said compound and AZD6244 has a therapeutic effect and the therapeutic effect is greater than a therapeutic effect caused by administration to the subject of said compound without AZD6244 and a therapeutic effect of administration to the subject of AZD6244 without said compound. For example, the therapeutic effect may include an inhibition of tumor growth, an inhibition of cancer cell metastasis, a stimulation of cancer cell death, or any combination of two or more of the foregoing. In yet further examples, the compound is administered to a subject in need of medical treatment who was previously administered AZD6244. For example, contacting the sample with the compound may include an inhibition of tumor growth, an inhibition of cancer cell metastasis, a stimulation of cancer cell death, or any combination of two or more of the foregoing.

In yet another aspect, disclosed is a method of administering to a subject a pharmaceutical composition including copper complexed with a compound of Formula I:

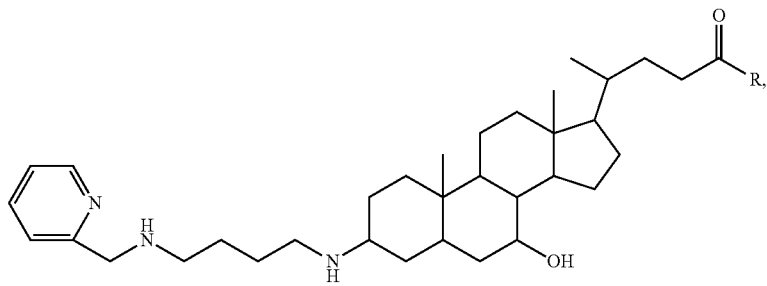

wherein R is —OH or —O—CH$_3$. In an embodiment, administering the pharmaceutical composition includes reducing the subject's Body Mass Index. In another embodiment, administering the pharmaceutical composition includes enhancing a physiological response to one or more hormones and the one or more hormones are insulin, leptin, or both. In yet another embodiment, the subject has cancer and the cancer is gastric cancer or HER2-negative breast cancer, and administering the pharmaceutical composition comprises inhibiting tumor growth, inhibiting cancer cell metastasis, stimulating cancer cell death, or any combination of two or more of the foregoing. In some examples, the cancer may be HER2-negative breast cancer wherein the HER2-negative breast cancer is estrogen-receptor negative, progesterone-receptor negative, or triple-negative breast cancer. Some embodiments further include administering to said subject AZD6244. In some examples, wherein administration to the subject of said compound and AZD6244 has a therapeutic effect and the therapeutic effect is greater than a therapeutic effect caused by administration to the subject of said compound without AZD6244 and a therapeutic effect of administration to the subject of AZD6244 without said compound. For example, the therapeutic effect may include an inhibition of tumor growth, an inhibition of cancer cell metastasis, a stimulation of cancer cell death, or any combination of two or more of the foregoing. In yet further examples, the pharmaceutical composition is administered to a subject in need of medical treatment who was previously administered AZD6244. In still other examples, administering the pharmaceutical composition includes inhibition of tumor growth, inhibition of cancer cell metastasis, stimulation of cancer cell death, or any combination of two or more of the foregoing. In another embodiment, administering the compound comprises inhibiting activity of protein tyrosine phosphatase 1B (PTP1B) in the subject.

In another aspect, disclosed is a pharmaceutical composition including copper complexed with a compound of Formula I:

FIG. 2 shows the effects of increasing concentration of DPM-1001 (squares) and MSI-1436 (triangles) tested against the PTP1B double mutant S372P/L192A PTP1B.

FIG. 3 shows PTP activity of PTP1B$_{1-405}$ (circles) or PTP1B$_{1-321}$ (squares) (100 nM) incubated with DPM-1001 (1 μM) for 15 min. The complex was diluted 100-fold and the activity was monitored for 240 minutes. The results were compared with assays conducted with MSI-1436 against PTP1B$_{1-405}$ (circles) or PTP1B$_{1-321}$ (squares), represented in grey.

FIG. 4 shows time-dependence of the inhibition of the long (black bars) and short (grey bars) forms of PTP1B by DPM-1001.

FIG. 5 shows the elution profile of PTP1B$_{1-394}$ in the absence (circles) and presence (triangles) of DPM-1001.

FIG. 6 shows time dependence in the Inhibition of PTP1B$_{1-405}$ by DPM-1001 in the absence (open bars) or presence of H$_2$O$_2$-degrading enzymes catalase (grey bars) and peroxiredoxin (black bars).

FIG. 7 shows DPM-1001 (1 mM) reacted with CuSO4 (8 mM) and the reaction mixture analyzed by ESI-MS. Isotopic pattern analysis of the peak at 727.5 m/z is shown in the inset.

FIGS. 8A and 8B show a proposed structure of a complex [Cu(Formula I)SO$_4$)].

FIG. 9 shows radiolabelled copper ($^{64}$Cu) at increasing concentrations titrated against DPM-1001.

FIG. 10 shows effects of increasing concentration of Cu-DPM-1001 complex on WT PTP1B (circles), H320A/H331A PTP1B$_{1-405}$ (squares) and H320A/H331A/S372P PTP1B$_{1-405}$ (triangles).

FIG. 11 shows increasing concentrations of $^{64}$Cu-DPM-1001 complex titrated against PTP1B$_{1-405}$, PTP1B$_{1-321}$ and H320A/H331A mutant PTP1B.

FIG. 12. shows increasing concentrations of $^{64}$Cu-DPM-1001 complex titrated against a panel of PTPs (PTP1B$_{1-405}$ (circles), PTP1B$_{1-321}$ (squares), TCPTP (diamonds), SHP2

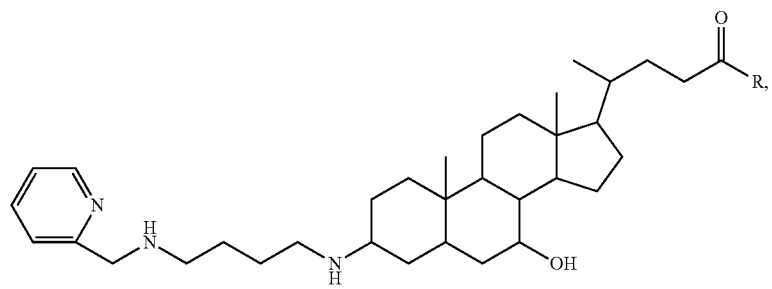

wherein R is —OH or —O—CH$_3$. In an embodiment, the composition includes a pharmaceutically acceptable excipient.

BRIEF DESCRIPTION OF THE DRAWINGS

These and other features, aspects, and advantages of the present disclosure will become better understood when the following detailed description is read with reference to the accompanying drawings, wherein.

(open circles), LAR (open squares), PTPalpha (upward triangle), PTPsigma (downward triangle), and PTEN (open diamonds)).

Figure 13:
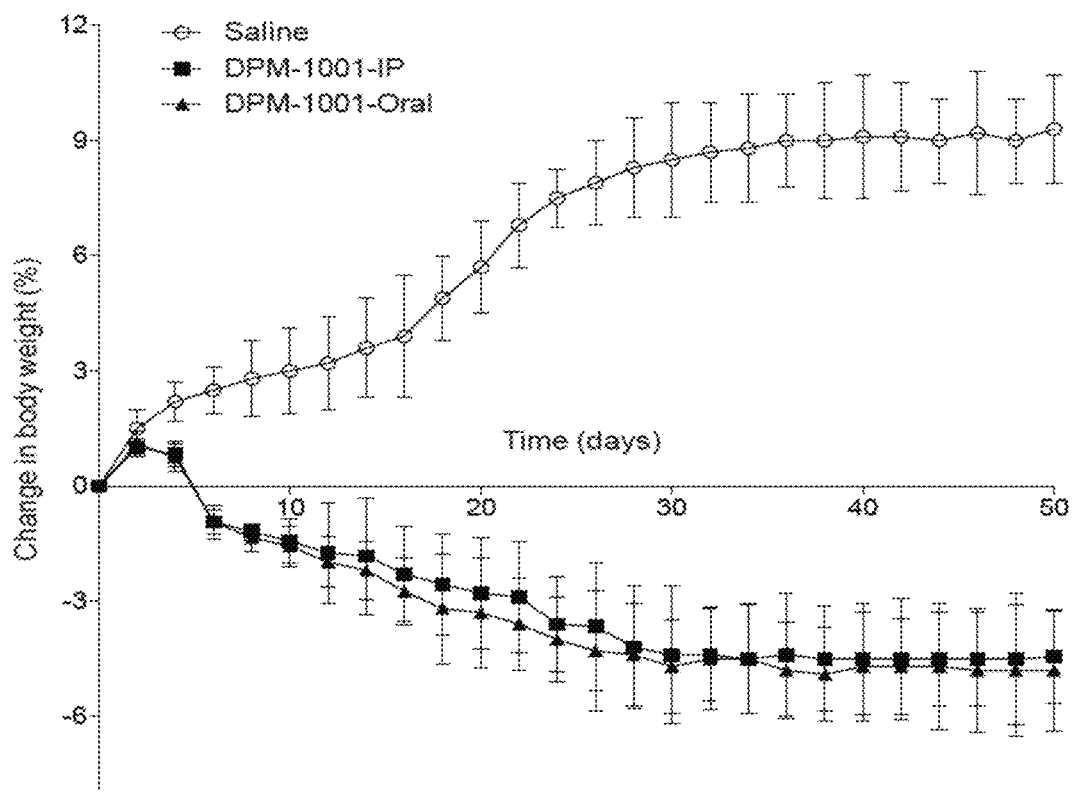

FIG. 13 shows effects of DPM-1001 on body weight. Beginning at 10 weeks of age, until the study was terminated (18 weeks of age) high-fat diet (HFD)-fed obese male mice (C57bl6/J) were treated daily with DPM-1001 (5 mg/kg, either orally or intraperitoneally) and body weight was compared to saline-treated obese mice (n=10 in each group).

Figure 14:
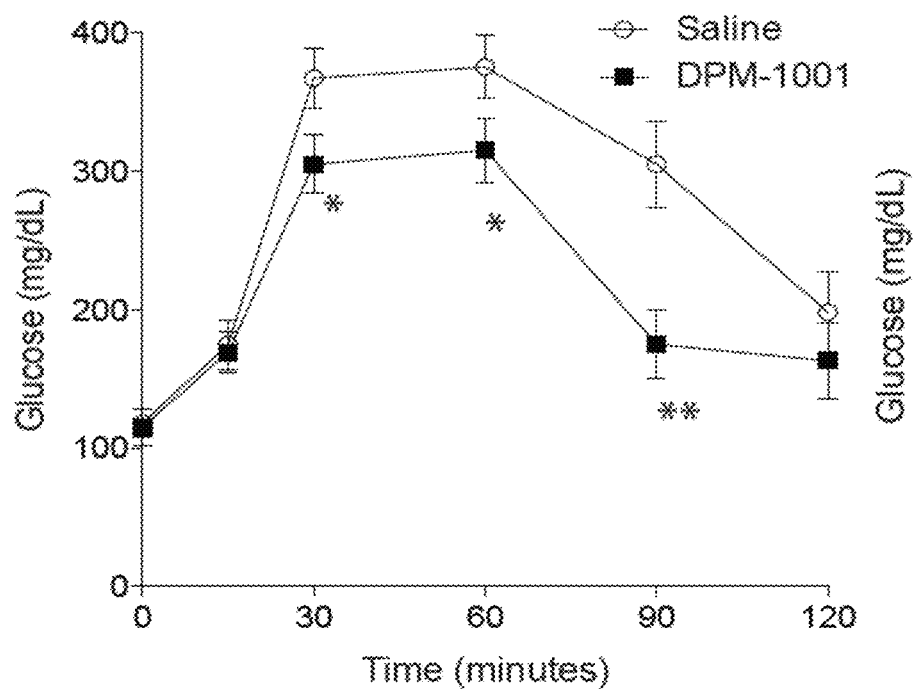

FIG. 14 shows effects of HFD-fed 14-week-old male mice treated with saline or DPM-1001, administered D-glucose (2 mg/g body weight), and blood glucose was monitored (in each group, n=10). Statistical analysis was performed using 2-way ANOVA (*p<0.05, **p<0.01).

Figure 15:
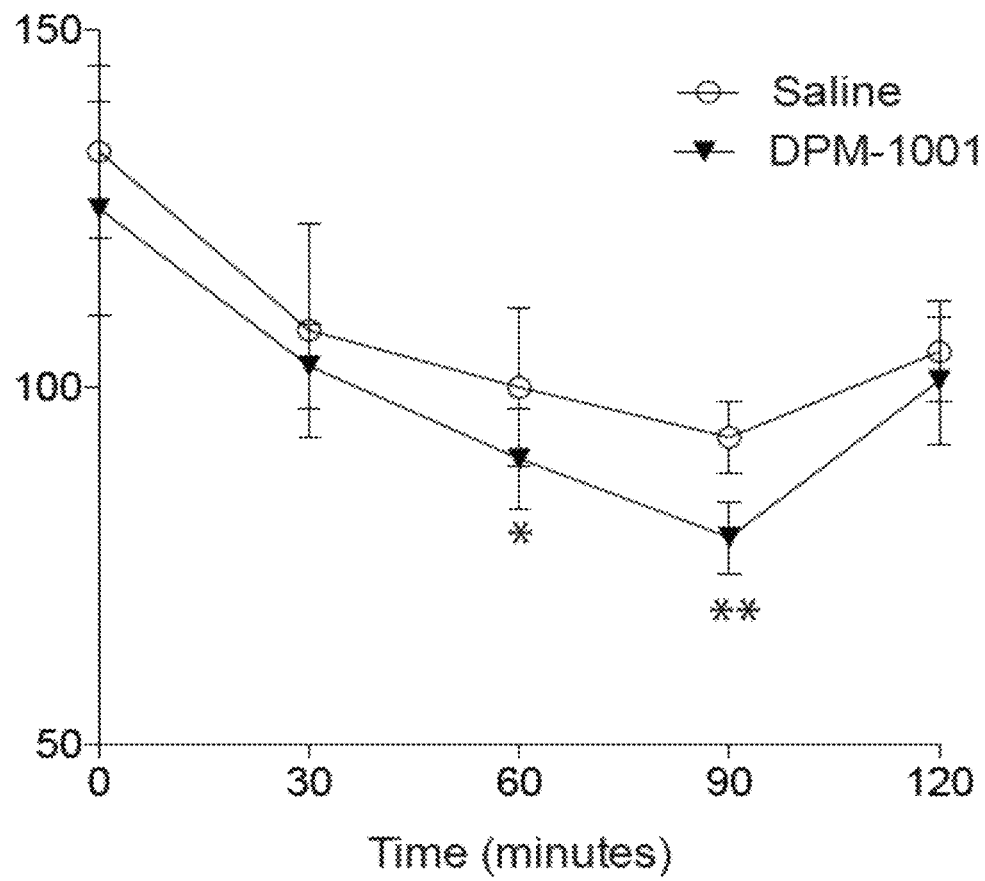

FIG. 15 shows effects on blood glucose of HFD-fed 14-week-old male mice treated with saline or DPM-1001, administered insulin (0.75 mU/g body weight) (in each group, n=10). Statistical analysis was performed using 2-way ANOVA ($*p<0.05$).

Figure 16:
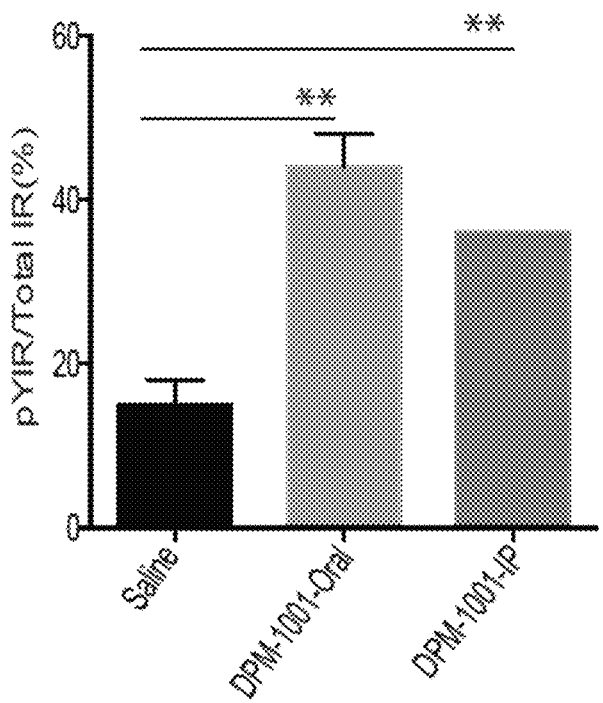

FIG. 16 shows insulin-induced tyrosine phosphorylation of IR-β from 14-week-old mice treated with saline or DPM-1001, either orally or intraperitoneally (TP). For insulin stimulation, animals were treated with insulin (0.75 mU/g, IP) for 15 minutes. Mean±s.e.m. Statistical analysis was performed using 2-way ANOVA ($**p<0.01$).

Figure 17:
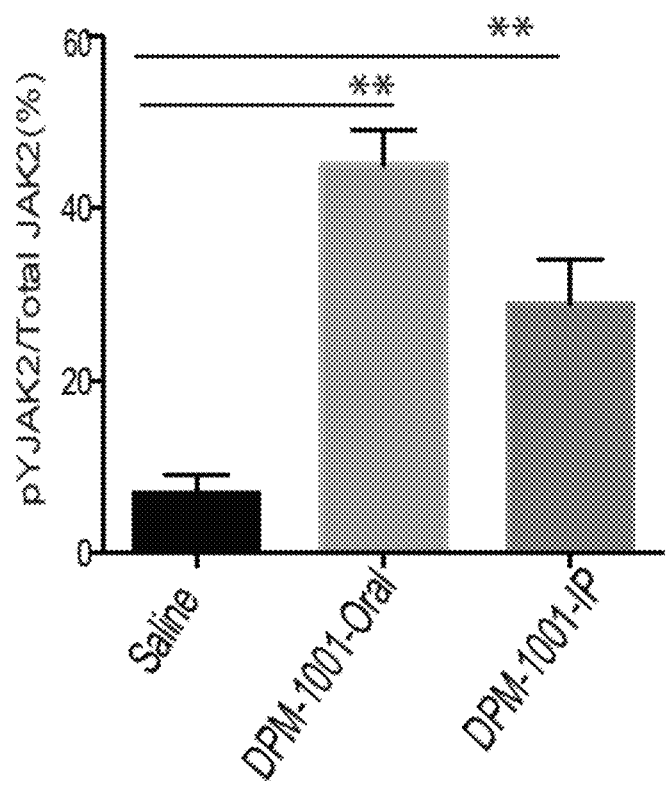

FIG. 17 shows leptin-induced tyrosine phosphorylation of JAK2 in hypothalamus tissue lysates from 14-week-old mice treated with saline, or DPM-1001, either orally or intraperitoneally (IP). For leptin stimulation, animals were treated with leptin (1 mg/kg, sc) for 15 minutes. Mean±s.e.m. Statistical analysis was performed using 2-way ANOVA ($**p<0.01$).

Figure 18:
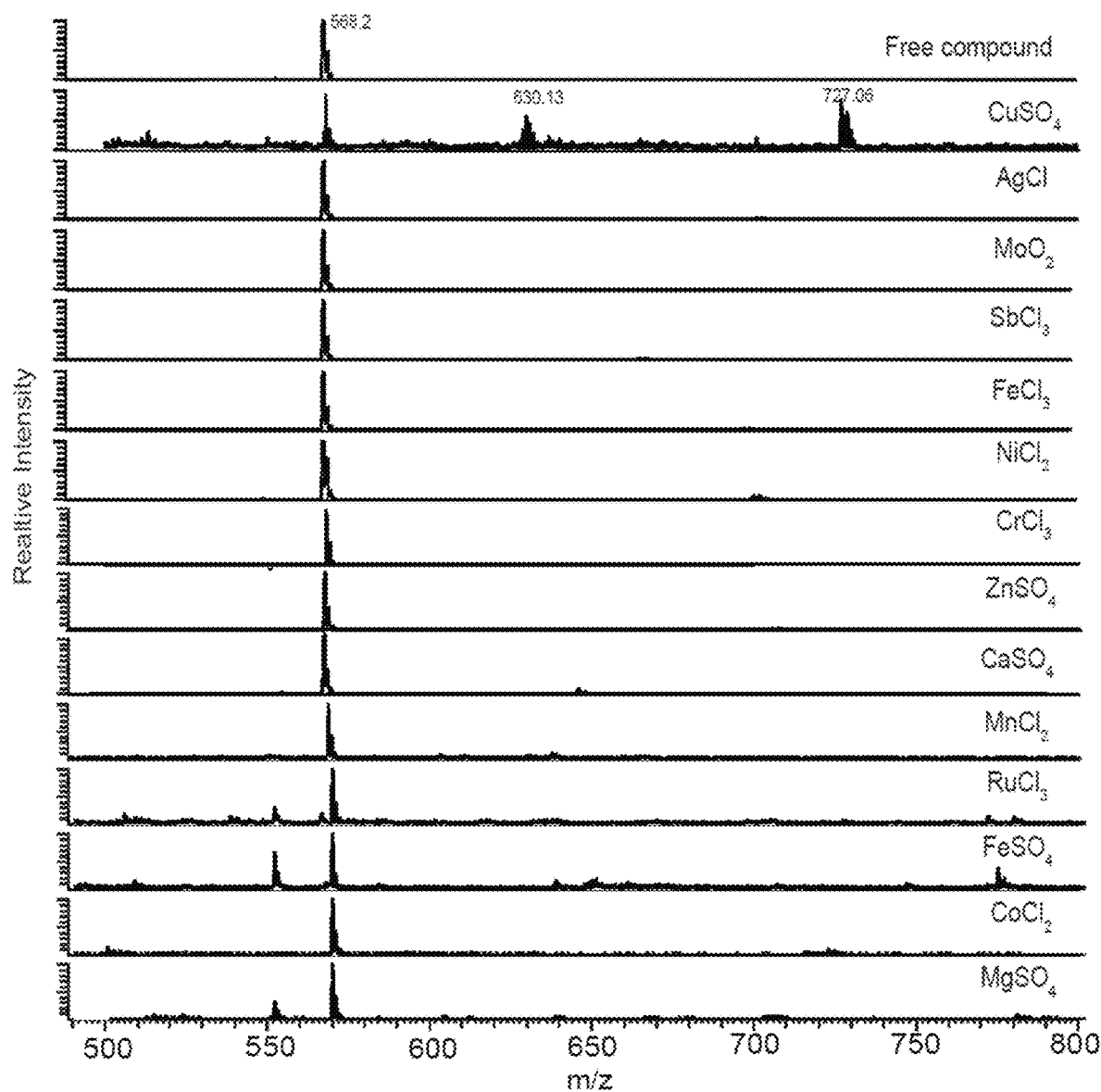

FIG. 18 shows ESI-MS spectra for complex formation between DPM-1001 (1 mM) and the indicated metals (8 mM).

Figure 19:
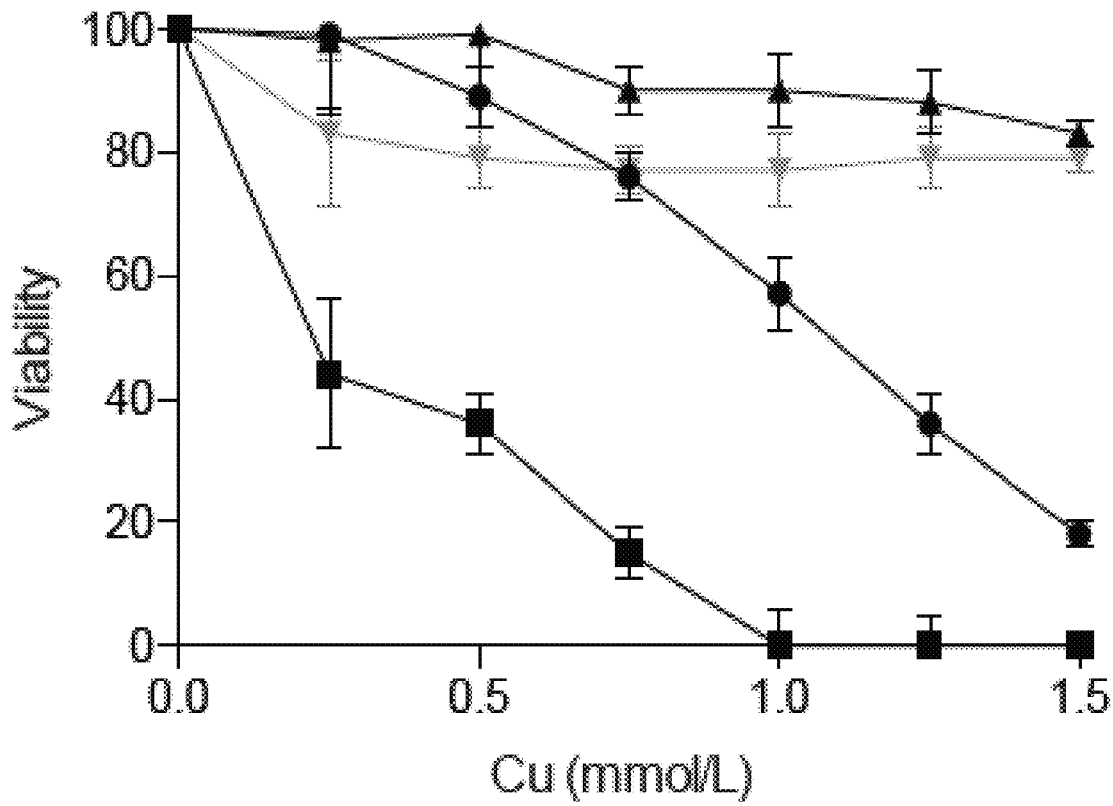

FIG. 19 shows survival of control cells with (upward triangle) or without (circle) DPM-1001, and ATP7B-knockdown cells (ATP7B-KD1) with (grey, downward triangle) and without DPM-1001 (square) measured at increasing concentrations of copper from 0-1.5 mM.

Figure 20:
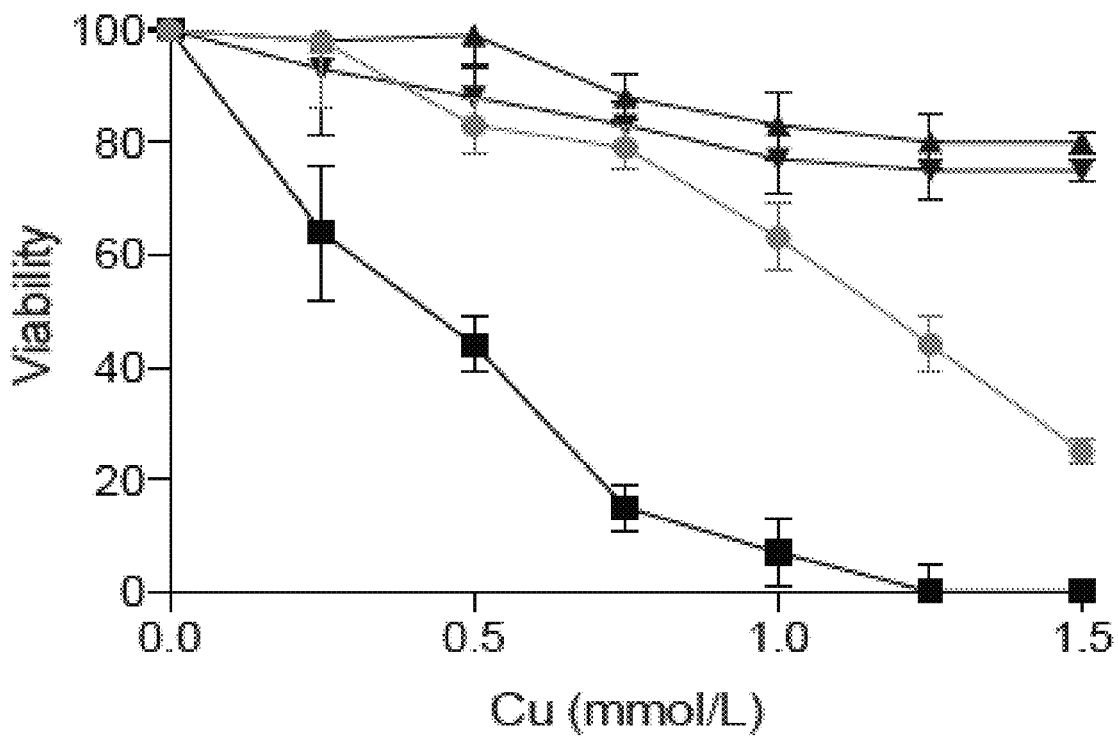
Figure 21:
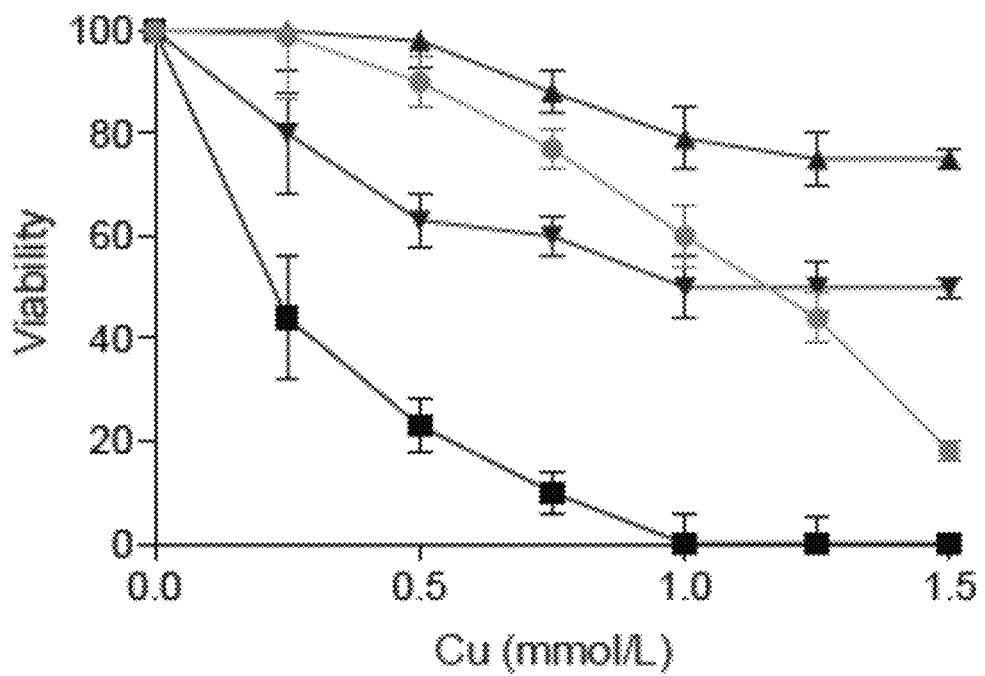

FIG. 20 shows survival of control fibroblasts with (upward triangle) and without (downward triangle) DPM-1001 compared with fibroblasts derived from Wilson's disease patients (GM00032 (top panel)), with (grey, circle) and without (square) DPM-1001, measured at increasing concentrations of copper from 0-1.5 mM FIG. 21 shows survival of control fibroblasts with (upward triangle) and without (downward triangle) DPM-1001 compared with fibroblasts derived from Wilson's disease patients (GM00033 (middle panel)), with (grey, circle) and without (square) DPM-1001, measured at increasing concentrations of copper from 0-1.5 mM.

Figure 22:
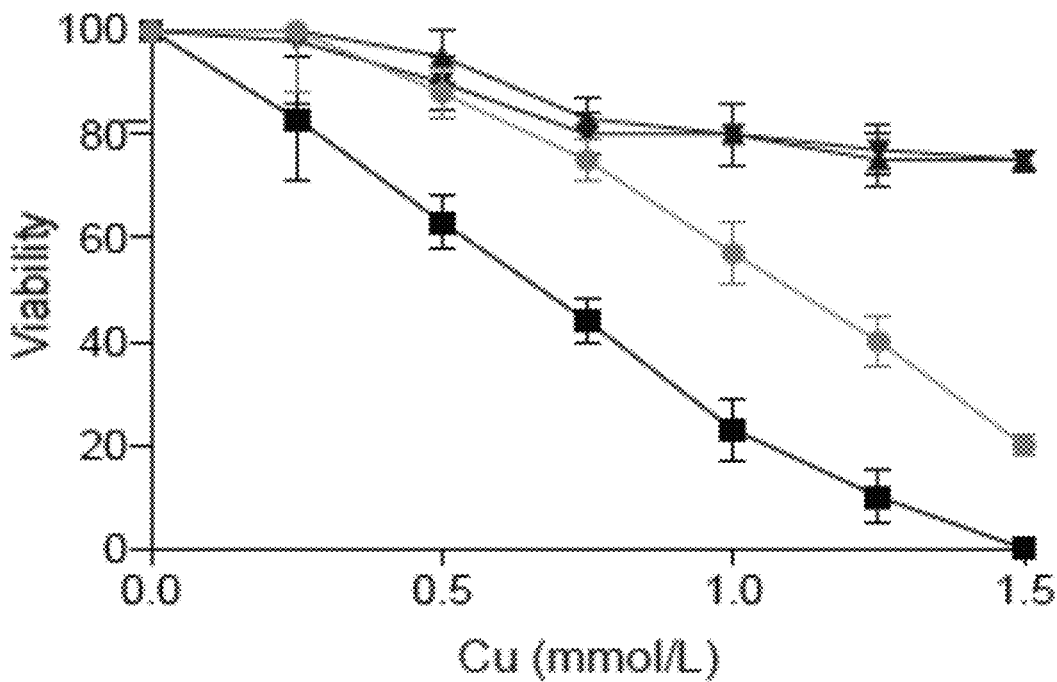

FIG. 22 shows survival of control fibroblasts with (upward triangle) and without (downward triangle) DPM-1001 compared with fibroblasts derived from Wilson's disease patients (GM05257 (lower panel)), with (grey, circle) and without (square) DPM-1001, measured at increasing concentrations of copper from 0-1.5 mM.

Figure 23:
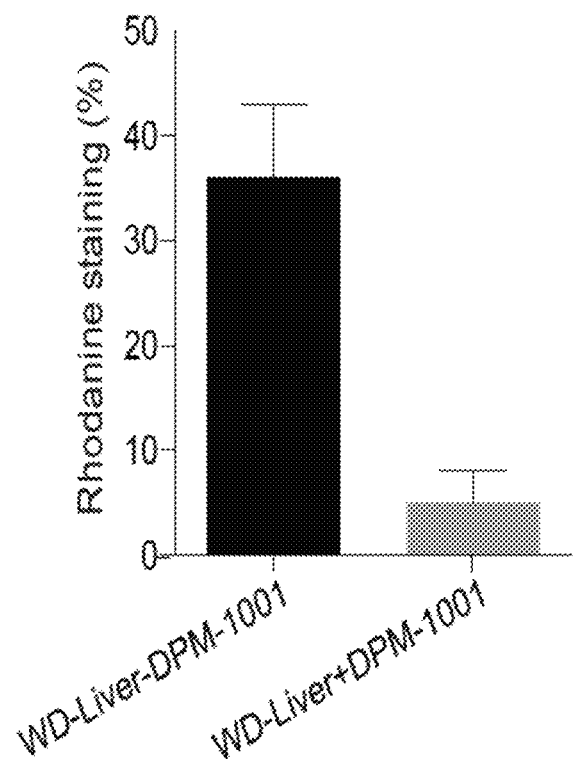

FIG. 23 shows levels of rhodanine staining of liver tissue from the TX mouse model stained from untreated or DPM-1001-treated animals.

Figure 24:
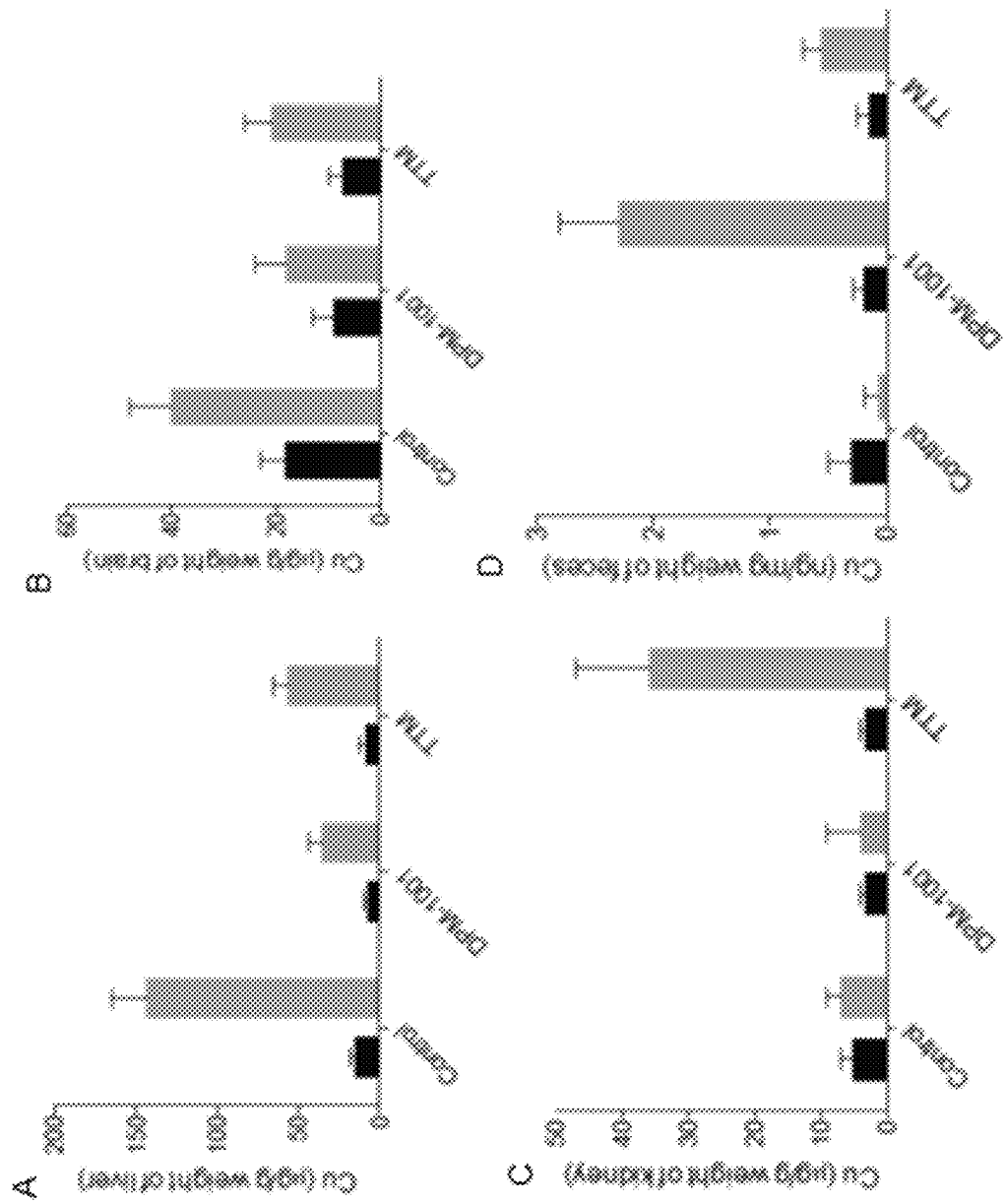

FIG. 24 shows copper levels in (A) liver, (B) brain and (C) kidney from wild-type (black bars) or TX (grey bars) mice measured using ICP-MS following treatment with saline, DPM-1001 (5 mg/kg, orally, every third day) or tetrathiomolybdate (TTM) (5 mg/kg, intraperitoneally, daily) for two weeks. Panel (D) represents the levels of copper in the feces of these animals.

Figure 25:
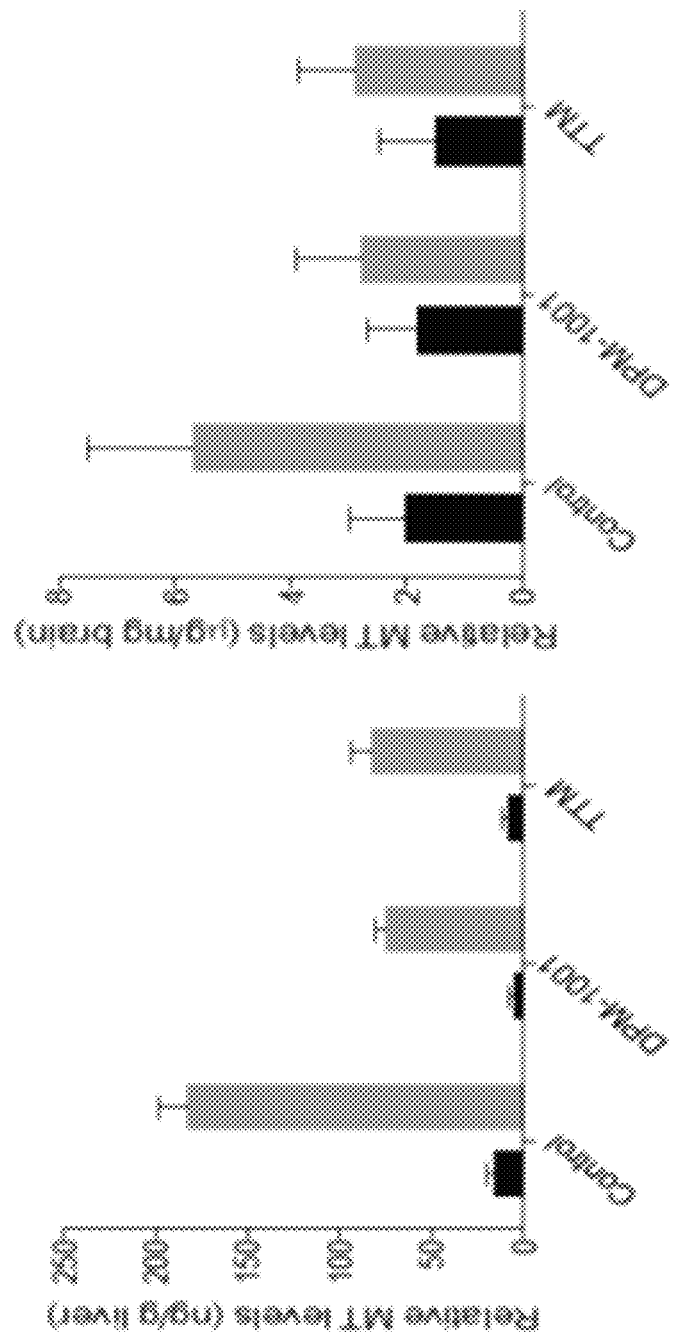

FIG. 25 shows levels of metallothionein in liver (left) or brain (right) from wild-type (black bars) and TX (grey bars) mice treated with saline, DPM-1001 or tertrathiomolybdate (TTM).

Figure 26:
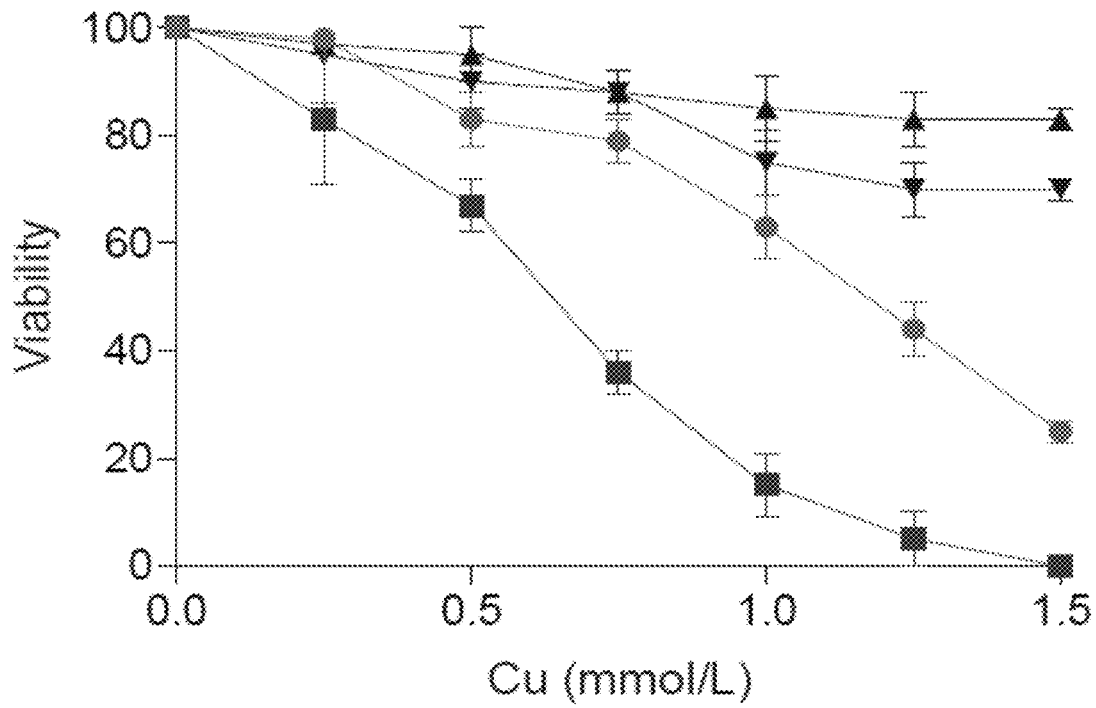

FIG. 26 shows survival of control fibroblasts with (upward triangle) and without (downward triangle) DPM-1001 compared with fibroblasts derived from Wilson's disease patients GM12158 with (grey, circle) and without (square) DPM-1001, measured at increasing concentrations of copper from 0-1.5 mM.

Figure 27:
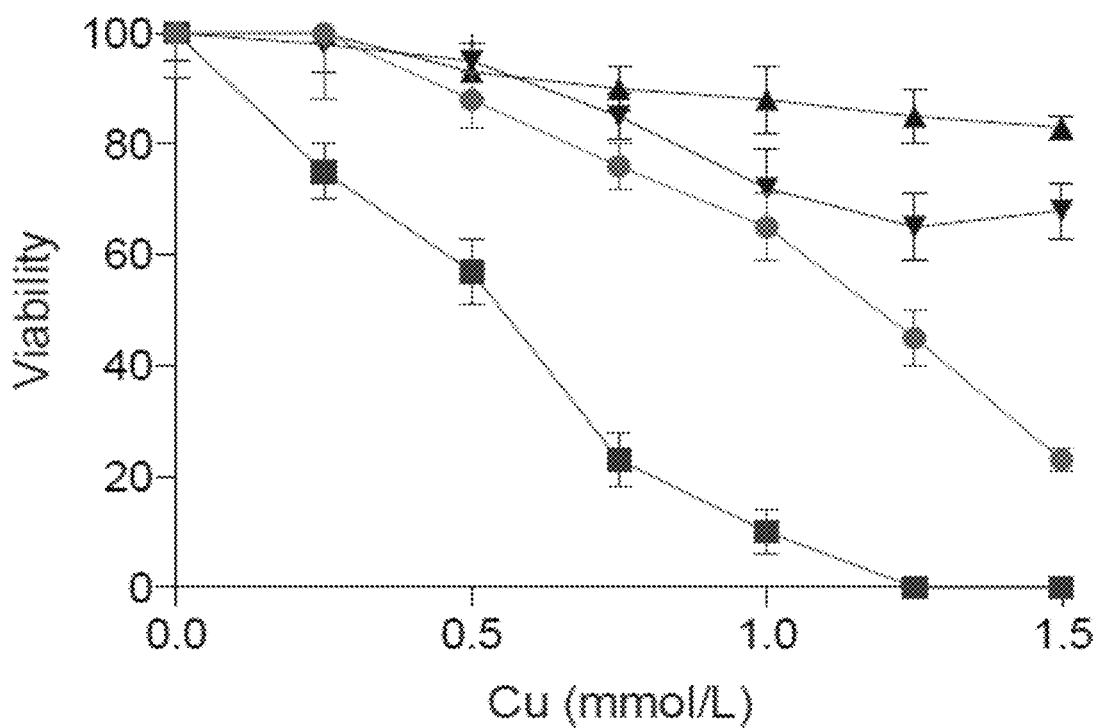

FIG. 27 shows survival of control fibroblasts with (upward triangle) and without (downward triangle) DPM-1001 compared with fibroblasts derived from Wilson's disease patients GM05798 (B) with (grey, circle) and without (square) DPM-1001, measured at increasing concentrations of copper from 0-1.5 mM.

Figure 28:
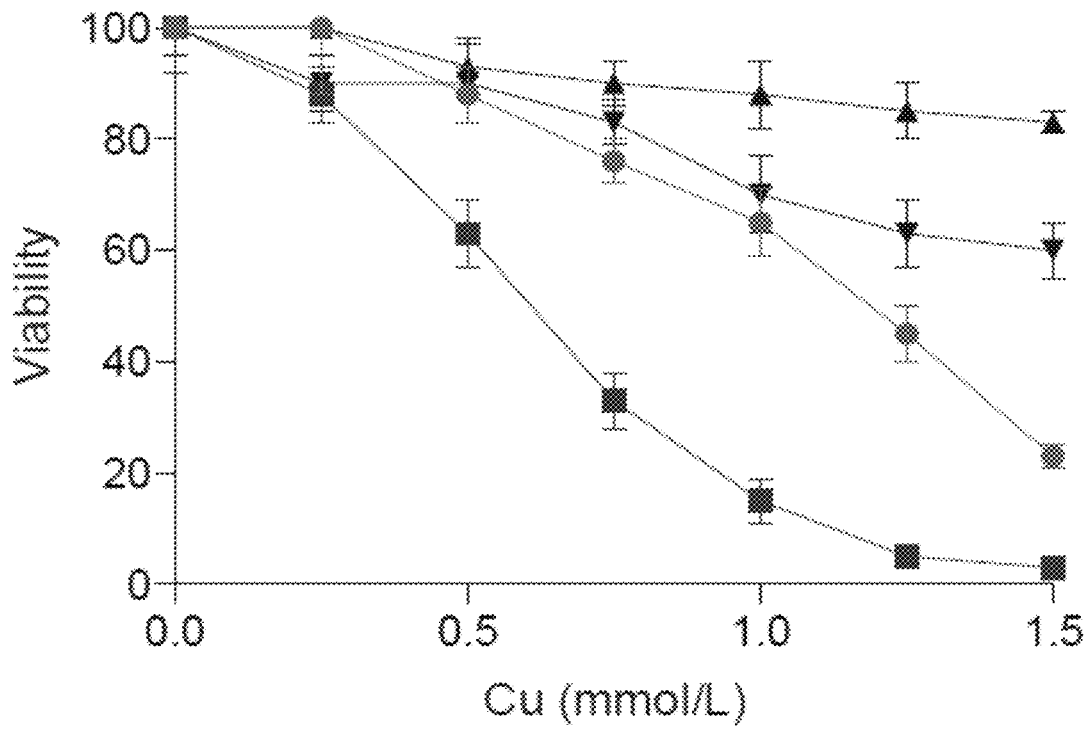

FIG. 28 shows survival of control fibroblasts with (upward triangle) and without (downward triangle) DPM-1001 compared with fibroblasts derived from Wilson's disease patients GM11778 (C) with (grey, circle) and without (square) DPM-1001, measured at increasing concentrations of copper from 0-1.5 mM.

Figure 29:
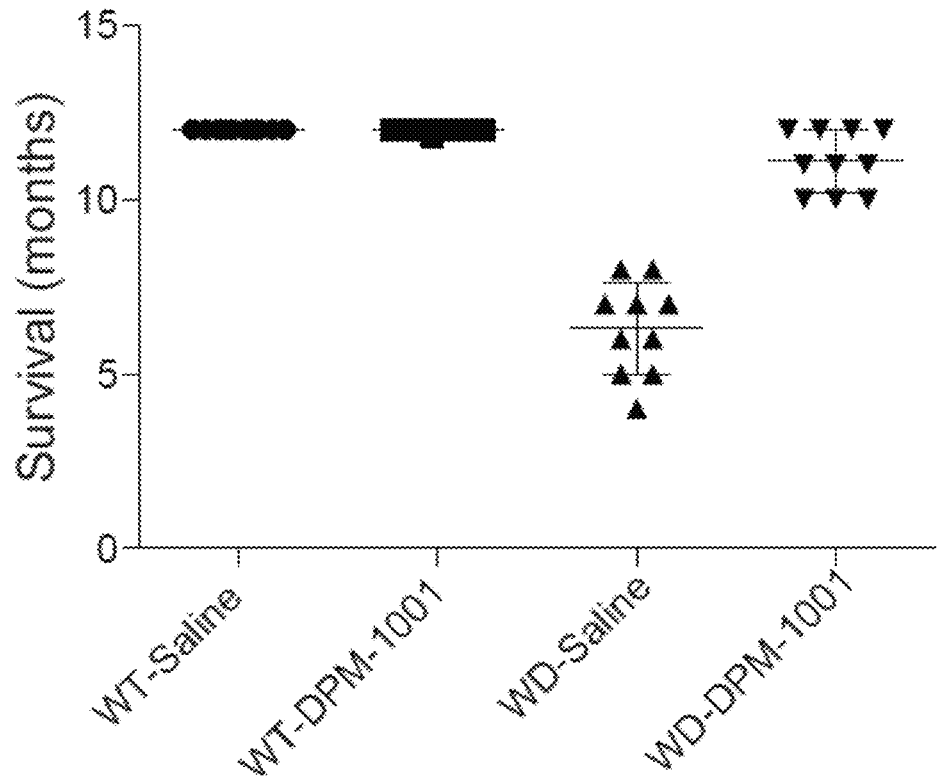

FIG. 29 shows survival of wild-type (WT) and TX Wilson's disease (WD) mice treated with saline or DPM-1001 (2 mg/kg) over 12 months.

Figure 30:
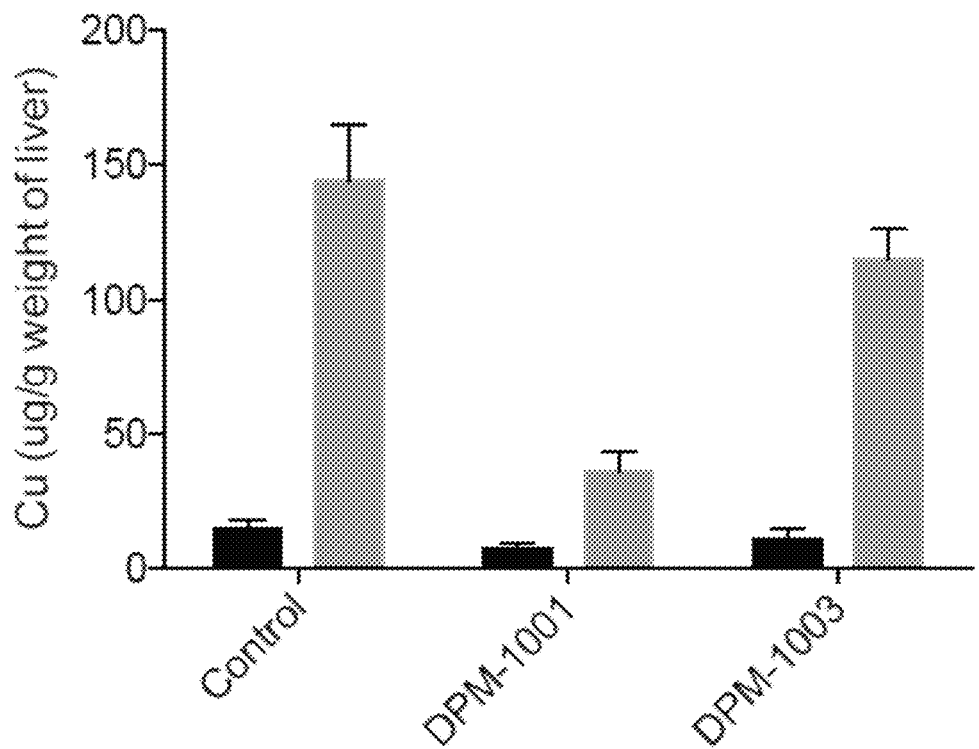

FIG. 30 shows copper levels in the liver of WT (black bars) and TX (grey bars) mice treated with saline, DPM-1001 (2 mg/kg) or DPM-1003 (2 mg/kg) once every third day using ICP-MS.

Figure 31:
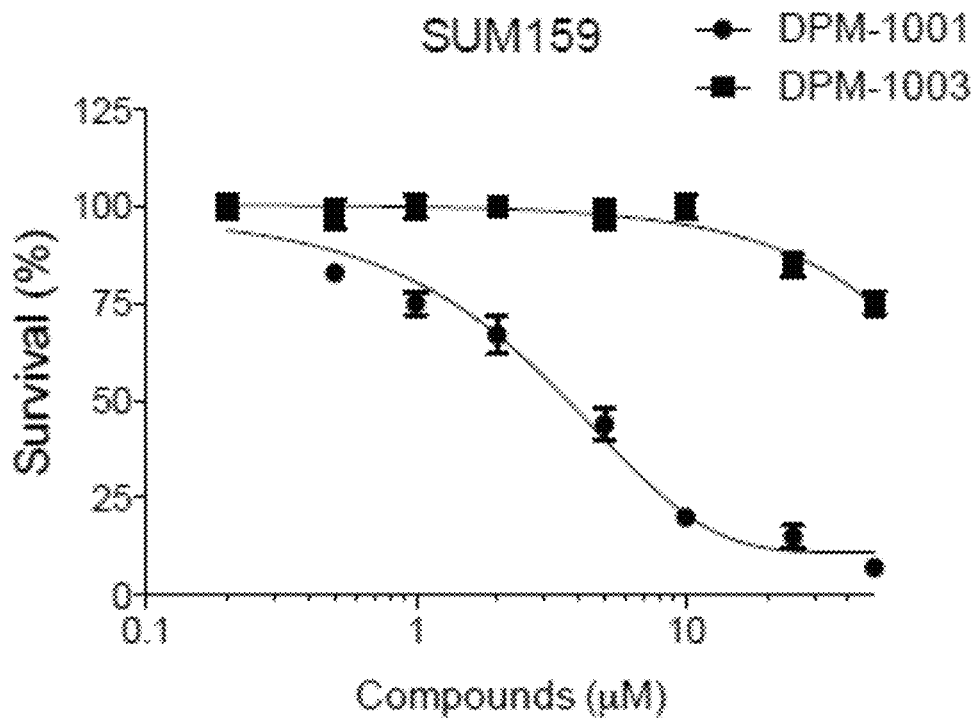

FIG. 31 shows the effect of DPM-1001 and DPM-1003 on survival of SUM159 cells.

Figure 32:
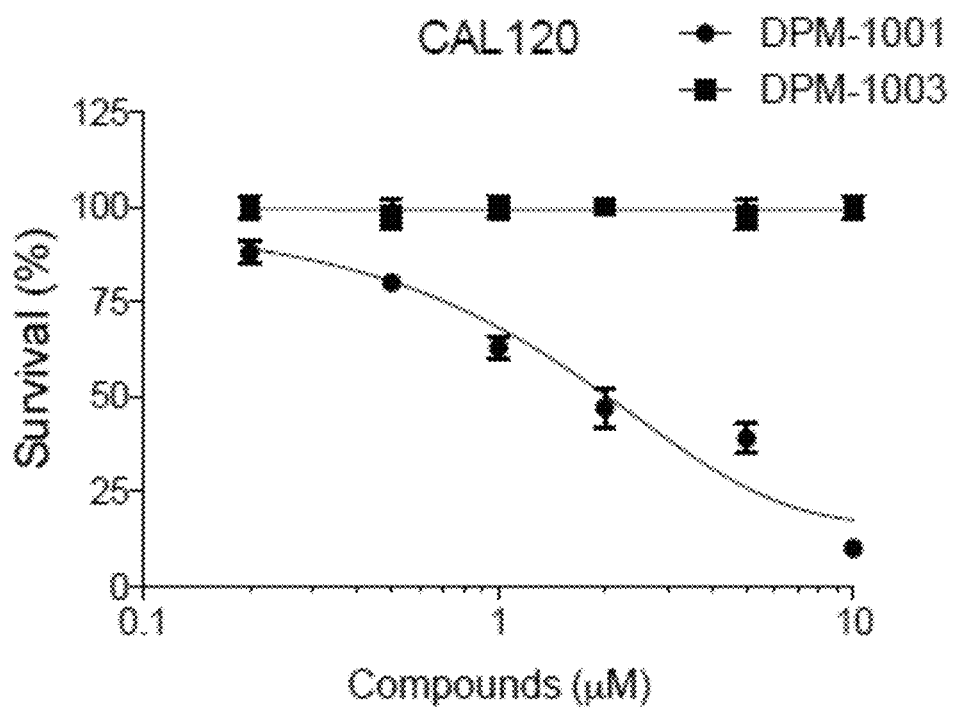

FIG. 32 shows the effect of DPM-1001 and DPM-1003 on survival of CAL120 cells.

Figure 33:
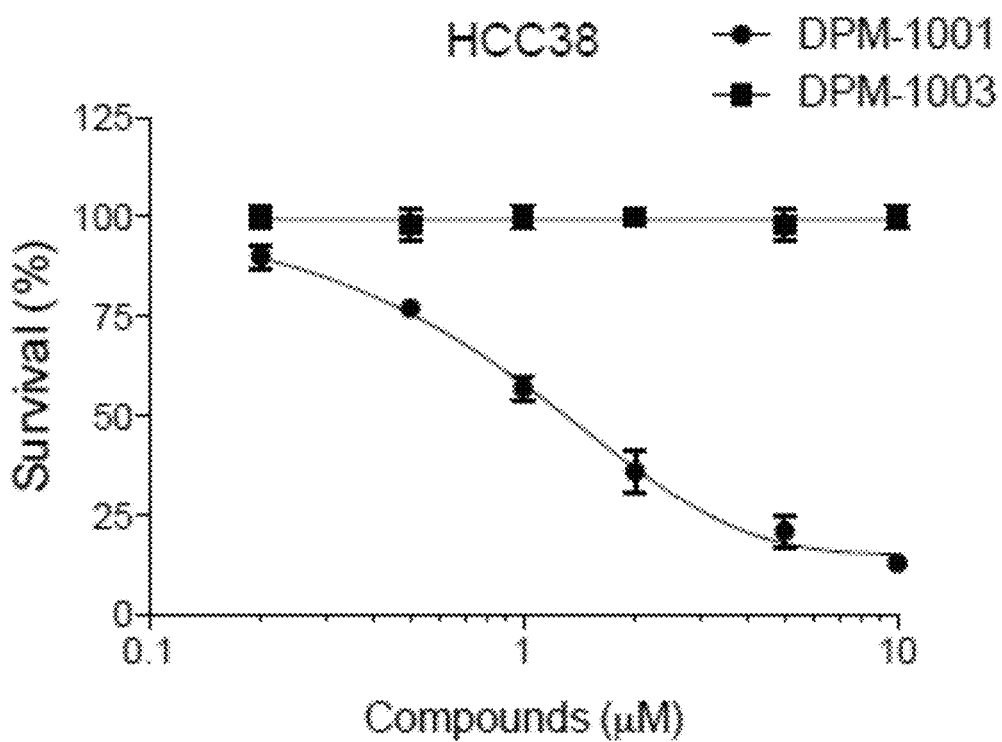

FIG. 33 shows the effect of DPM-1001 and DPM-1003 on survival of HCC38 cells.

Figure 34:
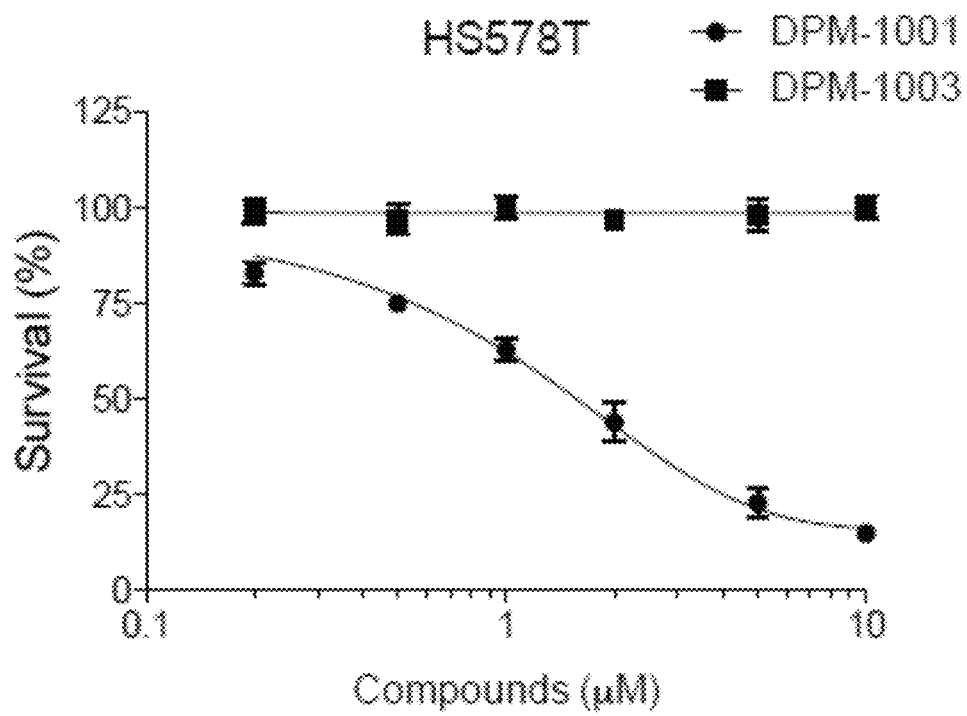

FIG. 34 shows the effect of DPM-1001 and DPM-1003 on survival of HS578T cells.

Figure 35:
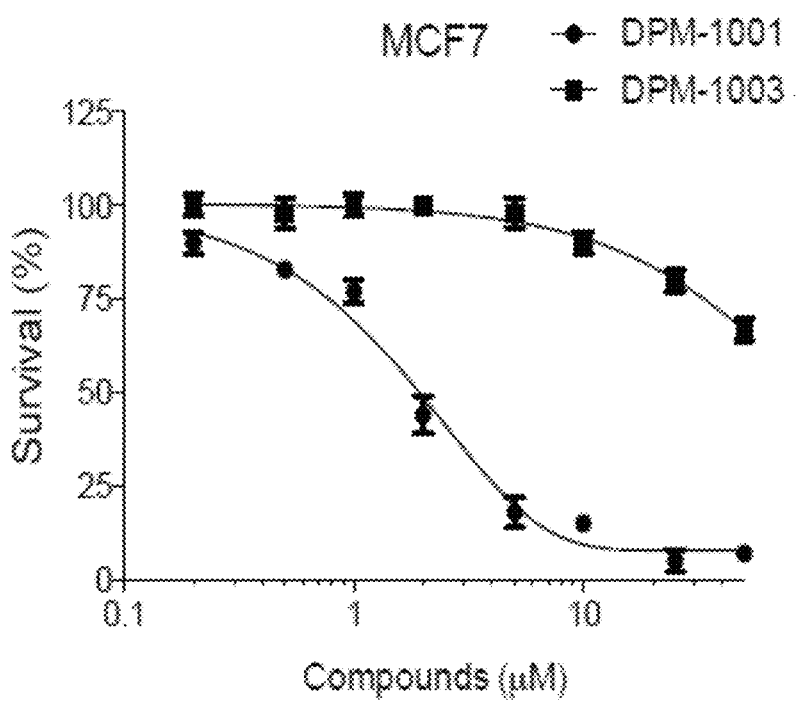

FIG. 35 shows the effect of DPM-1001 and DPM-1003 on survival of MCF7 cells.

Figure 36:
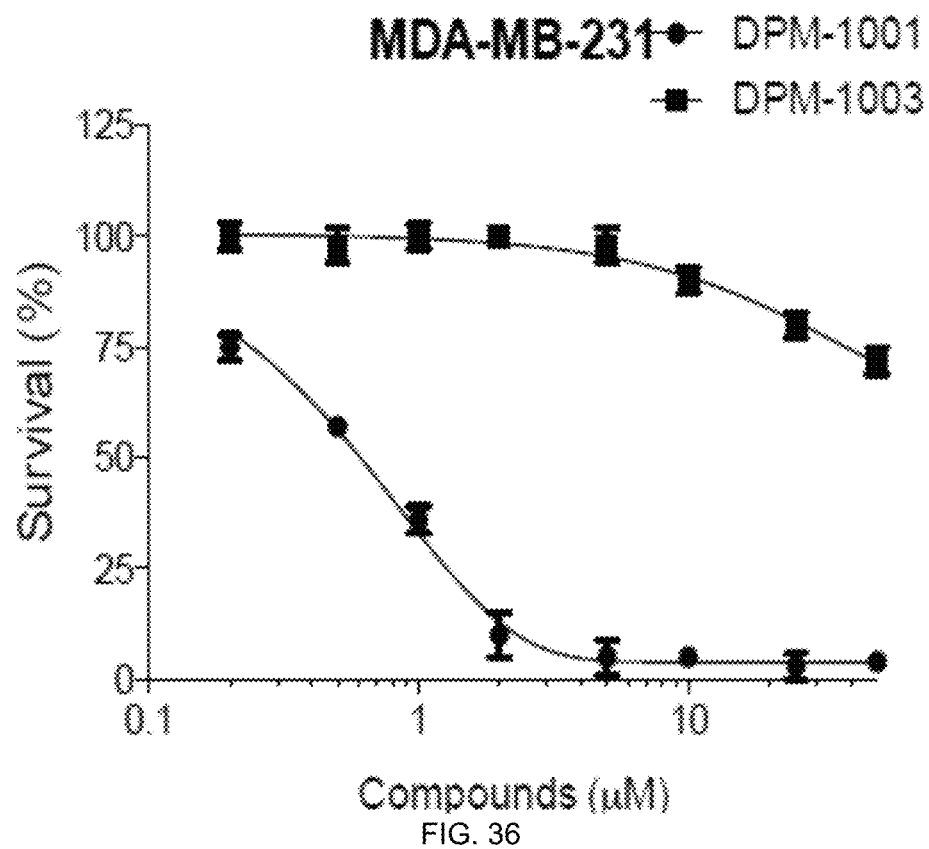

FIG. 36 shows the effect of DPM-1001 and DPM-1003 on survival of MDA-MB-231 cells.

Figure 37:
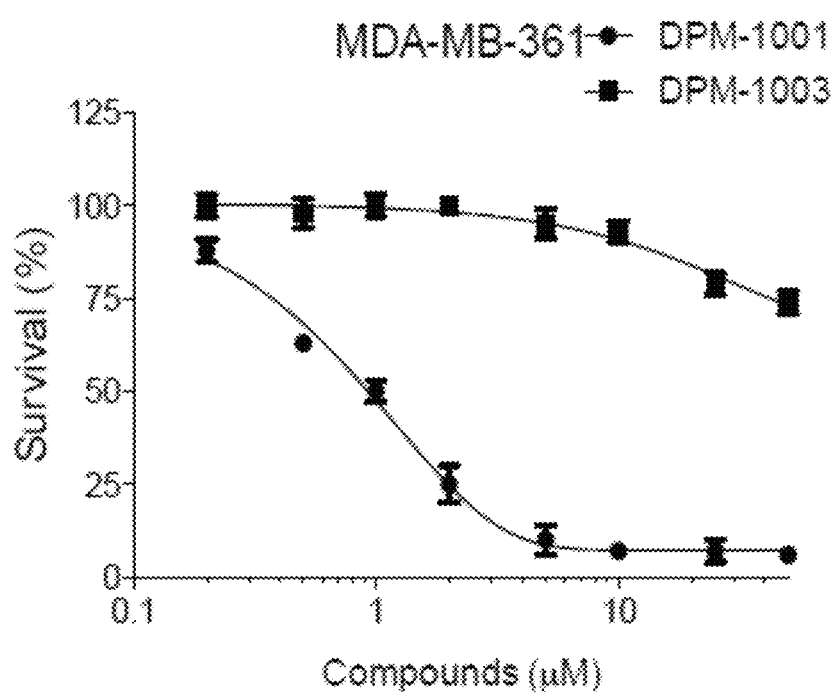

FIG. 37 shows the effect of DPM-1001 and DPM-1003 on survival of MDA-MB-361 cells.

Figure 38:
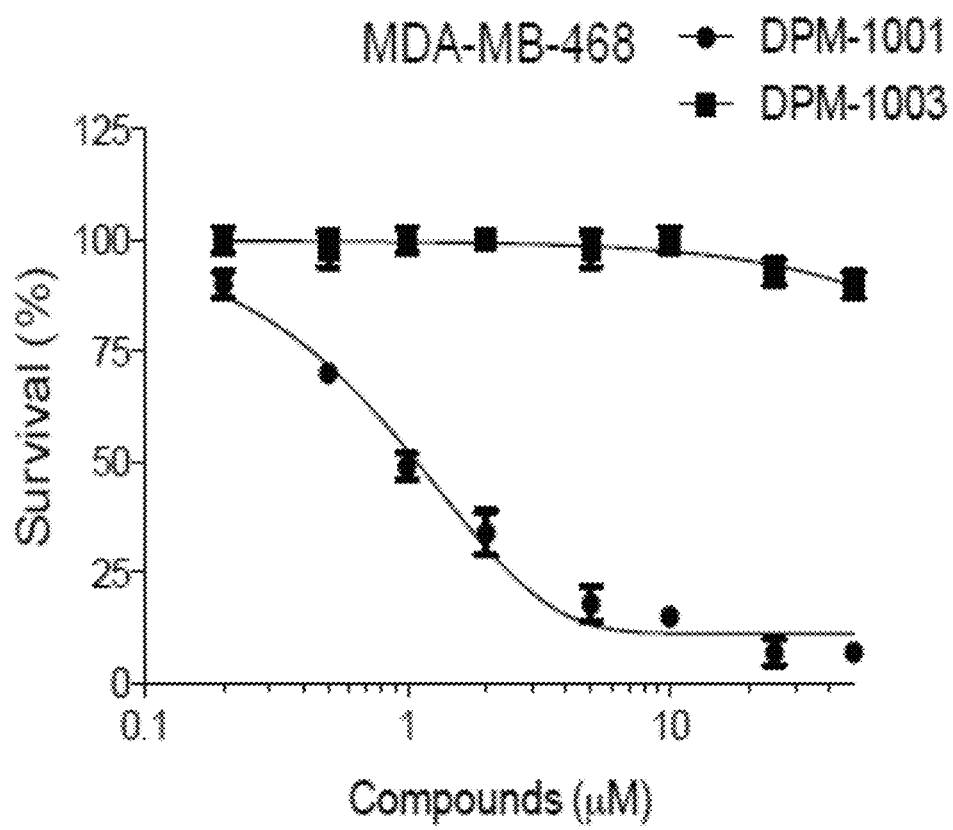

FIG. 38 shows the effect of DPM-1001 and DPM-1003 on survival of MDA-MB-468 cells.

Figure 39:
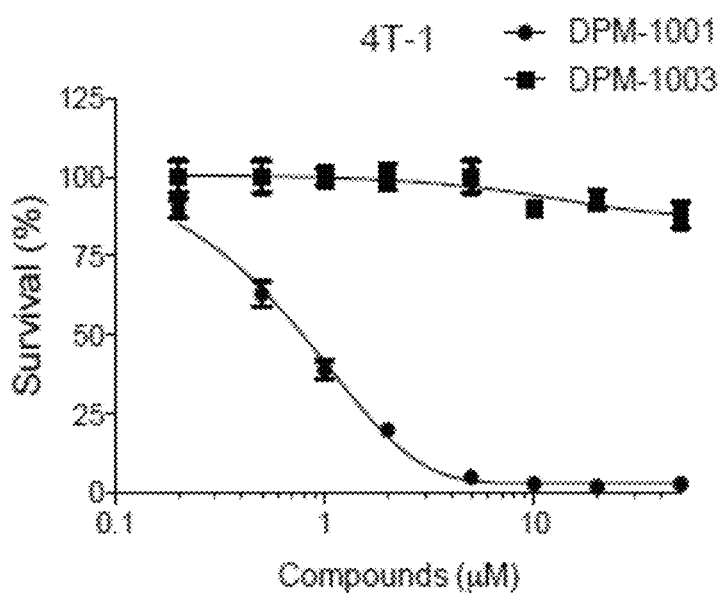

FIG. 39 shows the effect of DPM-1001 and DPM-1003 on survival of 4T-1 cells.

Figure 40:
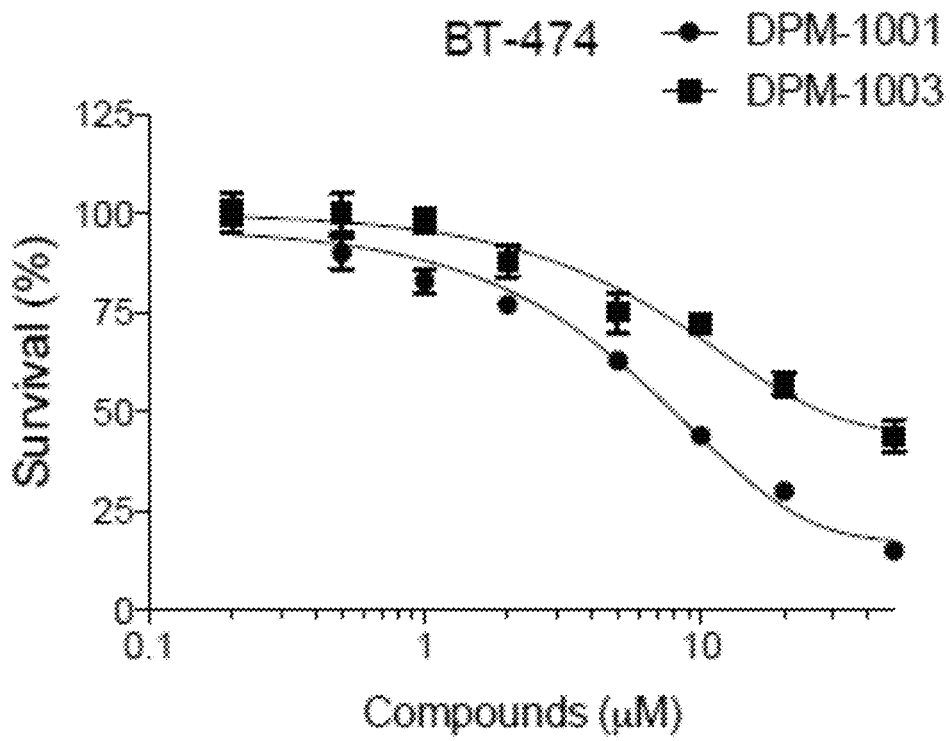

FIG. 40 shows the effect of DPM-1001 and DPM-1003 on survival of BT-474 cells.

Figure 41:
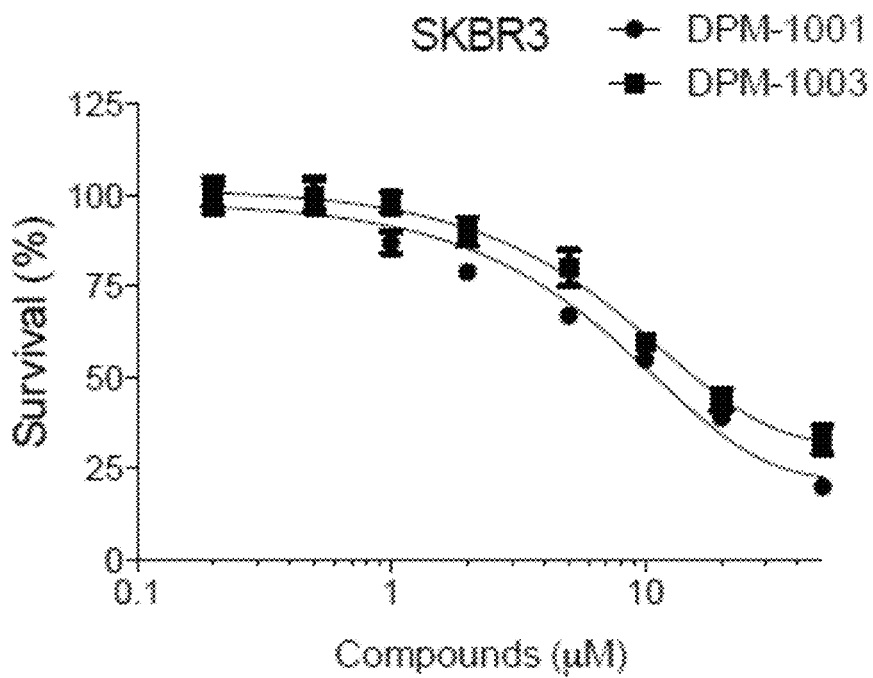

FIG. 41 shows the effect of DPM-1001 and DPM-1003 on survival of SKBR3 cells.

Figure 42:
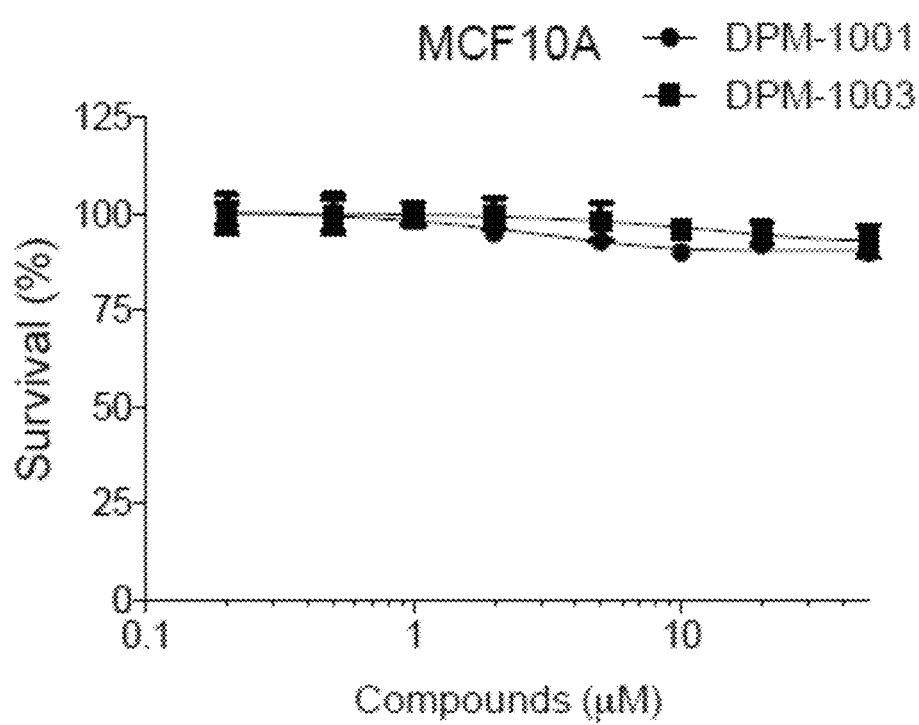

FIG. 42 shows the effect of DPM-1001 and DPM-1003 on survival of MCF10A cells.

Figure 43:
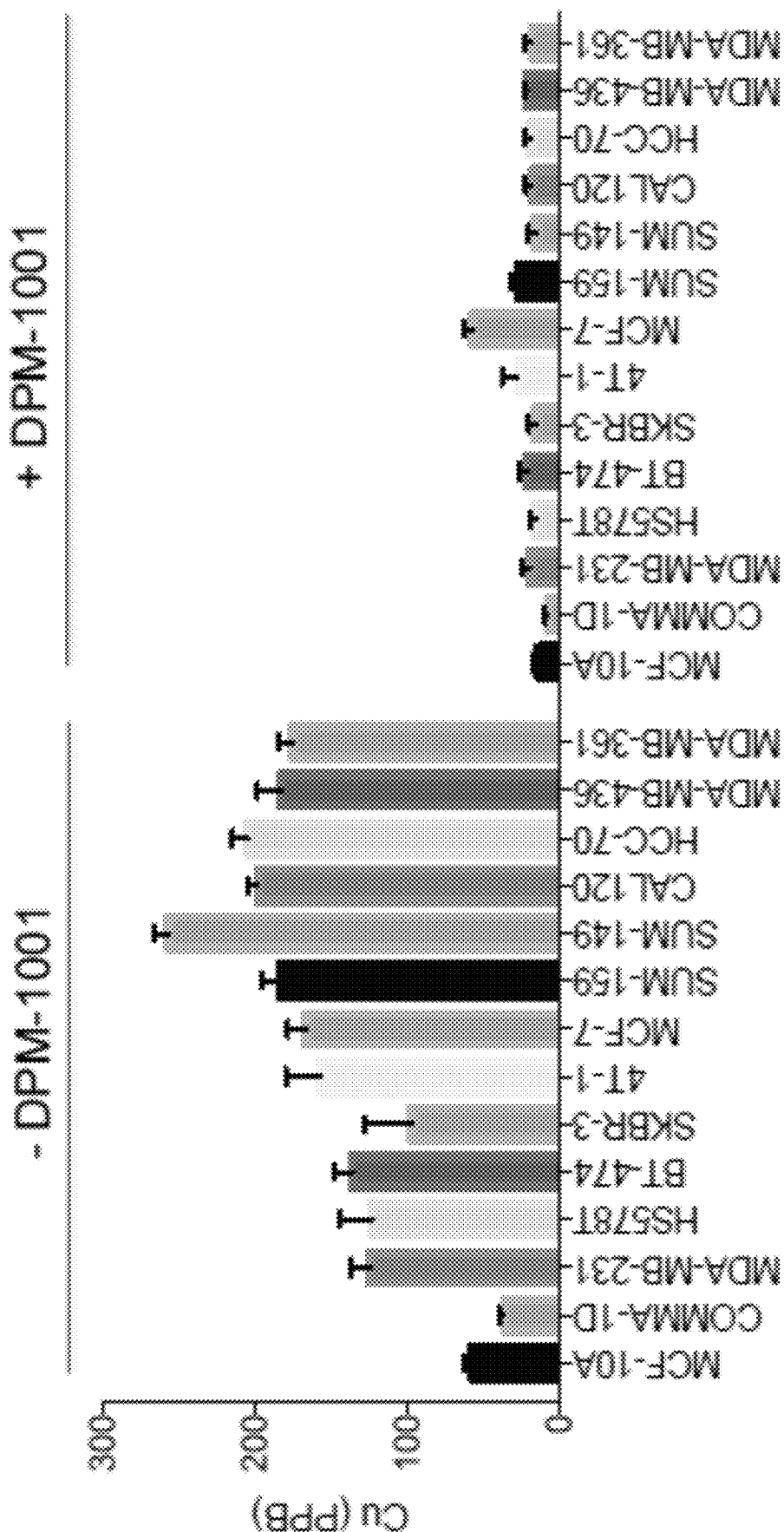

FIG. 43 shows depletion of copper by DPM-1001 in TNBC cells.

Figure 44:
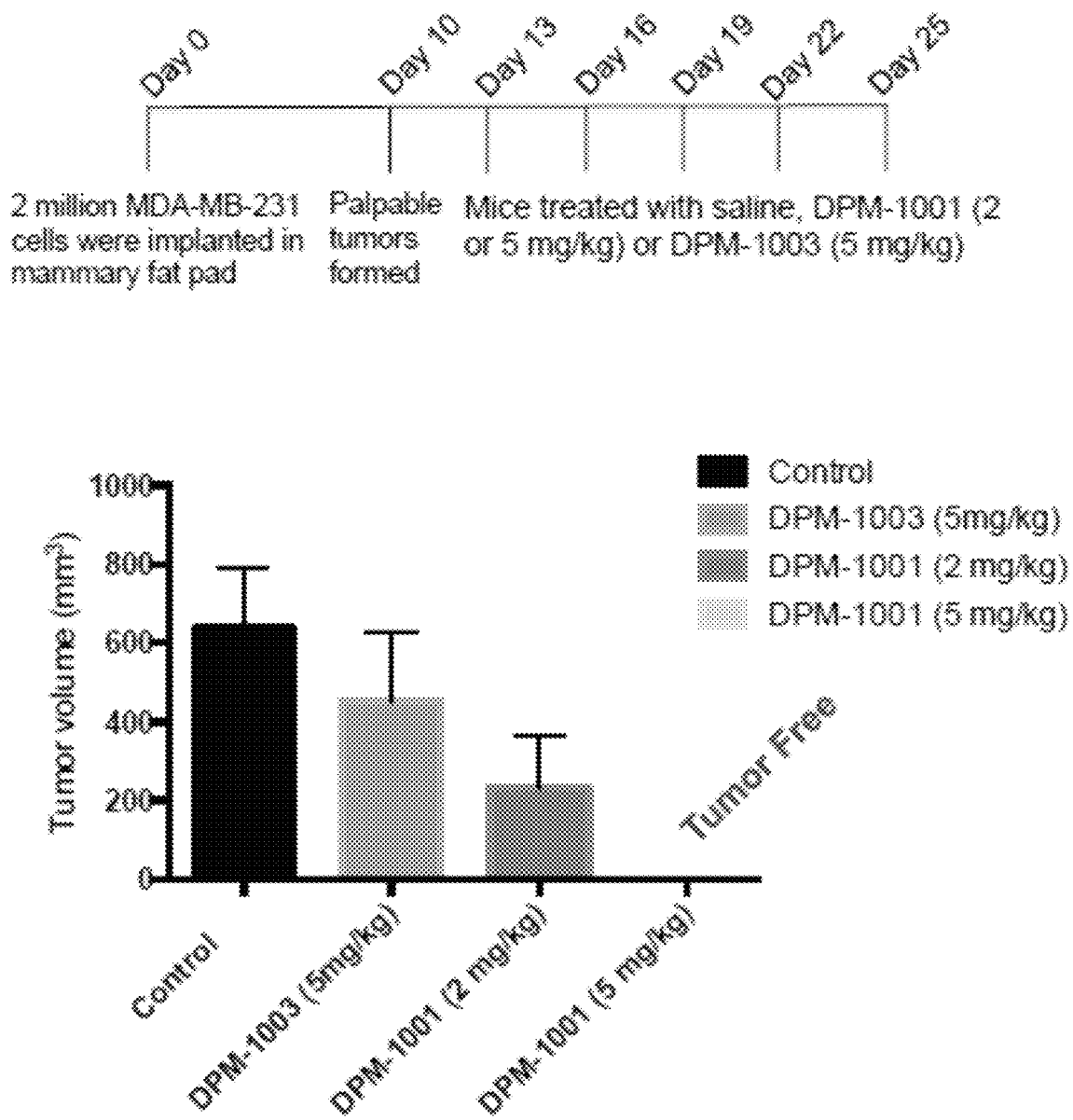

FIG. 44 shows inhibition of tumor size by DPM-1001 but not by DPM-1003.

Figure 45:
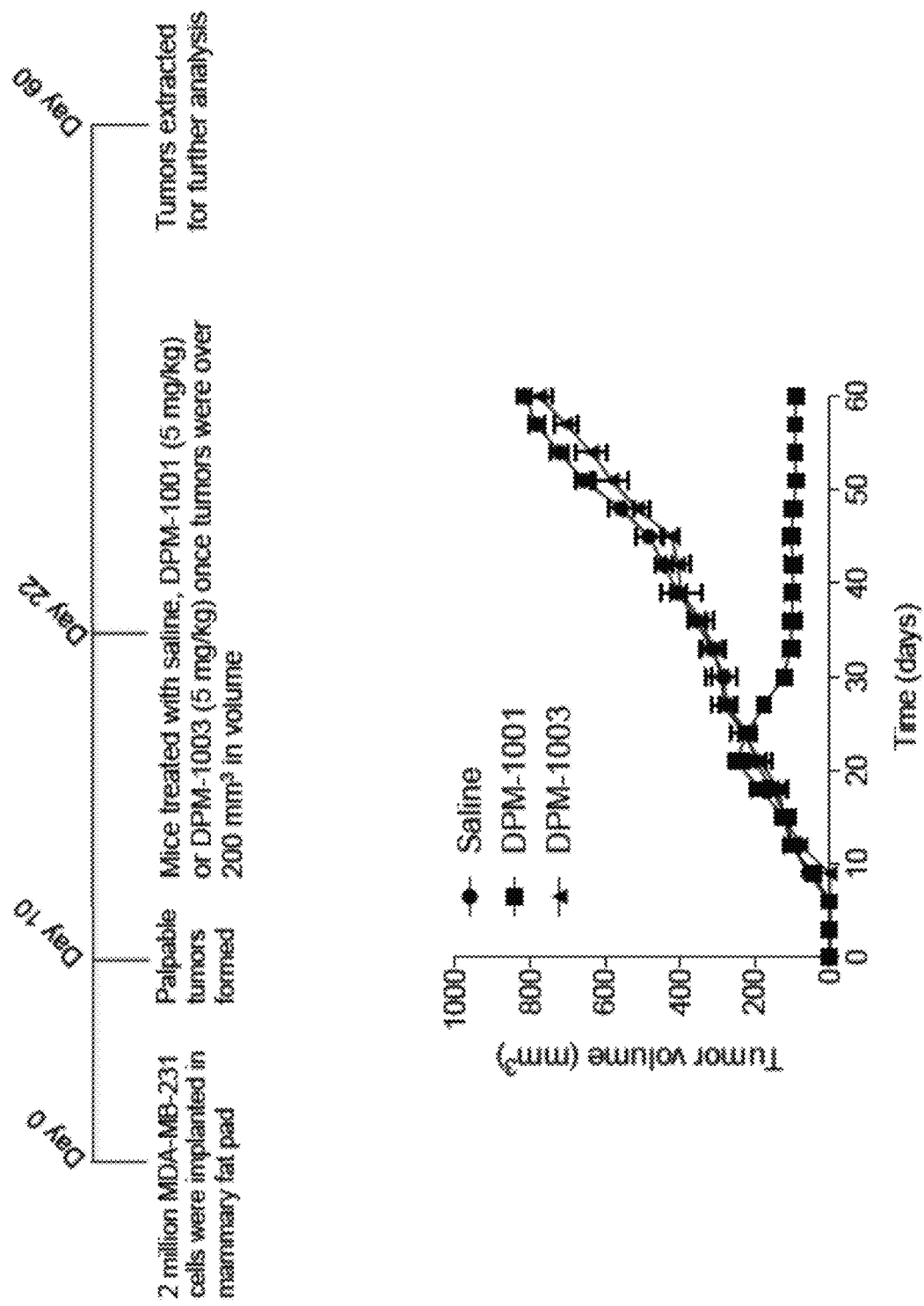

FIG. 45 shows inhibition of tumor size by DPM-1001 but not by DPM-1003.

Figure 46:
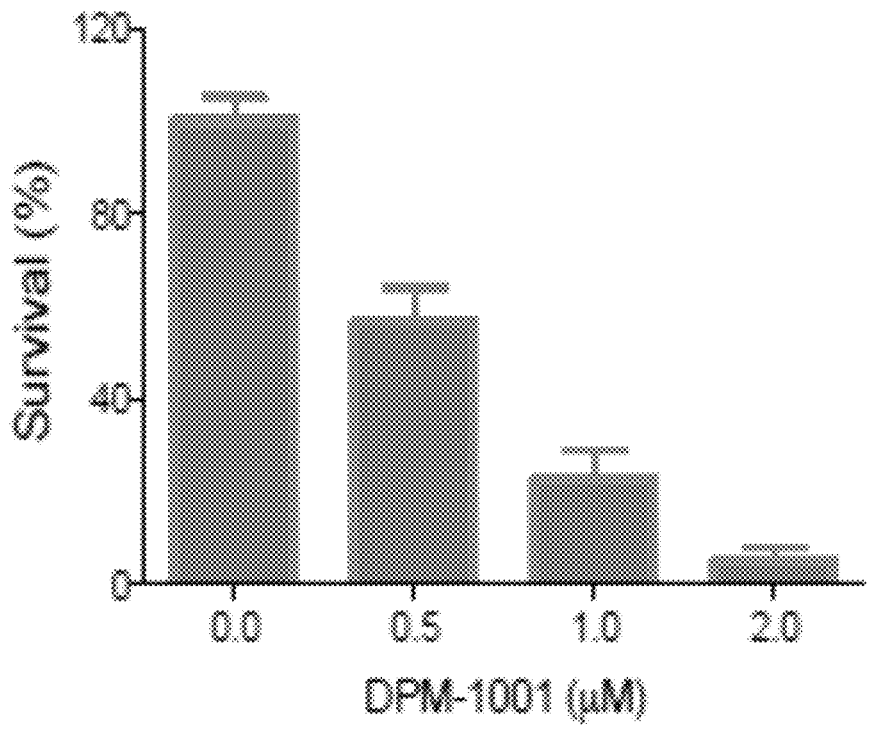

FIG. 46 shows inhibition of survival of MDA-MB-231 cells by DPM-1001.

Figure 47:
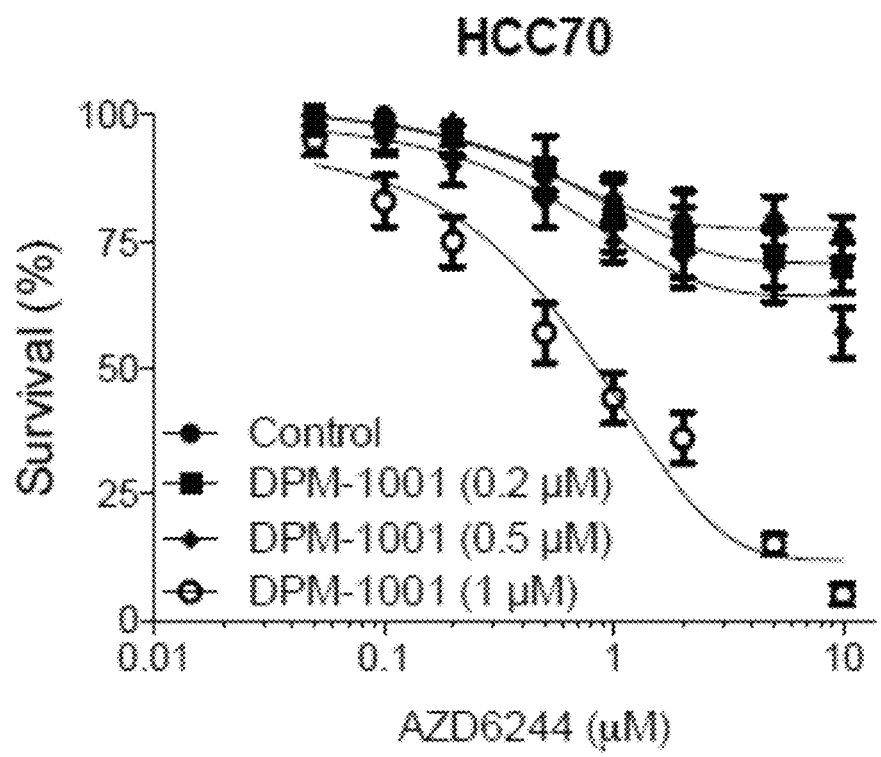

FIG. 47 shows inhibition of survival of HCC70 cells by treatment with DPM-1001 in combination with AZD6244.

Figure 48:
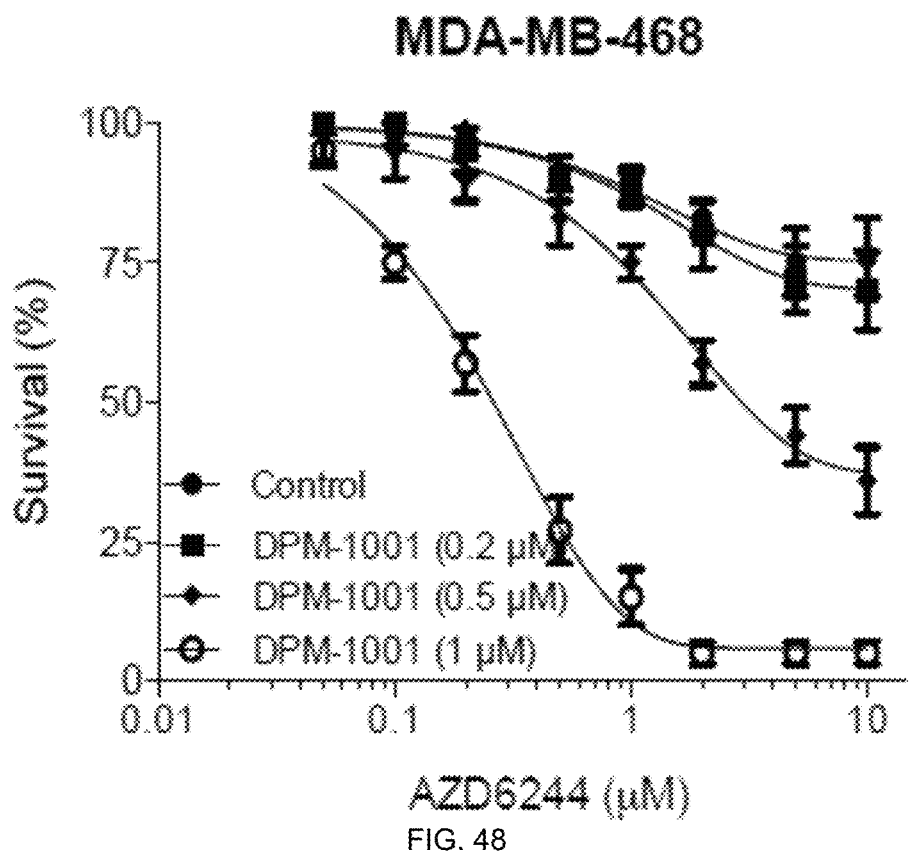

FIG. 48 shows inhibition of survival of MDA-MB-468 cells by treatment with DPM-1001 in combination with AZD6244.

Figure 49:
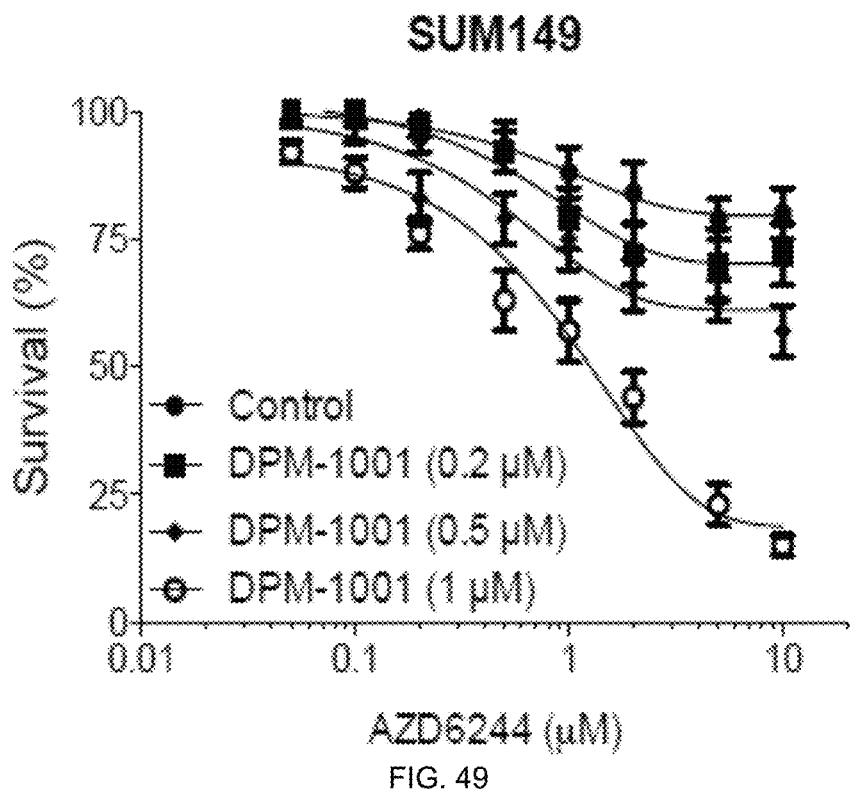

FIG. 49 shows inhibition of survival of SUM149 cells by treatment with DPM-1001 in combination with AZD6244.

Figure 50:
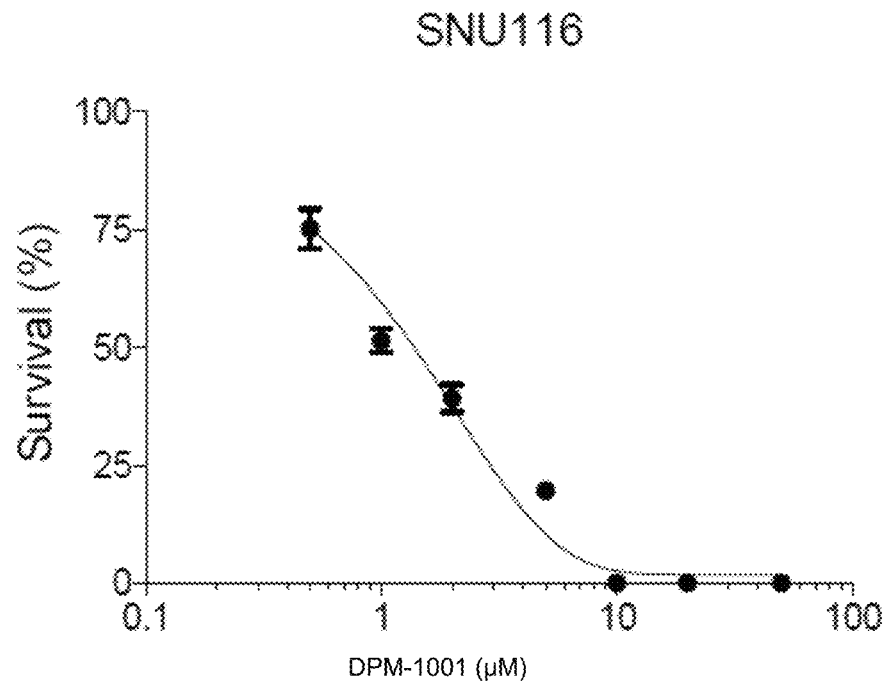

FIG. 50 shows the inhibitory effect of DPM-1001 on survival of SNU116 cells.

Figure 51:
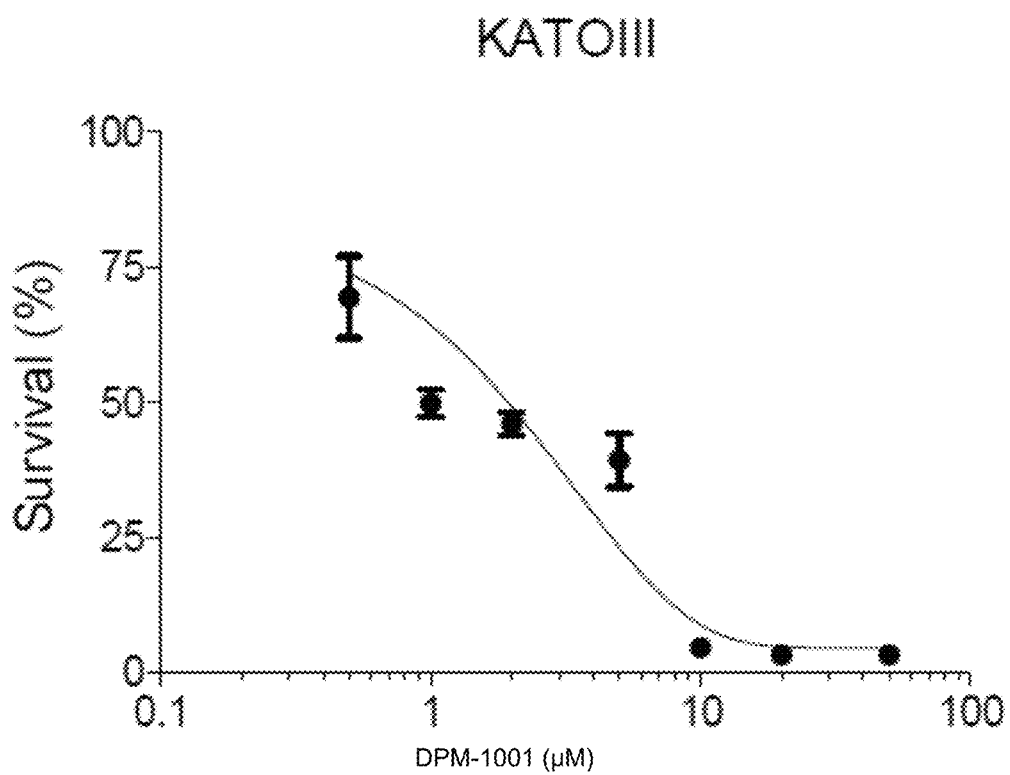

FIG. 51 shows the inhibitory effect of DPM-1001 on survival of KATOIII cells.

Figure 52:
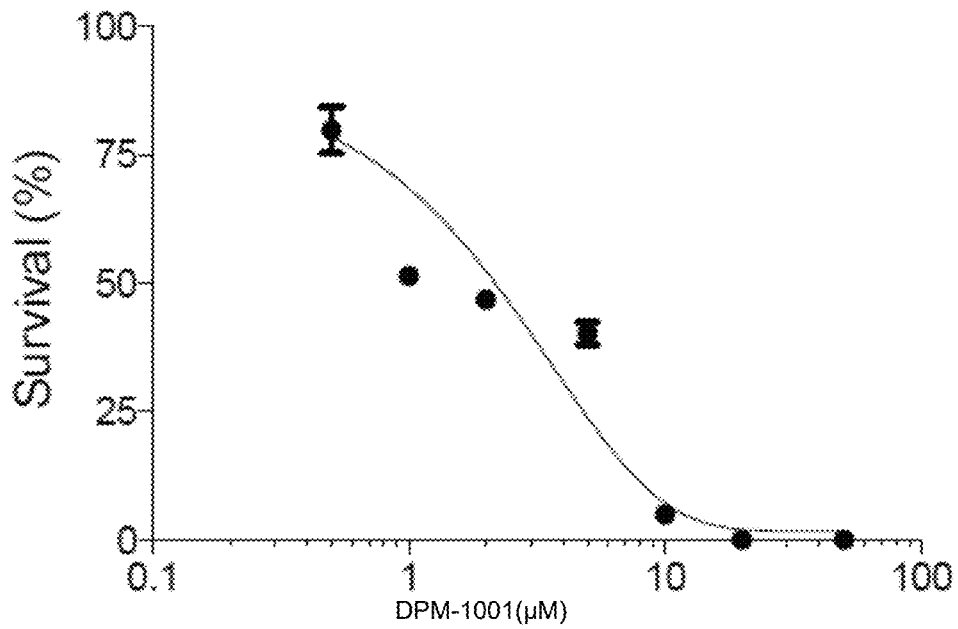

FIG. 52 shows the inhibitory effect of DPM-1001 on survival of SNU5 cells.

Figure 53:
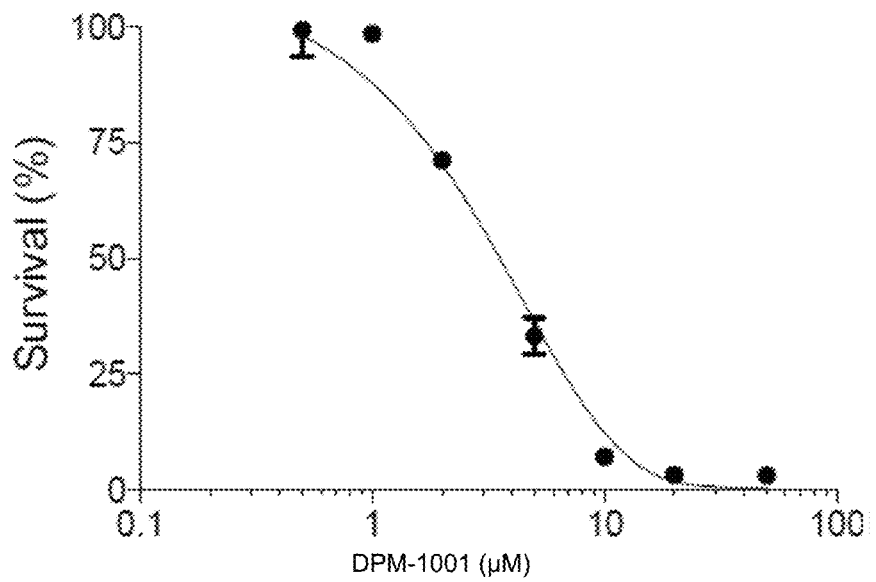

FIG. 53 shows the inhibitory effect of DPM-1001 on survival of AGS cells.

Figure 54:
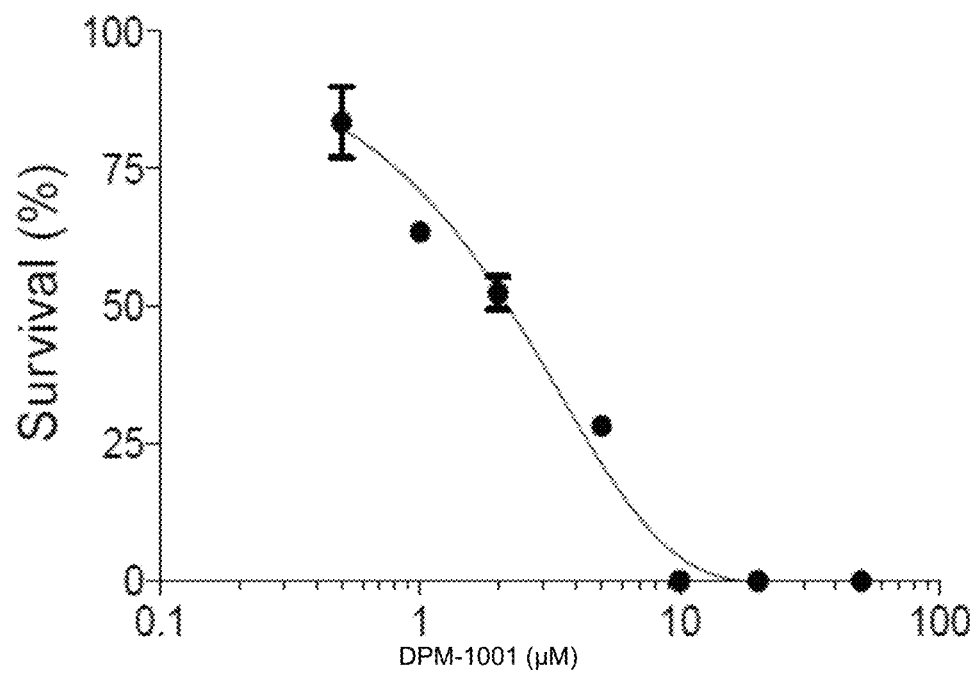

FIG. 54 shows the inhibitory effect of DPM-1001 on survival of MDA-MB-468 cells.

Figure 55:
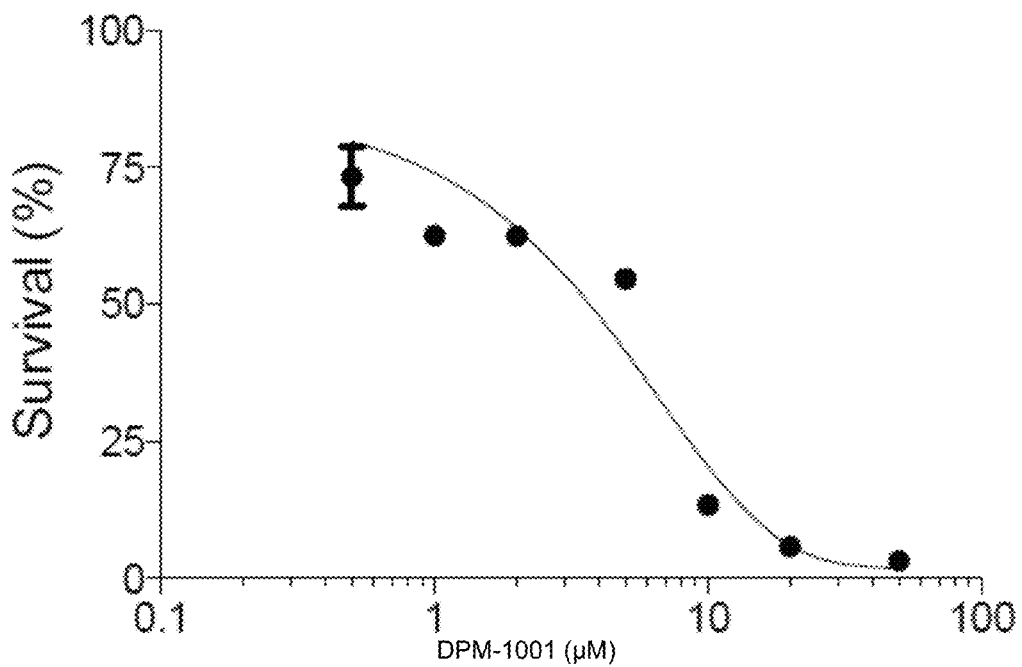

FIG. 55 shows the inhibitory effect of DPM-1001 on survival of N87.

Figure 56A:
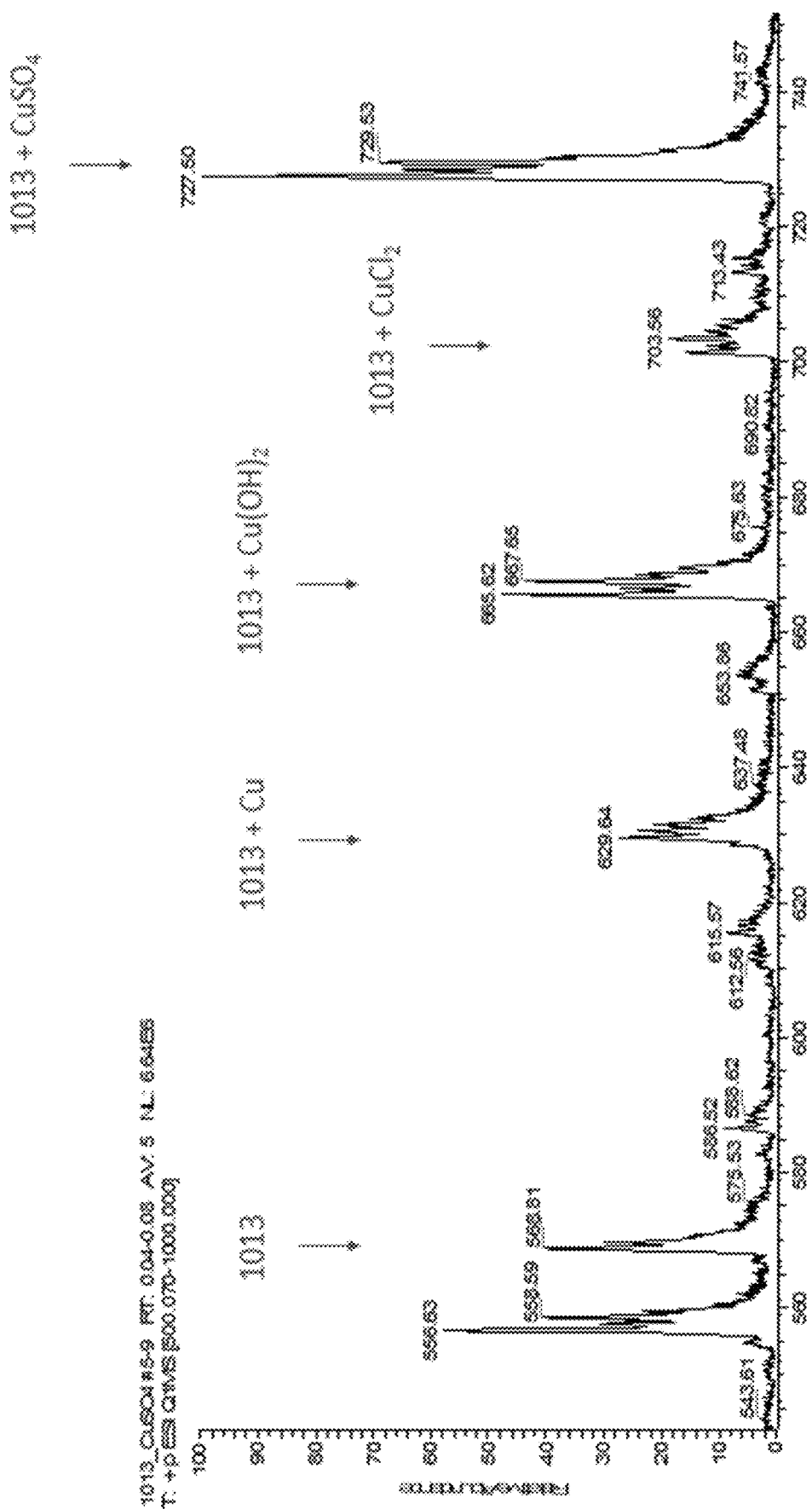
Figure 56B:
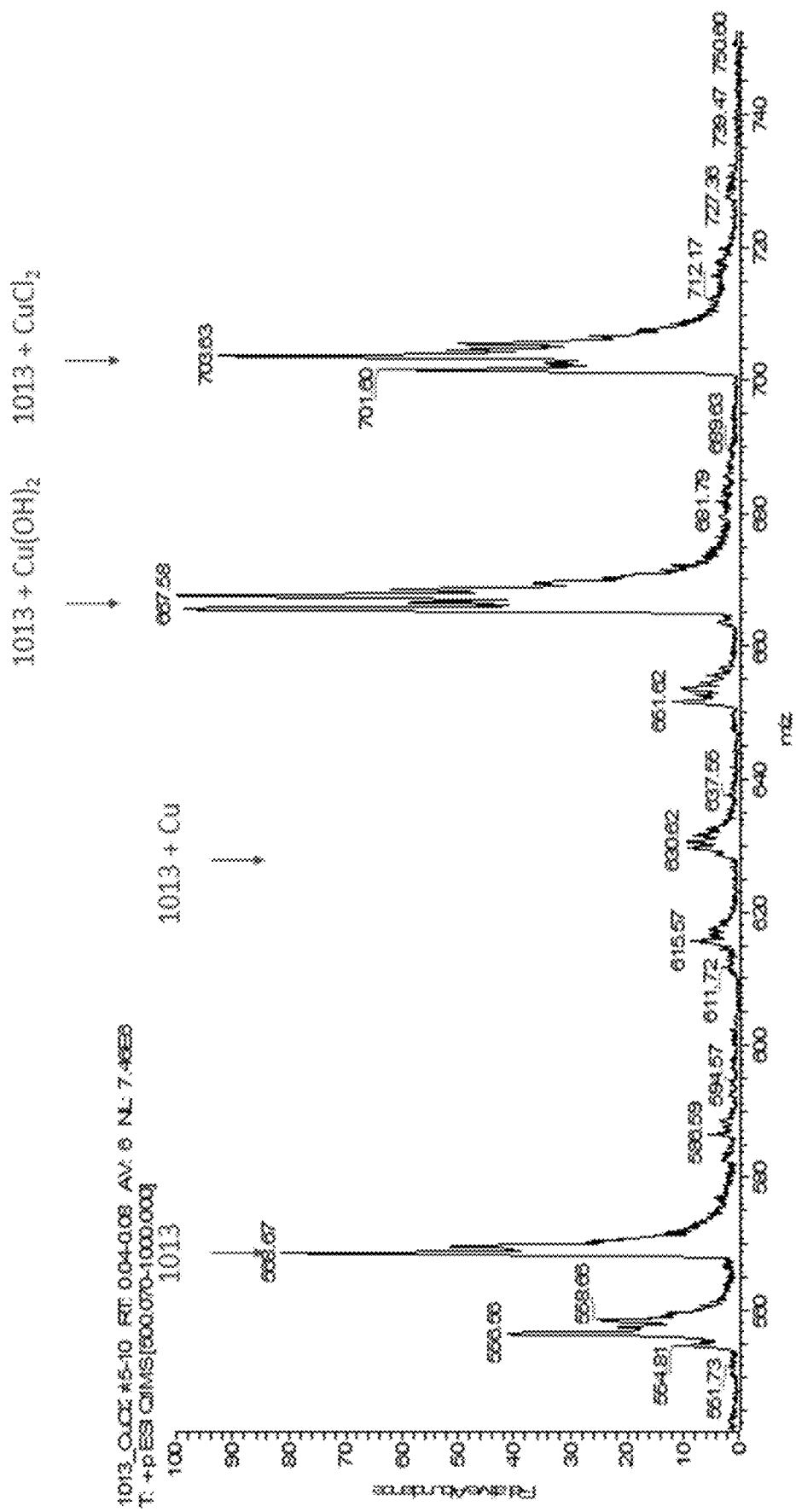

FIGS. 56A and 56B show DPM-1003 (1 mM) reacted with CuSO4 (8 mM) and CuCl$_2$ (8 mM), respectively, and the reaction mixture analyzed by ESI-MS.

DETAILED DESCRIPTION OF THE INVENTION

Disclosed herein are compounds that can form a complex with copper, or such compounds complexed with copper, and uses thereof. Such compounds may be in the form of a pharmaceutical composition, and may be administered to a patient in need of medical treatment. In some examples, administration of the compounds to a sample, such as a human or animal subject, a sample of biological tissue or cells, or an abiotic sample, in order to form a complex of the compounds with copper in the solution. For example, the compound may be used to chelate copper, so as to prevent or reduce the binding of copper to other molecules in the sample. In other examples, the compounds may be administered, with or without first being formulated as a complex with copper, such that a complex of the compound with copper, as administered or as formed upon administration of the compounds to a copper-containing sample, may have a therapeutic effect such as by binding to and inhibiting an enzyme. In some examples, an inhibitory effect of the compounds on enzymatic activity may be more long-lasting than an effect of the compounds may have on enzymatic activity when not complexed with copper.

As disclosed herein are compounds of Formula I:

wherein R is —OH or —O—CH$_3$. Such compounds are capable of forming a complex with copper. A compound of Formula I where R is —O—CH$_3$ is disclosed in U.S. Pat. No. 9,546,194, as an example of a compound that may inhibit the enzyme protein tyrosine phosphatase 1B (PTP1B). However, as disclosed herein, and not previously practiced or known, is the surprising finding that compounds of Formula I form a complex with copper with an affinity far above any affinity for binding other metal ions, with which compounds of Formula I do not form a complex. Furthermore, when complexed with copper, a compound of Formula I-copper complex can bind to and thereby inhibit the phosphatase activity of PTP1B. An inhibitory effect of a herein-disclosed compound-copper complex, such as compound of Formula I-copper complex, on enzymatic activity of PTP1B may be of a substantially longer duration than is accomplished by binding of the compound to PTP1B when the compound is not complexed with copper, or by the binding of structurally similar PTP1B inhibitors that do not form a complex with copper to PTP1B.

When administered to an animal or human subject, the chemical structure of a compound of Formula I may be altered by metabolic processing to form a metabolite. For example, —O—CH$_3$ at the R position may be altered to —OH at the R position by metabolic processing in the body. A compound of Formula I may form complexes with copper and can be used as copper-compound complexes or for the formation thereof whether R is —O—CH$_3$ or —OH, as further disclosed herein. Skilled artisans would appreciate that the hydroxyl hydrogen atom at position R may become dissociated from the compound under physiological conditions, or that a hydrogen atom may associate with a nitrogen elsewhere in the compound such as in the azaalkyl chain linked to the pyrimidine ring to form an internal acid, and that all such compounds would be included within Formula I of the present disclosure.

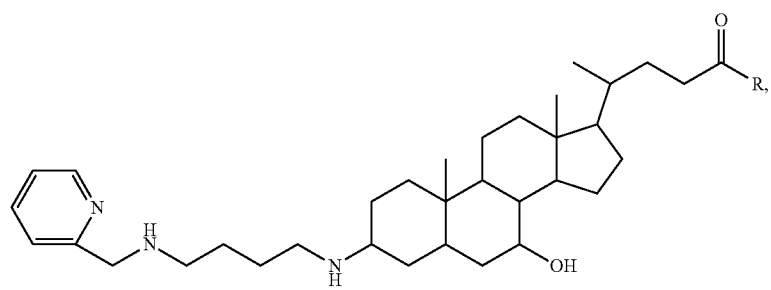

In some examples, Formula I may have the following structure:

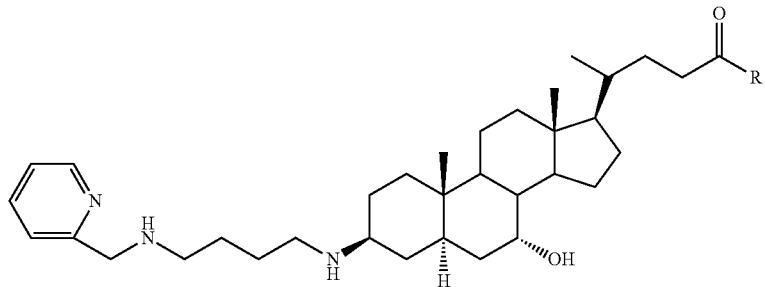

wherein R is —OH or —O—CH$_3$. When R is —O—CH$_3$, the compound is referred to herein as DPM-1001. When R is —OH, the compound is referred to herein as DPM-1011.

In other examples, Formula I may have the following structure:

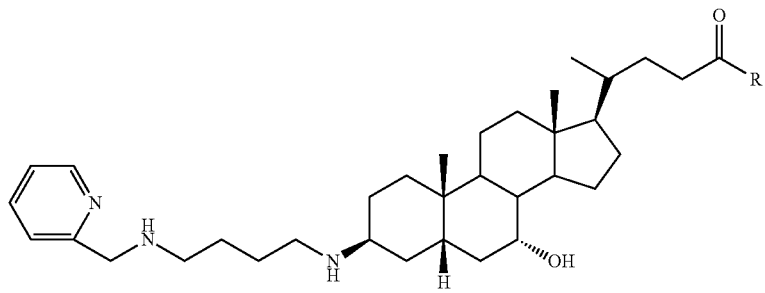

wherein R is —OH or —O—CH$_3$. When R is —O—CH$_3$, the compound is referred to herein as DPM-1013. When R is —OH, the compound is referred to herein as DPM-1015.

In other examples, Formula I may have the following structure:

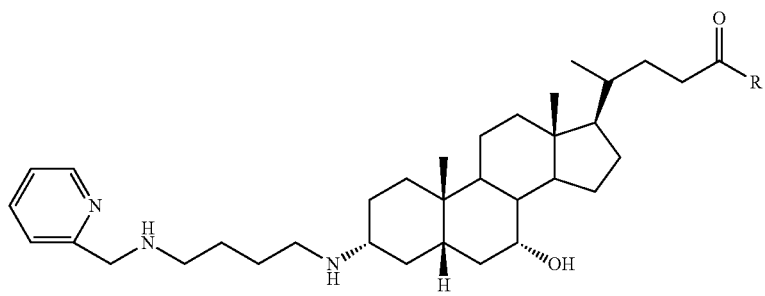

wherein R is —OH or —O—CH$_3$. When R is —O—CH$_3$, the compound is referred to herein as DPM-1014. When R is —OH, the compound is referred to herein as DPM-1016.

In other examples, Formula I may have the following structure:

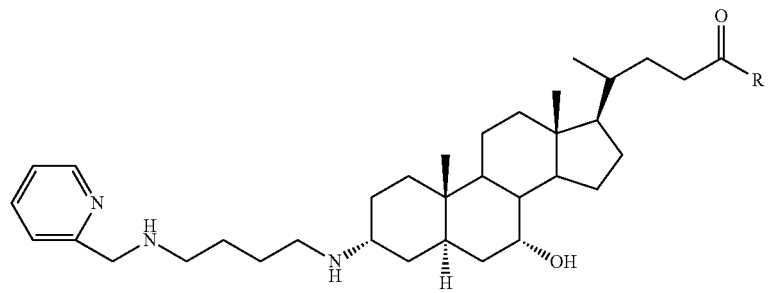

wherein R is —OH or —O—CH$_3$. In other examples, combinations of two or more of the foregoing and/or other stereoisomers of Formula I may be present in combination with each other, at varying relative proportions, some or all having R as —OH and some or all having R as —O—CH$_3$.

Other chemical structures closely related to compounds of Formula I do not form complexes with copper as also disclosed herein. For example, trodusquemine, also known as MSI-1436, or 3-N-1(spermine)-7,24-dihydroxy-5-cholestane 24-sulfate, is structurally related to DPM-1001. Despite the close structural similarity of DPM-1001 to MSI-1436, MSI-1436 does not form a complex with copper. Furthermore, like DPM-1001 as disclosed herein, MSI-1436 is capable of inhibiting enzymatic activity of PTP1B. However, as also disclosed herein, duration of inhibition of PTP1B enzymatic activity by Formula I compounds such as DPM-1001 complexed with copper is of a significantly longer duration than an inhibitory effect on PTP1B enzymatic activity of MSI-1436. MSI-1436 has been shown to be a reversible inhibitor of PTP1B. For example, whereas PTP1B activity recovers within 60 min or less when a sample containing PTP1B and MSI-1436 is diluted 100-fold, PTP1B activity remains inhibited following similar treatment of a sample containing PTP1B and a complex of DPM-1001 with copper for at least 240 min. Furthermore, a compound of Formula I has a surprisingly higher potency in inhibiting enzymatic activity of PTP1B, enhanced by pre-incubation of the compound with PTP1B. When a compound of Formula I such as DPM-1001 is pre-incubated with PTP1B it has a substantially higher potency (100 nm IC$_{50}$) than does MSI-1436 pre-incubated with PTP1B (600 nm IC$_{50}$). Thus, surprisingly, compounds of Formula I such as DPM-1001 complexed with copper are substantially more potent inhibitors of PTP1B with significantly longer duration of effectiveness than other compounds with similar chemical structures.

As further disclosed herein, a complex of a compound of Formula I such as DPM-1001 with copper was surprisingly found to have anti-tumor activities. MSI-1436 has previously been demonstrated to be toxic to certain types of breast tumor cells. Such effect of MSI-1436 may be related to an inhibitory effect of MSI-1436 on PTP1B activity in certain types of breast cancer cells. For example, some types of breast cancer cells express the protein HER2 (also known as receptor tyrosine-protein kinase erbB-2, CD340, proto-oncogene Neu, ERBB2), and expression of HER2 stimulates a cancer phenotype and tumor growth. PTP1B is over-expressed in certain HER2-positive breast cancer cells, and lack of PTP1B expression has been shown to prevent breast tumor development caused by over-expression of HER2. Accordingly, MSI-1436 is under investigation for use as treatment of cancer in patients with HER2$^+$ breast cancer.

However, a generalizable role of PTP1B in cancer per se, as opposed to in HER2+ breast cancer, is unknown. For some types of cells, unlike for HER2+ breast cancer cells, PTP1B inhibition promotes rather than inhibits a cancerous phenotype. Thus, an ability of a compound to inhibit tumor growth or the survival of tumor cells is not predictable merely on the basis of whether or not it inhibits PTP1B activity. And, given the relationship between HER2 expression and PTP1B activity in promoting tumor growth, one would not predict that a PTP1B inhibitor would inhibit tumor growth or survival of tumor cells for breast cancer cells that do not express HER2. For example, a compound referred to herein as DPM-1003 is identical to DPM-1001 except that the nitrogen atom of DPM-1003's pyrimidine ring is at the 3 position of the pyrimidine ring instead of at the 2 position of the pyrimidine ring. DPM-1003 can inhibit PTP1B (K$_i$ 2 µM). However, as disclosed herein, DPM-1003 does not inhibit the survival of triple-negative breast cancer cells, which are breast cancer cells that do not express HER2, and also do not express estrogen receptors or progesterone receptors. A lack of inhibitory effect of DPM-1003 on the survival of triple-negative breast cancer cells supports the conventional understanding that, for inhibition of PTP1B to decrease the survival of breast cancer cells or prevent tumor growth or reduce tumor size in breast cancer, the breast cancer cells must express HER2.

DPM-1003 and compounds of Formula I such as DPM-1001 differ from each other, however, in that DPM-1003 does not bind with high affinity to or form a complex with copper. As further disclosed herein, triple-negative breast cancer cells have elevated levels of intracellular copper, and elevated levels of copper transporters responsible for importation of copper into cells. As also disclosed herein, contacting triple-negative breast cancer cells with a compound of Formula I such as DPM-1001 reduces cellular copper levels, likely because of the compound's ability to bind copper with high affinity and form a complex therewith, or chelating copper, whereas contacting such cells with DPM-1003 does not reduce copper levels, likely because of DPM-1003's inability to bind copper with high affinity or form a complex therewith. Surprisingly, as disclosed herein, forming a compound-copper complex by contacting triple-negative breast cancer cells with a compound of formula I such as DPM-1001 potently inhibits survival of triple-negative breast cancer cells. Furthermore, forming a complex of a compound of Formula I with copper by administering DPM-1001 to mice with xenographic triple-negative breast cancer tumors shrank the size of such tumors, whereas administering DPM-1003 to such animals did not reduce tumor size or inhibit tumor growth. Whereas a lack of inhibitory effect of DPM-1003 on survival of HER2-negative breast cancer cells such as triple-negative breast cancer cells, nor on the growth of tumors of such cells, is not surprising, given the conventional understanding that an anti-cancer effect of inhibition of PTP1B activity in breast cancer would require expression of HER2 in the cancer cells, the disclosure herein of an inhibitory effect of forming a compound-copper complex by contacting triple-negative breast cancer cells with a compound of Formula I such as DPM-1001 was unexpected and not previously shown or performed. As further disclosed herein, forming a complex of a compound of Formula I such as DPM-1001 with copper by administering such compound to gastric cancer cells also inhibits survival of such cells. These effects suggest that DPM-1001 may be administered to treat cancer.

Chelation refers to the binding of a compound to a metal ion such that at the metal ion binds to the compound with high affinity and tends to form a complex with and remain bound to the compound rather than exist as a free metal ion in solution with the compound. A compound of Formula I chelates copper by binding to copper with high affinity and forming a complex therewith such that copper tends not to be released from the complex. Such a complex is formed at physiological conditions, such as when administered to cells in culture or to a mammalian animal such as a rodent, and would be formed when administered to a human subject, as disclosed herein. Such a complex of a compound of Formula I with copper is also formed in abiotic solutions, as also disclosed herein. An abiotic solution or sample is a sample that was not taken from a living subject or previously living subject and to which living cells or tissue or bodily fluids have not been purposefully added. An abiotic sample may be a solution from which copper removal may be desirable or measurement of copper levels may be desirable, but which was not taken from a living organism or previously living organism and to which living tissue or cells or bodily fluids have not been purposefully added. Though a sample may include trace, contaminant amounts of biological tissue, such as accidental trace amounts of cells or bodily fluids, skilled artisans would recognize that such a sample would be an abiotic sample or abiotic solution if it had not been drawn or taken from a living subject or to which tissue or cells or bodily fluids taken from a living subject had been added or to which or in which cultured cells had been added or grown.

As further disclosed herein, the formation of a complex of a compound of Formula I such as DPM-1001 with copper may inhibit enzymatic activity of various kinases. Because DPM-1001 can form a complex with copper, and because it can reduce copper levels in cells, presumably by forming a complex with cellular copper, administering a compound of Formula I to cells may chelate copper in such cells and prevent or reduce copper's binding to other cellular molecules. If copper binding is important for the functions of such molecules, then contacting such cells with such copper-binding compounds and forming a complex thereof with copper would be predicted to inhibit the activity of such molecules. As further disclosed herein, numerous kinase enzymes bind copper. For example, as disclosed herein, pyruvate kinase M (PKM), mitochondrial adenylate kinase 2 (AK2), creatine kinase B (CKB), p21-activated kinase (PAK), TP53-regulating kinase (TP53RK), phosphoglycerate kinase 1 (PGK1), pyridoxal kinase (PDXK), mitochondrial creatine kinase U-type (CKMT1B), mitogen-activated protein kinase kinase (MEK), and tyrosine kinase CSK all bind copper.

As further disclosed herein, binding of copper promotes kinase activity of PAK. For example, exposing triple-negative breast cancer cells to elevated levels of copper leads to elevated levels of phosphorylated PAK, and phosphorylated targets and signaling molecules downstream of PAK in a PAK-activated signaling cascade, such as an increase in phosphorylated c-Raf and an increase in phosphorylated Bad, indications of increased PAK kinase activity caused by increased PAK-binding to copper. Phosphorylation of Bad promotes cell survival by preventing Bad from effecting pro-apoptotic functions. Thus, increased copper binding to PAK causing increased PAK activity promotes cell survival be reducing phosphorylation, and reducing inactivation, of Bad. Given the elevated copper levels in triple-negative breast cancer cells, copper may promote survival of triple-negative breast cancer cells by stimulating activity of a PAK-signaling cascade and thereby inhibiting apoptosis and cell death of such cancer cells. As further disclosed herein, forming a complex of a compound of Formula I with copper by administering DPM-1001, for example, to triple-negative breast cancer cells, thereby cheating copper and preventing copper from binding to and increasing the activity of PAK, reduces activity of PAK, and thereby inhibits survival of triple-negative breast cancer cells.

As further disclosed herein, copper binds MEK. Aberrant activity of MEK and of the Ras-mitogen-activated protein kinase (MAPK) signaling cascade whose activity MEK stimulates has been linked to various cancers. Increase MEK and Ras-MAPK activity can stimulate cancer cell survival and promote cellular proliferation and cellular migratory functions related to metastasis. Thus, inhibition of MEK and the Ras-MAPK cascade is protective against some forms of cancer. For example, in some, but not all, forms of triple-negative breast cancer, treatment with AZD6244 (also known as selumetinib, or 6-(4-bromo-2-chloroanilino)-7-fluoro-N-(2-hydroxyethoxy)-3-methylbenzimidazole-5-carboxamide), a MEK inhibitor, inhibits cell survival. As disclosed herein, in triple-negative breast cancer cells treated with AZD6244 at concentrations at which such treatment does not inhibit cancer cell survival, forming in such cells a complex of a compound of Formula I and copper by administering DPM-1001, at a concentration of that does not inhibit cancer cell survival on its own, s significantly inhibits cancer cell survival. In other words, as disclosed herein, administering a dose of AZD6244 to a triple-negative breast cancer cell that does not inhibit cell survival when administered on its own, together with a dose of DPM-1001 that does not inhibit cell survival on its own, inhibits cell survival of triple-negative breast cancer cells. Administering a compound of Formula I to such cells would form a compound-copper complex, such as by chelating cellular copper, reducing the amount of copper available for binding to MEK. Thus, as disclosed herein, forming a complex of a compound of Formula I with coper by administering such a compound such as DPM-1001 may be protective against cancer by inhibiting activity of MEK and the Ras-MAPK signaling pathway, and may therefore be a treatment for such cancers. Furthermore, compounds of Formula I may be be an adjunct to treatment with AZD6244. For example, triple-negative breast cancer cells that are non-responsive to AZD6244, or which may have become resistant to treatment with AZD6244 because of prior administration of AZD6244, or which have been identified as non-responsive to AZD6244 because of lack of effectiveness of prior administration of AZD6244, formation of a complex of a compound of Formula I with copper such as by administering DPM-1001 to a patient harboring such cells may be a treatment for such cancer.

As further disclosed herein, chelating copper with a compound of Formula I may be protective against cancers caused by dysregulation of the Ras-MAPK pathway caused by mutations of the kinase B-Raf, or BRAF. BRAF activates the Ras-MAPK cascade, and mutations of BRAF prevalent in many forms of cancer (such as BRAF V600E) lead to enhanced MEK phosphorylation and increased activity of the Ras-MAPK pathway in tumor cells. Such BRAF-mediated increased activity and tumorigenesis is dependent on copper, in that such tumorigenic effects of mutated BRAF (such as V600E BRAF) are diminished in cells lacking copper transporters responsible for permitting copper entry into cells, and in cells expressing a mutated form of MEK that cannot bind copper. Furthermore, the tumorigenic effects of V600E BRAF are inhibited by treatment of cells with copper chelators. Furthermore, treatment of some cancer cells with BRAF inhibitors such as, for example, vemurafenib (N-[3-[5-(4-chlorophenyl)-1H-pyrrolo[2,3-b]pyridine-3-carbonyl]-2,4-difluorophenyl]propane-1-sulfonamide) can inhibit tumor growth, but some such cells develop a resistance to vemurafenib, such that prior treatment with vemurafenib leads to mutations which render the cells insensitive to the anti-tumor effects of vemurafenib. However, treatment of such cells with copper chelators reduced tumor growth, notwithstanding development of mutations that permitted escape from the antitumor effects of BRAF inhibition. Thus, as disclosed herein, chelating copper by treatment with a compound of Formula I and forming a complex of, for example, DPM-1001 with cellular copper may be a treatment for types of cancer typified by disrupted BRAF signaling such as tumors expressing BRAF V600E or similar mutations of valine 600 in BRAF. Similarly, such treatment with a compound of Formula I may be effective as an adjunctive therapy with BRAF inhibitors (such as vemurafenib or others including for example dabrafenib, a.k.a. N-[3-[5-(2-aminopyrimidin-4-yl)-2-tert-butyl-1,3-thiazol-4-yl]-2-fluorophenyl]-2,6-difluorobenzenesulfonamide), or prevent development of resistance to BRAF inhibitors by hastening death of tumor cells before treatment with a BRAF inhibitor is capable of resulting in generation of mutations that confer BRAF resistance.

As further disclosed herein, forming a complex of a compound of Formula I with copper by administering, for example, DPM-1001 may inhibit angiogenesis. Angiogenesis is important for the survival of many types of tumors, and suppression of angiogenesis can deprive tumor cells of the blood, oxygen, and nutrient supply required for tumor cell survival, tumor cell growth, or metastasis. Copper is also known to be important for angiogenesis. Thus, administration of copper chelators is known to be protective against some forms of cancer by inhibiting angiogenesis. As disclosed herein, copper may be chelated by administering to a subject a compound of Formula I and forming a complex of, for example, DPM-1001, and copper, thereby preventing angiogenesis in such subject and preventing tumor growth, promoting tumor shrinkage, or preventing metastasis.

As further disclosed herein, forming a complex of a compound of Formula I with copper by administering to a sample or subject DPM-1001, for example, may be protective against conditions or disorders which are typified or involve pathologically high levels of copper. For example, Wilson's disease involves an accumulation of copper in the body and chronic, cytotoxic accumulation of copper in bodily tissues and elevated physiological levels of copper relevant t such levels in subject who do not have Wilson's disease. As skilled artisans would recognize, cytotoxic effects are effects that cause cell death or would be predicted to cause cell death if persistent for a prolonged period of time. Symptoms of Wilson's disease include cirrhosis of the liver, hemolytic anemia, neurologic abnormalities, and corneal opacities. Also, copper toxicity can occur from exposure to excess environmental copper, such as high levels in drinking water, or cooking foods high in acid content in un-coated copper cookware. Symptoms may include gastrointestinal distress, such as vomiting, vomiting of blood, or melena, hypotension, jaundice, or coma. Chronic pathologically high copper retention may result in neural, kidney, or liver tissue damage. Copper chelation may be used to treat such conditions or symptoms resulting from elevated bodily copper levels. As disclosed herein, forming a complex of a compound of Formula I, such as by administering, for example, DPM-1001 to an individual or cell or tissue type with or exhibiting elevated levels of copper and thereby chelating copper in such subject or sample can prevent, treat, or reduce the cytotoxic or other deleterious effects of such elevated copper.

Cells taken from patients with Wilson's disease to elevate show higher susceptibility to the cytotoxic effects of elevated copper exposure than do cells taken from people who do not have Wilson's disease, but administering DPM-1001 prevents such cytotoxic effects. Furthermore, in an animal model of Wilson's disease, the toxic milk mouse model (TX), in which TX mice retain and accumulate excessive bodily and tissue copper levels due to a mutation of a copper transporter responsible for copper excretion, TX mice do not live as long as non-TX mice, and TX mice accumulate high levels of copper in various bodily tissues, including liver and brain. Liver tissue of TX mice also exhibit morphological abnormalities, such as enlarged hepatocytes with irregular shape and arrangement, as well as large cytoplasmic lipid droplets, and elevated expression of mettalothionein, a metal-binding protein. However, as demonstrated herein, treating TX mice with DPM-1001 (5 mg/kg, every third day) prolongs their life, inhibits copper accumulation in liver and brain, prevents elevated metallothionein expression in liver, and prevents the enlarged hepatocytes with irregular shape and arrangement large cytoplasmic lipid droplets in liver.

By contrast, treatment of TX mice with DPM-1003, which does not bind copper with high affinity, did not affect levels of copper in liver tissue. Another copper chelator, tetrathiomolybdate (TTM), also prevented accumulation of copper in liver and brain of TX mice (treated with 5 mg/kg, intraperitoneally, daily), but caused accumulation of copper in the kidney, related perhaps to its promotion of copper excretion. In contrast, treating TX mice with DPM-1001 (5 mg/kg, orally, every third day) does not promote accumulation of copper in the kidney, apparently causing elimination of copper via egestion through the digestive tract, as demonstrated by elevated copper levels in feces of TX mice treated with DMP-1001 compared to TX mice treated with TTM or TX mice not treated with DPM-1001. Compounds of Formula I may therefore be administered for use as treatment for patients with Wilson's disease or other copper toxicities to chelate bodily copper and treat the symptoms, diseases, or syndromes, caused by excessive copper exposure, and may be preferable to her copper chelators for such purposes because of the relatively lower doses needed and fecal excretion rather than kidney accumulation.

In other examples, forming a complex of a compound of Formula I with copper by administering it to a sample or subject may be used to affect actions of various hormones involved in glucose and energy metabolism, such as insulin and leptin, and as a treatment for conditions or disorders related to pathological or imbalanced activity of such physiological processes, such as diabetes, hyperglycemia, or obesity. Similarly, administering a pharmaceutical composition that includes a complex of a compound of Formula I with copper to a sample or subject may also be used to affect actions of various hormones involved in glucose and energy metabolism, such as insulin and leptin, and as a treatment for conditions or disorders related to pathological or imbalanced activity of such hormones, such as diabetes, hyperglycemia, or obesity.

For example, inhibition of PTP1B activity has been identified as method of treatment for diabetes, promote insulin and leptin sensitivity, normalize blood glucose levels, and treat obesity. As described herein, including above, compounds of Formula I complexed with copper are potent inhibitors of PTP1B activity with long-lasting inhibitory effects. As disclosed herein, in an animal model of obesity and insulin and leptin resistance, mice fed a high fat diet were administered DPM-1001 (5 mg/kg, either orally or intraperitoneally) lost approximately 5% of their body weight (without weight loss in mice not fed a high-fat diet), showed a lower rise in blood glucose levels in response to injection with glucose, and enhanced the effect of insulin to reduce blood glucose levels, indicating enhanced insulin signaling cause by DPM-1001 treatment. Administering DPM-1001 (whether orally or intraperitoneally) also increased insulin-stimulated insulin receptor phosphorylation in mice, as well as phosphorylation of AKT, both indications of increased reactivity to insulin caused by DPM-1001 treatment, as well as increased leptin-induced JAK2 phosphorylation in mouse hypothalamus, indicating increased responsiveness of leptin receptor signaling to leptin caused by treatment with DPM-1001. Patients who have been diagnosed with diabetes, hyperglycemia, or obesity may therefore be treated with a compound of Formula I complexed with copper, such as by administering to them DMP-1001 to form a complex with copper present in the subject, or by administering a pharmaceutical composition including a compound of Formula I such as DPM-1001 complexed with copper, to promote proper insulin and leptin function and signaling, maintain healthy blood glucose levels, and reduce or prevent obesity.

For example, such treatment may reduce a subject's Body Mass Index, calculated as body mass divided by the square of the body height, and may be expressed in units of $kg/m^2$. A compound or pharmaceutical composition including a compound of Formula I, optionally complexed with copper or administered in order to form in the body a complex with copper, may be administered to a person whose Body Mass Index is between 25 to 30, which may be generally characterized as overweight, or above 30, which may be generally characterized as obese, to reduce their Body Mass Index. Such compound or pharmaceutical composition may also be administered to a person with a Body Mass Index below 25 to promote physiologically appropriate insulin signaling, leptin signaling, or to lower Body Mass Index or to prevent increased Body Mass Index.

Furthermore, some diabetes patients exhibit elevated copper levels. Similar to patients with Wilson's disease, elevated copper levels in diabetic patients can have cytotoxic effects and cause tissue or organ damage or dysfunction. The aforementioned method of treating patients having elevated copper levels by administering a compound of Formula I and thereby form a complex of such compound with copper, is also applicable to treatment of patients with diabetes. By administering a compound of Formula I, such as DPM-1001, to such patients, a complex may be formed between such compound and copper, such as by chelating bodily copper, thereby lowering copper levels and preventing cytotoxic or other untoward effects of pathologically high copper levels found in such patients.

Also disclosed herein is a pharmaceutical composition that includes a compound of Formula I in a complex with copper. In some examples, such a pharmaceutical composition may include pharmaceutically-acceptable excipients consistent with formulation of such pharmaceutical composition, and as may formulated for most efficacious administration of said pharmaceutical composition to promote such formulation.

As disclosed herein, DPM-1001 binds copper with a Kd of 75 nM and a stoichiometry of 1 mol/mol. A complex with copper means binding copper with a Kd of under 100 nM, and includes binding copper with a Kd of 75 nM, with Kd measured as described herein in the EXAMPLES. A pharmaceutical composition including a compound of Formula I complexed with copper includes, as a non-limiting example, such compound in a lyophilized or dry form with copper ions such that dissolving such dry for in solvent, including upon oral administration to a subject, such compound would bind with copper as administered therewith in solution with a Kd of 100 nM or less.

Formulations for administration to a subject include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of a recipient or intended purpose of the administration. A formulation may conveniently be presented in unit dosage form and may be prepared by any of the methods well known in the art of pharmacy. Methods may include a step of bringing into association a compound of Formula I or a pharmaceutically acceptable salt thereof ("active ingredient") with a carrier which constitutes one or more accessory ingredients. In general, formulations may be prepared by uniformly and intimately bringing into association an active ingredient with liquid carriers or finely divided solid carriers or both and then, if necessary, shaping the product into the desired formulation.

Formulations of the present disclosure suitable for oral administration may be presented as discrete units such as capsules, cachets or tablets each containing a predetermined amount of an active ingredient; as a powder or granules; as a solution or a suspension in an aqueous liquid or a non-aqueous liquid; or as an oil-in-water liquid emulsion or a water-in-oil liquid emulsion. A compound of Formula I may also be presented as a bolus, electuary or paste. For oral or other administration, a compound of Formula I may be suspended in a solution, or dissolved in a solvent, such as alcohol, DMSO, water, saline, or other solvent, which may be further diluted or dissolved in another solution or solvent, and may or may contain a carrier or other excipient in some examples.

In certain embodiments, a compound of Formula I may be incorporated with excipients and used in the form of ingestible tablets, buccal tablets, troches, capsules, elixirs, suspensions, syrups, wafers, and the like. Tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

A tablet may be made by compression or molding, optionally with one or more accessory ingredients. Compressed tablets may be prepared by compressing in a suitable machine an active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. Tablets may optionally be coated or scored and may be formulated so as to provide sustained, delayed or controlled release of an active ingredient therein.

A compound of Formula I may applied to any sample in which binding to or chelation of copper is desirable, or in which inhibition of enzymatic activity as disclosed herein is desired, or in which it may be desirable to test a potential role or importance of copper's availability. A sample may include, as described above, an abiotic sample. Or it may be a sample of cells, tissue, or bodily fluids taken or harvested from a living organism or previously living organism. A sample could also include a subject meaning an organism, including a human or nonhuman animal. For example, a subject may include a human or nonhuman animal in need of medical treatment. A sample could also include a biological solution, a suspension of biological material, or tissue, such as a solution or suspension of components taken from living cells or previously living cells, or from culture or tissue medial in which living cells or tissue were cultured, or may include bodily fluids, such as blood, saliva, cerebrospinal fluid, ascites, lymph, plasma, serum, mucous, or other bodily fluids or secretions. A biological sample could be a solution or suspension of organic molecules or other compounds produced by living cells. A sample that contains organic molecules synthesized other than by living cells, tissue, or organisms, such as by man-made methods, including synthetic copies of otherwise naturally occurring compounds, would not constitute a biological solution or suspension.

Formulations for parenteral or other administration include aqueous and non-aqueous sterile injection solutions which may contain anti-oxidants, buffers, bacteriostats and solutes which render a formulation isotonic with the blood of the intended recipient. Formulations for parenteral or other administration also may include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of a compound of Formula I to polymer and the nature of the particular polymer employed, the rate of a compound of Formula I release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

A compound of Formula I formulation may include different types of carriers depending on whether it is to be administered in solid, liquid or aerosol form, and whether it needs to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990.

The term "pharmaceutically acceptable salt" refers to salts prepared from pharmaceutically acceptable non-toxic acids or bases including inorganic acids and bases and organic acids and bases. Unless otherwise specified, reference herein to a compound of Formula I, or to any such compound in particular, includes reference to a pharmaceutically acceptable salt thereof. When the compounds of the present disclosure are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

A compound of Formula I may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of Burger's Medicinal Chemistry And Drug Discovery, 5 th Edition, Vol 1: Principles and Practice.

As used herein, the term "effective amount" means an amount of a compound of Formula I pharmaceutical agent that may elicit a biological or medical response of a cell, tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts, solvates, and physiological functional derivatives thereof, may be administered as the raw chemical. Additionally, the active ingredient may be presented as a pharmaceutical composition.

Pharmaceutical compositions of the present invention include an effective amount of a compound of Formula I and optionally one or more additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains a compound of Formula I and optionally one or more additional active ingredient will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

Further in accordance with the present invention, the composition of the present invention suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, a compound of Formula I may be combined with a carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of pharmaceutical lipid vehicle compositions that include a compound of Formula I and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, a compound of Formula I may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to a subject (e.g., an animal or human patient) can be determined by physical and physiological factors such as body weight, severity of condition, the type of disease being treated, previous or concurrent therapeutic interventions, idiopathy of the patient and on the route of administration, and purpose of treatment. Depending upon the dosage and the route of administration, the number of administrations of a preferred dosage and/or an effective amount may vary according to the response of the subject or purpose of treatment. The practitioner responsible for administration will, in any event, determine the concentration of active ingredient(s) in a composition and appropriate dose(s) for the individual subject.

In certain embodiments, pharmaceutical compositions may include, for example, at least about 0.1% of an active compound. In other embodiments, an active compound may comprise between about 2% to about 75% of the weight of the unit, or between about 25% to about 60%, for example, and any range derivable therein. Naturally, the amount of a compound of Formula I in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one of ordinary skill in the art of preparing such pharmaceutical formulations, and as such, a variety of dosages and treatment regimens may be desirable.

In other non-limiting examples, a dose may also comprise from about 1 microgram/kg body weight, about 5 microgram/kg body weight, about 10 microgram/kg body weight, about 50 microgram/kg/body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above.

Dosing can be modified or chosen based on factors including purpose of treatment, severity of symptoms, or an individual subject's body mass. A daily dose may be administered once per day, or distributed over 2, 3, 4, 5, 6, 7, 8, or more administrations per day. A daily dose me be between 10 mg and 20 g per day. A daily dose may be less than 10 mg, for example 5 mg or 1 mg per day, or in a range of between 1-5 mg or between 5-10 mg. A daily dose may be between 10 mg and 50 mg, or between 50 mg and 100 mg, or between 100 mg and 150 mg, or between 150 mg and 200 mg, or between 200 mg and 250 mg, or between 250 mg and 300 mg, or between 300 mg and 350 mg or between 350 m and 400 mg or between 400 mg and 450 mg or between 450 mg and 500 mg. A daily dose may be between 500 mg and 600 mg, or between 600 mg and 700 mg, or between 700 mg and 800 mg, or between 900 mg and 1 g, or between 1 g and 1500 mg, or between 1500 mg and 2 g, or between 2 g and 2500 mg, or between 2500 mg and 3 g, or between 3 g and 3500 mg, or between 3500 mg and 4 g, or between 4 g and 4500 mg, or between 4500 mg and 5 g. A daily dose may be between 5 g and 6 g, or between 6 g and 7 g, or between 7 g and 8 g, or between 8 g and 9 g, or between 9 g and 10 g, or between 10 g and 11 g, or between 11 g and 12 g, or between 12 and 13 g, or between 13 g and 14 g, or between 14 g and 15 g, or between 15 g and 16 g, or between 16 g and 17 g, or between 17 g and 18 g, or between 18 g and 19 g, or between 19 g and 20 g. Al subranges within and between any of these ranges are also included within the present disclosure.

In some embodiments, a compound of Formula I may be formulated to be administered via an alimentary route. Alimentary routes include all possible routes of administration in which the composition is in direct contact with the alimentary tract. Specifically, a compound of Formula I may be administered orally, buccally, rectally, or sublingually. As such, a compound of Formula I may be formulated with an inert diluent or with an assimilable edible carrier, or may be enclosed in hard- or soft-shell gelatin capsule, or may be compressed into tablets, or may be incorporated directly with the food of the diet.

For oral administration a compound of Formula I may alternatively be incorporated with one or more excipients in the form of a mouthwash, dentifrice, buccal tablet, oral spray, or sublingual orally-administered formulation. For example, a mouthwash may be prepared incorporating a compound of Formula I in the required amount in an appropriate solvent, such as a sodium borate solution (Dobell's Solution). Alternatively, a compound of Formula I may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively a compound of Formula I may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, a compound of Formula I may be administered via a parenteral route. As used herein, the term "parenteral" includes routes that bypass the alimentary tract. Specifically, a compound of Formula I may be administered for example, but not limited to intravenously, intradermally, intramuscularly, intraarterially, intrathecally, subcutaneous, or intraperitoneally.

Solutions of a compound of Formula I as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form may be sterile and fluid to the extent that easy injectability exists. A carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution may be suitably buffered if necessary and a liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, general safety and purity standards as required by FDA Office of Biologics standards.

Sterile injectable solutions may be prepared by incorporating a compound of Formula I in the required amount in the appropriate solvent with various of the other ingredients enumerated above, as required, followed by filtered sterilization. Generally, dispersions may be prepared by incorporating various sterilized active ingredients into a sterile vehicle which contains the basic dispersion medium and the required other ingredients from those enumerated above. In the case of sterile powders for the preparation of sterile injectable solutions, preferred methods of preparation include vacuum-drying and freeze-drying techniques which yield a powder of the active ingredient plus any additional desired ingredient from a previously sterile-filtered solution thereof. A powdered composition may be combined with a liquid carrier such as, e.g., water or a saline solution, with or without a stabilizing agent.

In other embodiments a compound of Formula I may be formulated for administration via various miscellaneous routes, for example, topical (i.e., transdermal) administration, mucosal administration (intranasal, vaginal, etc.) and/or inhalation.

Pharmaceutical compositions for topical administration may include a compound of Formula I formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described. Likewise, the delivery of drugs using intranasal microparticle resins and lysophosphatidylglycerol compounds are also well-known in the pharmaceutical arts. Likewise, transmucosal drug delivery in the form of a polytetrafluoroetheylene support matrix may be adopted for use in accordance with the present disclosure.

The term aerosol refers to a colloidal system of finely divided solid of liquid particles dispersed in a liquefied or pressurized gas propellant. An aerosol of the present invention for inhalation may consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

The following examples are intended to illustrate particular embodiments of the present disclosure, but are by no means intended to limit the scope thereof.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

Synthesis of a Compound of Formula I

In general, compounds disclosed herein may be prepared by the methods illustrated in general reaction schemes as, for example, described below, or by modifications thereof, using readily available starting materials, reagents and conventional synthesis procedures. In these reactions, it is also possible to make use of variants that are in themselves known, but are not mentioned here. The starting materials are either commercially available, synthesized as described in the examples or may be obtained by the methods well known to persons of skill in the art. Reference is made to synthesis methods and materials disclosed elsewhere and well-known to skilled artisans, such as in Dolle et al., 1993, Tetrahedron 49:2485-2498.

As one example, a compound of Formula I may be synthesized according to the following synthesis schemes:

Preparation of 1

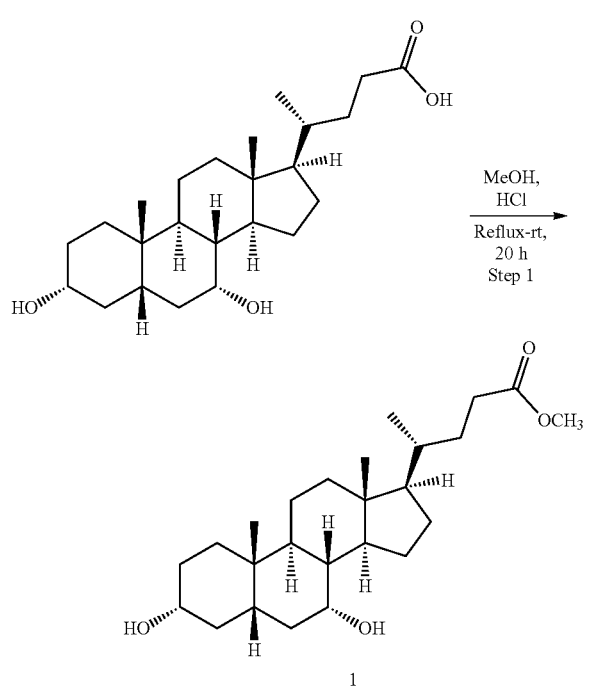

A mixture 5β-cholanic acid-3α-7α-diol (25.0 g, 63.7 mmol) and conc. HCl (37%, 7 mL) in MeOH (50 mL) heated at reflux for 10 min and then stirred at room temperature overnight. The mixture was diluted with EtOAc (1 L), washed twice with 10% aq. NaOH solution (2×200 mL), water (2×200 mL) and brine (50 mL). The organic layer was dried over anhydrous Na₂SO₄, filtered and evaporated to yield 1 (25.7 g, 99%) as a white foam. The crude product was used directly in the next step without further purification. TLC: Rf=0.6 (silica gel, EtOAc:hexanes, 50:50).

1H-NMR (300 MHz, CDCl₃) δ 3.84 (m, 1H, H-7), 3.65 (s, 3H, OCH₃), 3.50-3.40 (m, 1H), 2.42-2.29 (m, 1H), 2.28-2.23 (m, 2H), 2.02-1.58 (m, 8H), 1.54-0.98 (m, 17H), 0.92 (d, J=6.6 Hz, 3H, H-21), 0.89 (s, 3H, H-19), 0.64 (s, 3H, H-18).

Preparation of 2

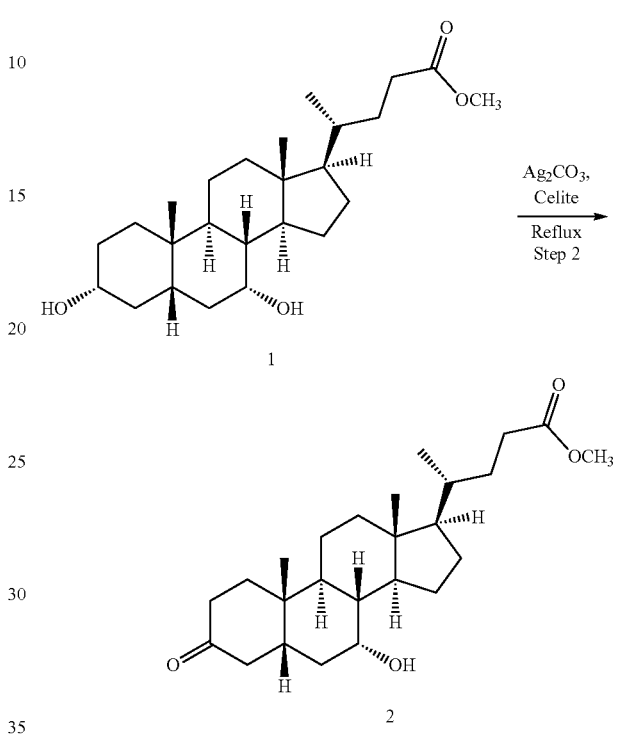

A suspension of Ag₂CO₃/Celite (25 g, 50 wt %, 45.33 mmol) in toluene (300 mL) was heated at reflux in a three-neck round bottom flask connected to a Dean-Stark apparatus for 30 min and allowed to cool to room temperature. A solution of 1 (8.72 g, 21.4 mmole) in toluene was added dropwise over 40 min and the resultant mixture was heated at reflux for 4 h while removing water via the Dean-Stark apparatus. The mixture was allowed to cool to room temperature, filtered through a pad of Celite, and washed with EtOAc. The filtrate was evaporated and dried under vacuum to get 2 (8.51 g, 98%) as a white foam. TLC: Rf=0.5 (silica gel, EtOAc:hexanes, 30:70). 1H-NMR (300 MHz, CDCl₃) δ 3.95 (m, 1H, H-7), 3.65 (s, 3H, OCH₃), 3.44 (m, 1H, H-4a), 2.45-2.28 (m, 2H), 2.25-1.50 (m, 11H), 1.48-1.10 (m, 14H), 1.00 (s, 3H, H-19), 0.93 (d, J=6.4 Hz, 3H, H-21), 0.69 (s, 3H, H-18).

Preparation of 3

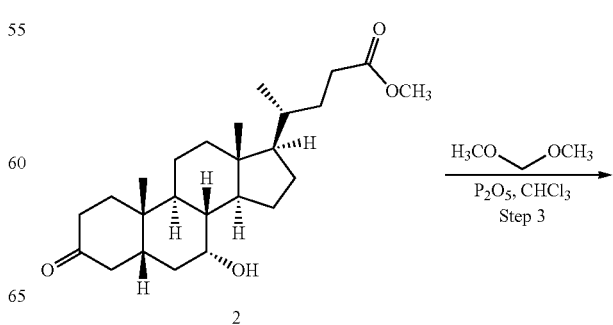

-continued

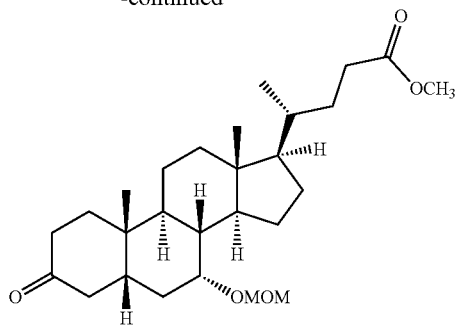

3

To a mixture of 2 (2.0 g, 4.94 mmol) and dimethoxymethane (4.51 g, 59.1 mmol) in anhydrous $CHCl_3$ (200 mL) at 0° C. under nitrogen was added $P_2O_5$ portionwise (7.53 g) via a solid addition funnel over 30 min. The resulting mixture was stirred at room temperature for 3 h. The mixture was decanted into ice-water (500 mL), the organic phase was separated and the aqueous phase was extracted with $CHCl_3$ (2×100 mL). The combined organic layers were washed with 1 M HCl (50 mL), water (100 mL), brine and dried over anhydrous $Na_2SO_4$ and then evaporated and dried under vacuum. The crude product was purified by silica gel flash chromatography by eluting with 5-30% EtOAc hexanes to give 3 (1.18 g, 53%) as a pale yellow solid. TLC: Rf=0.7 (silica gel, EtOAc:hexanes, 30:70). 1H-NMR (300 MHz, $CDCl_3$) δ 4.60 (d, J=6.8 Hz, 2H, —$OCH_2O$—), 3.71-3.62 (m, 4H, $OCH_3$ and H-7), 3.36 (s, 3H, $OCH_3$), 3.34-3.28 (m, 1H, H-4a), 2.46-2.30 (m, 2H), 2.28-2.04 (m, 3H), 2.26-1.62 (m, 8H), 1.58-1.04 (m, 11H), 1.0 (s, 3H, H-19), 0.93 (d, J=6.4 Hz, 3H, H-21), 0.67 (s, 3H, H-18).

Preparation of 4

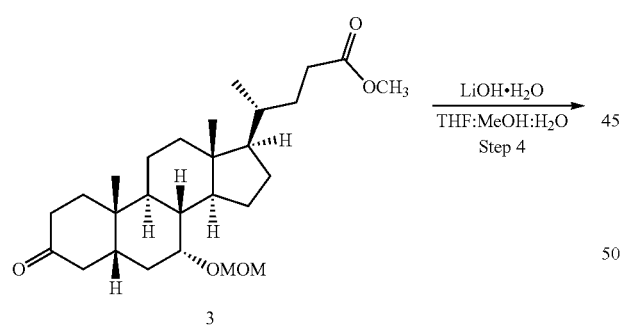

To a solution of 3 (2.5 g, 5.57 mmol) in a mixture of THF:MeOH:$H_2O$ (3:1:1, 25 mL) was added LiOH.$H_2O$. The mixture was stirred at ambient temperature over the weekend. The mixture was then diluted with EtOAc (200 mL), washed with 0.1 N HCl, water, brine and dried ($Na_2SO_4$) and then filtered and evaporated to give 4 (2.39 g, 98%) as a white foam. TLC: Rf=0.25 (silica gel, EtOAc:hexanes, 40:60). 1H-NMR (300 MHz, $CDCl_3$) δ 4.60 (d, J=6.8 Hz, 2H, —$OCH_2O$—), 3.69-3.64 (m, 1H, H-7), 3.36 (s, 3H, $OCH_3$), 3.34-3.26 (m, 1H, H-4a), 2.46-2.09 (m, 5H), 2.08-1.06 (m, 23H), 1.01 (s, 3H, H-19), 0.95 (d, J=6.4 Hz, 3H, H-21), 0.68 (s, 3H, H-18). APCI-=433.

Preparation of 5

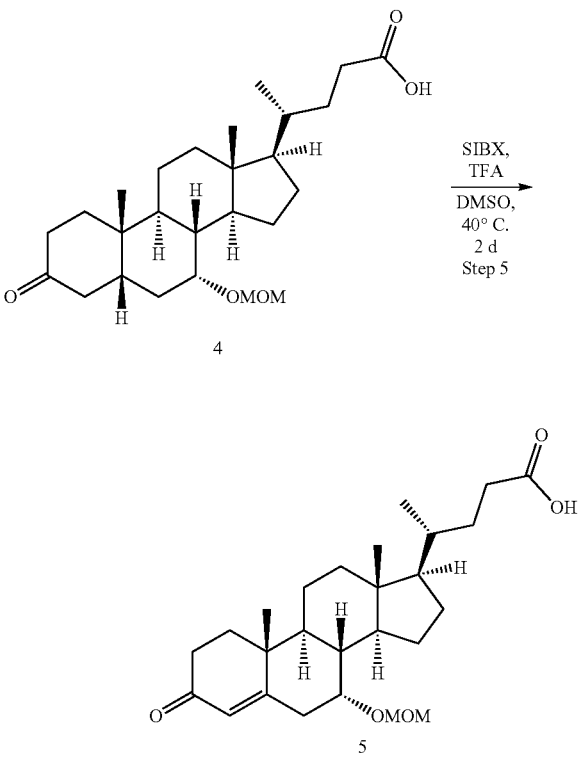

To a solution of 4 (2.38 g, 5.48 mmol) in DMSO (200 mL) was added SIBX (4.8 g, 7.71 mmol) portionwise followed by TFA (130 µL) at room temperature. This mixture was stirred at 40° C. for 2 d. The reaction mixture was cooled to room temperature, added water (1 L) and extracted with EtOAc (4×200 mL). The combined organic layer was washed with water, brine, dried over anhydrous $Na_2SO_4$ and concentrated on a rotary evaporator to give a solid. To the solid was added $CH_2Cl_2$ (300 mL) and filtration removed the undissolved white solid. The filtrate was evaporated and the residue purified by silica gel flash chromatography eluting with 15-50% EtOAc:hexanes to give 5 (830 mg, 35%) as a white solid. TLC: Rf=0.3 (silica gel, EtOAc:hexanes, 50:50). 1H-NMR (300 MHz, $CDCl_3$) δ 5.71 (s, 1H, H-4), 4.63 (dd, J=12.6, 6.9 Hz, 2H, —$OCH_2O$—), 3.78-3.72 (m, 1H, H-7), 3.34 (s, 3H, $OCH_3$), 2.65-2.60 (m, 1H), 2.46-2.22 (m, 5H), 2.08-1.71 (m, 5H), 1.70-1.06 (m, 15H), 0.92 (d, J=6.4 Hz, 3H, H-21), 0.70 (s, 3H, H-18). APCI-=431.

Preparation of 6

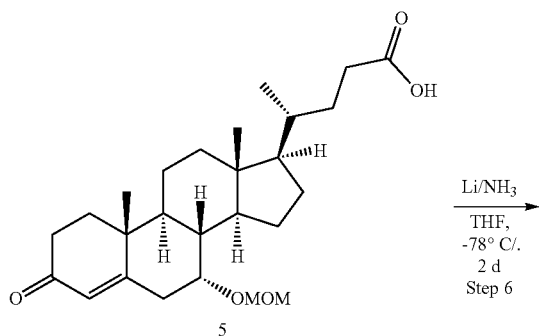

To liquid ammonia (230 mL) was added Li metal (85 mg, 12.3 mmol) in pieces at −78° C. and the blue solution was stirred for 10 min to ensure complete dissolution of Li. A solution of 5 (530 mg, 1.23 mmol) in THF (16 mL) was added and the mixture was stirred for 10 min. The reaction was then quenched with solid NH₄Cl (until color is discharged), allowed to warm to room temperature until all NH₃ had escaped. Water was added to the white solid, which was acidified with 1 M HCl, and extracted with EtOAc (3×50 mL). The combined organic layer was washed with brine, dried over anhydrous Na2SO4, filtered and the solvents were evaporated under reduced pressure. The crude product was purified by silica gel flash chromatography eluting with 0-50% EtOAc-hexanes to give 6 (202 mg, 38%) as a white solid. TLC: Rf=0.5 (silica gel, EtOAc:hexanes, 50:50). 1H-NMR (300 MHz, CDCl₃) δ 4.62 (dd, 12.6, 6.9 Hz, —OCH₂O—), 3.64-3.60 (m, 1H, H-7), 3.38-3.34 (m, 1H, H-4α), 3.34 (s, 3H), 2.44-2.14 (m, 5H), 2.08-1.71 (m, 7H), 1.50-1.20 (m, 12H), 1.19-1.02 (m, 3H), 1.00 (s, 3H, H-19), 0.93 (d, J=6.4 Hz, 3H, H-21), 0.67 (s, 3H, H-18). APCI−=433.

Preparation of 7

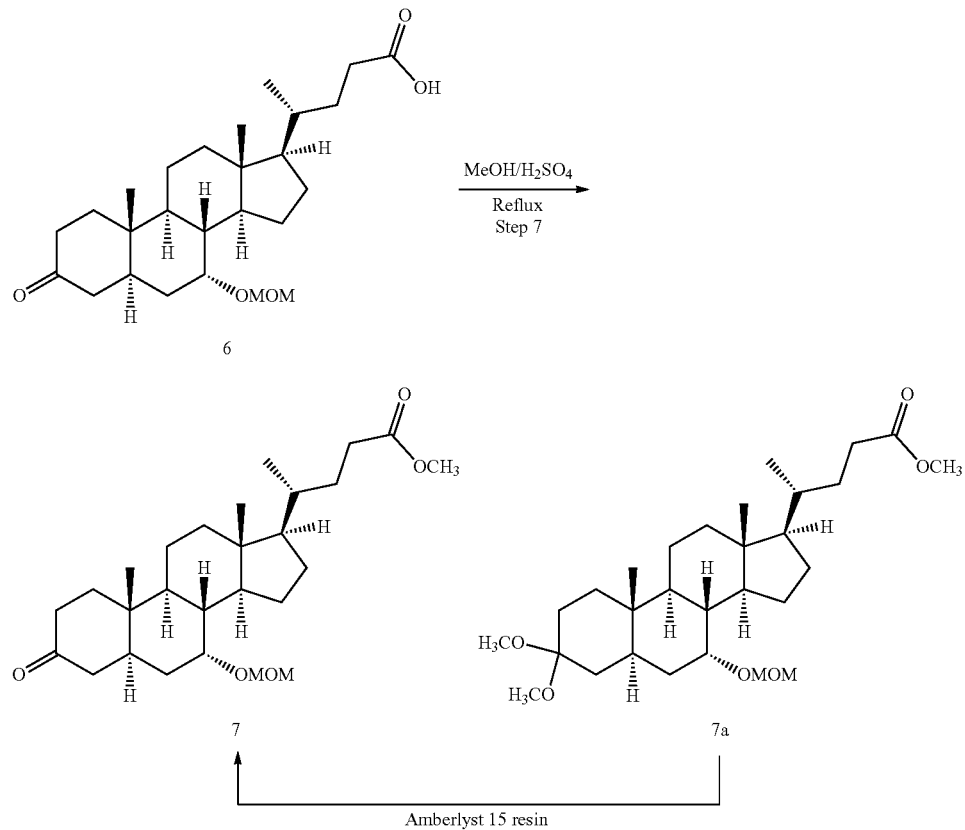

To a solution of 6 (200 mg, 0.46 mmol) in MeOH (10 mL) was added 8 drops of 2% H2SO4 and the mixture was heated at reflux for 3 h. The mixture was cooled to room temperature and diluted with EtOAc (200 mL), washed with saturated NaHCO3 solution (50 mL), brine (20 mL) and dried over anhydrous Na2SO4 then filtered and evaporated to give 200 mg of the product. NMR of the crude product showed a mixture (1:3) of ketone:ketal. This mixture was dissolved in acetone (10 mL) and added 5 drops of water followed by Amberlyst 15 resin (200 mg). The mixture was stirred for 25 min, filtered and washed with acetone. The filtrate was concentrated on a rotary evaporator and dried. The crude product was purified by silica gel flash chromatography eluting with 10-25% EtOAc-hexanes to give 7 (160 mg, 78%) as a white solid. TLC: Rf=0.7 (silica gel, EtOAc: hexanes, 20:80). 1H-NMR (300 MHz, CDCl$_3$) δ 4.62 (dd, J=12.6, 6.9 Hz, Hz, 2H, —OCH$_2$O—), 3.68-3.59 (m, 4H, —CO$_2$CH$_3$ and H-7), 3.38-3.32 (m, 4H, H-4a, OCH$_3$), 2.41-2.16 (m, 6H), 2.12-1.68 (m, 8H), 1.5-1.06 (m, 16H), 1.00 (s, 3H, H-19), 0.92 (d, J=6.4 Hz, 3H, H-21), 0.66 (s, 3H, H-18).

Preparation of 8

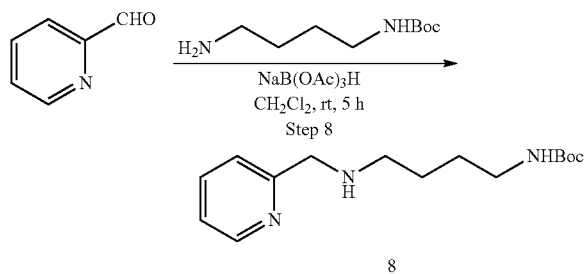

To a solution of picolinaldehyde (5.0 g, 46.7 mmol) in CH$_2$Cl$_2$ (300 mL) was added tert-butyl (4-aminobutyl)carbamate (8.8 g, 46.74 mmol) followed by NaB(OAc)3H (19.8 g, 93.42 mmol) under a nitrogen atmosphere. The mixture was stirred at room temperature for 5 h. The reaction mixture was poured onto saturated NaHCO$_3$ solution (300 mL), and stirred for 10 min. The organic layer was separated, washed with saturated NaHCO$_3$ solution, brine and dried over anhydrous Na2SO4 before filtration and evaporation. The crude product was purified by silica gel flash chromatography eluting with 5-10% MeOH—CH2Cl2 to get 8 (6.9 g, 53%) as a yellow oil. TLC: Rf=0.4 (Silica gel, MeOH:CH$_2$Cl$_2$, 10:90). 1H-NMR (300 MHz, CDCl$_3$) δ 8.54 (m, 1H, H-6), 7.64 (m, 1H, H-4), 7.20 (m, 1H, H-3), 7.18-7.13 (m, 1H), 3.89 (s, 2H, —CH$_2$N—), 3.2-3.05 (m, 2H, —CH$_2$NHBoc), 2.67 (t, 2H, —CH$_2$NH), 1.55-1.53 (m, 4H, —CH$_2$—CH$_2$—), 1.42 (s, 9H, —C(CH$_3$)$_3$). APCI+=280.

Preparation of 9

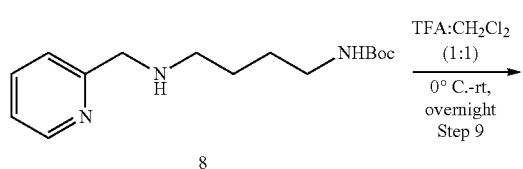

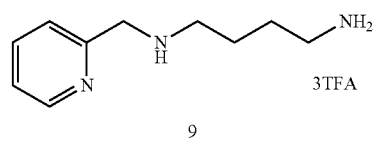

To a solution of 8 (6.9 g, 24.69 mmol) in CH$_2$Cl$_2$ (60 mL) at 0° C. was added TFA:CH$_2$Cl$_2$ (1:1, 40 mL) over 30 min at 0° C. The mixture was allowed to warm to room temperature, stirred overnight, and concentrated on a rotary evaporator along with toluene (5×100 mL) as cosolvent. The crude product was dissolved in water and lyophilized overnight to get a brown oil which was stirred with EtOAc (500 mL). The solid which separated out was filtered, washed with EtOAc and dried under vacuum to get 9 (8.2 g, 64%) as a white solid. $^1$H NMR (300 MHz, CD30D) δ 8.66-8.62 (m, 1H, H-6), 7.91-7.82 (m, 1H, H-4), 7.48-7.39 (m, 2H, H-3, H-5), 4.38 (s, 2H, —CH$_2$N—), 3.2-3.12 (m, 2H, —CH$_2$N), 3.03-2.94 (m, 2H, —CH$_2$N), 1.91-1.70 (m, 4H, —CH$_2$—CH$_2$). APCI+=180.

Preparation of 10

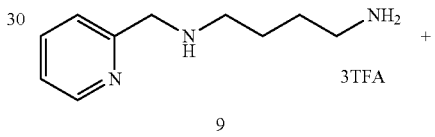

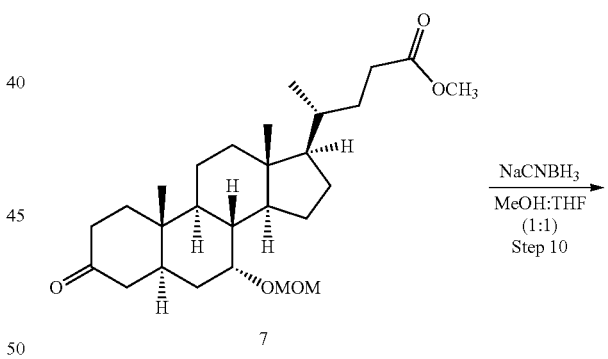

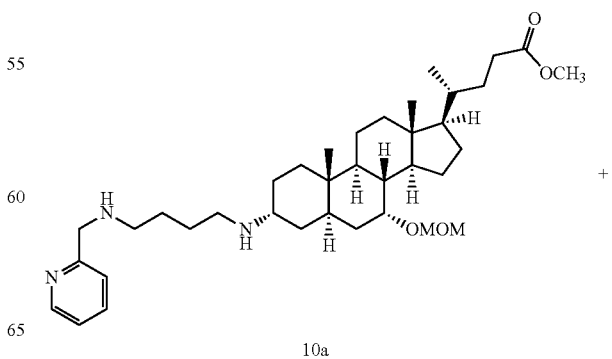

-continued

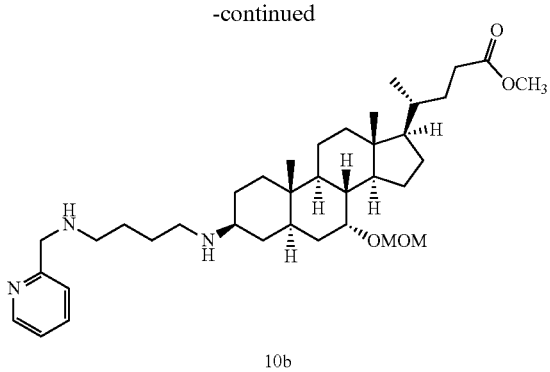

10b

To a mixture of 7 (370 mg, 0.71 mmole) and 9 (160 mg, 0.35 mmole) in CH₃OH:THF (1:1, 8 mL) was added 3 Å molecular sieves (1 g) followed by DIPEA (0.55 g, 4.26 mmol) and the mixture was stirred overnight. Mass spectroscopy revealed incomplete reaction, therefore 1 g of 4 Å molecular sieves was added and the mixture was stirred for 7 h more, then Na BH₃CN was added (71 mg, 1.13 mmol). The mixture was stirred at RT for 2 d. The reaction mixture was filtered through a pad of Celite, and washed with dichloromethane and methanol. The filtrate was concentrated to provide the crude product, which was redissolved in dichloromethane, washed with water, 5% NaOH solution; the aqueous phase was re-extracted with dichloromethane and the combined organic phase was washed with brine, dried (Na₂SO₄) and the solvent was removed under reduced pressure to isolate the crude product. This material was purified by FCC using 1-10% MeOH/CHCl₃ and 1-2% NH₃ in MeOH to isolate 36 mg of 3α-isomer (10a, 16%) and 72 mg of 3β-isomer (10b, 33%).

3α-isomer (10a): $^1$H NMR (300 MHz, CDCl₃) δ 8.56 (m, 1H-Py), 7.63 (dt, J=1.5, 5.7 Hz, 1H-Py), 7.30 (d, J=6.6 Hz, 1H-Py), 7.16 (m, 1H-Py), 4.63 (dd, J=12.6, 6.9 Hz, Hz, 2H, —OCH₂O—), 3.91 (s, 2H, CH₂—Py), 3.65 (s, 3H, COOMe), 3.57 (m, 1H, H-7), 3.33 (s, 3H, OCH₃), 2.84 (m, 1H, H-3β), 2.63 (bt, 2H, —N—CH₂—), 2.55 (bt, 2H, —N—CH₂—), 2.10-2.40 (m, 3H), 1.70-1.90 (m, 7H), 1.00-1.70 (m, 25H), 0.92 (d, J=6.4 Hz, 3H, H-21), 0.77 (s, 3H, H-19), 0.62 (s, 3H, H-18). APCI+=612.

3β-isomer (10b): $^1$H NMR (300 MHz, CDCl₃) δ 8.56 (m, 1H-Py), 7.63 (dt, J=1.5, 5.7 Hz, 1H-Py), 7.30 (d, J=6.6 Hz, 1H-Py), 7.16 (m, 1H-Py), 4.62 (dd, J=12.6, 6.9 Hz, Hz, 2H, —OCH₂O—), 3.92 (s, 2H, CH₂—Py), 3.64 (s, 3H, COOMe), 3.57 (m, 1H, H-7), 3.35 (s, 3H, OCH3), 2.60-2.75 (m, 4H, —N—CH₂—CH₂—N—), 2.40-2.55 (m, 1H, H-3O), 2.10-2.40 (m, 3H), 1.58-1.90 (m, 13H), 1.00-1.55 (m, 18H), 0.89 (d, J=6.4 Hz, 3H, H-21), 0.69 (s, 3H, H-19), 0.61 (s, 3H, H-18). APCI+=612

Preparation of 11

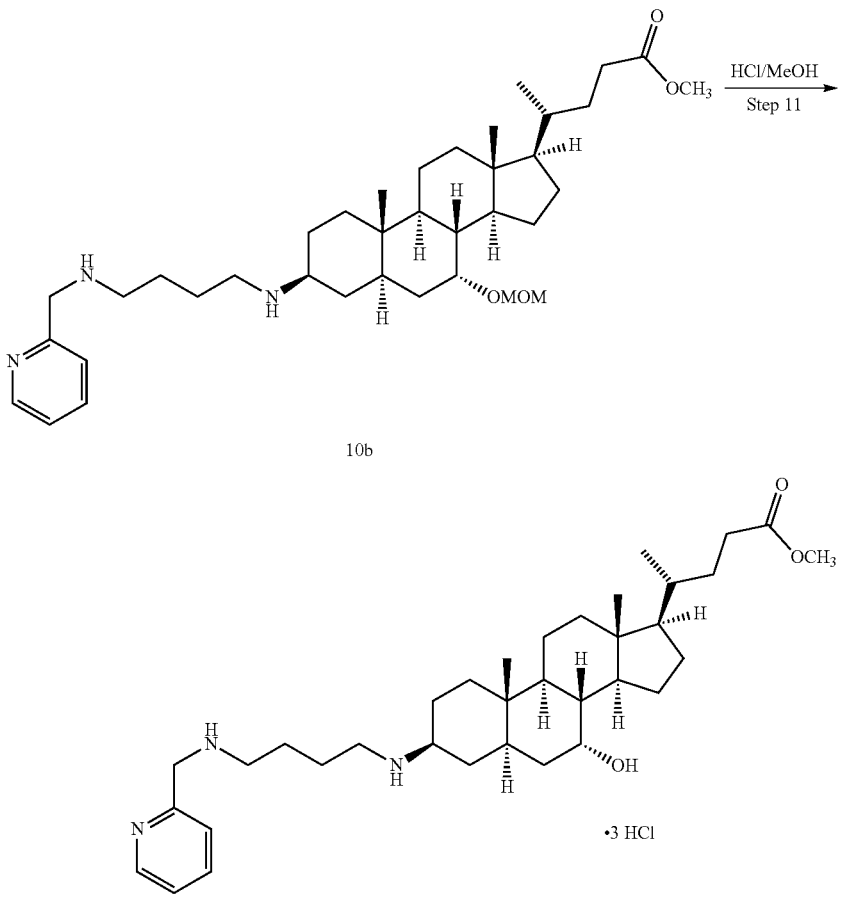

To a solution of compound 10b (71 mg, 0.116 mmol) in MeOH (3 mL) in a sealed tube was added HCl in MeOH (1.25 M, 0.46 mL, 0.58 mmol) and the mixture was heated at 65° C. for 2.5 h, and since the reaction was incomplete, 0.1 mL of excess HCl in MeOH was added and the reaction was continued at 65° C. for 7 h. The reaction mixture was concentrated and dried to isolate 95 mg (>100%) of compound 11. A total of 8 mg of crude product was used in attempted purifications (chromatography; washing; trituration) without success. The remaining material was dried in vacuo overnight. A total of 82 mg was sent to Ohr.

$^1$H NMR (300 MHz, CD3OD) δ 8.74 (m, 1H-Py), 8.13 (dt, J=1.5, 5.7 Hz, 1H-Py), 7.77 (d, J=6.6 Hz, 1H-Py), 7.65 (m, 1H-Py), 4.50 (s, 2H, CH2-Py), 3.80 (m, 1H, H-7), 3.64 (s, 3H, COOMe), 3.00-3.30 (m, 5H, —N—CH$_2$—CH$_2$—N—, H-3a), 2.19-2.41 (m, 2H), 1.11-2.10 (m, 28H), 0.93 (d, J=6.4 Hz, 3H, H-21), 0.87 (s, 3H, H-19), 0.69 (s, 3H, H-18). APCI+=568. HPLC=94%.

An alternative synthesis scheme is as follows:

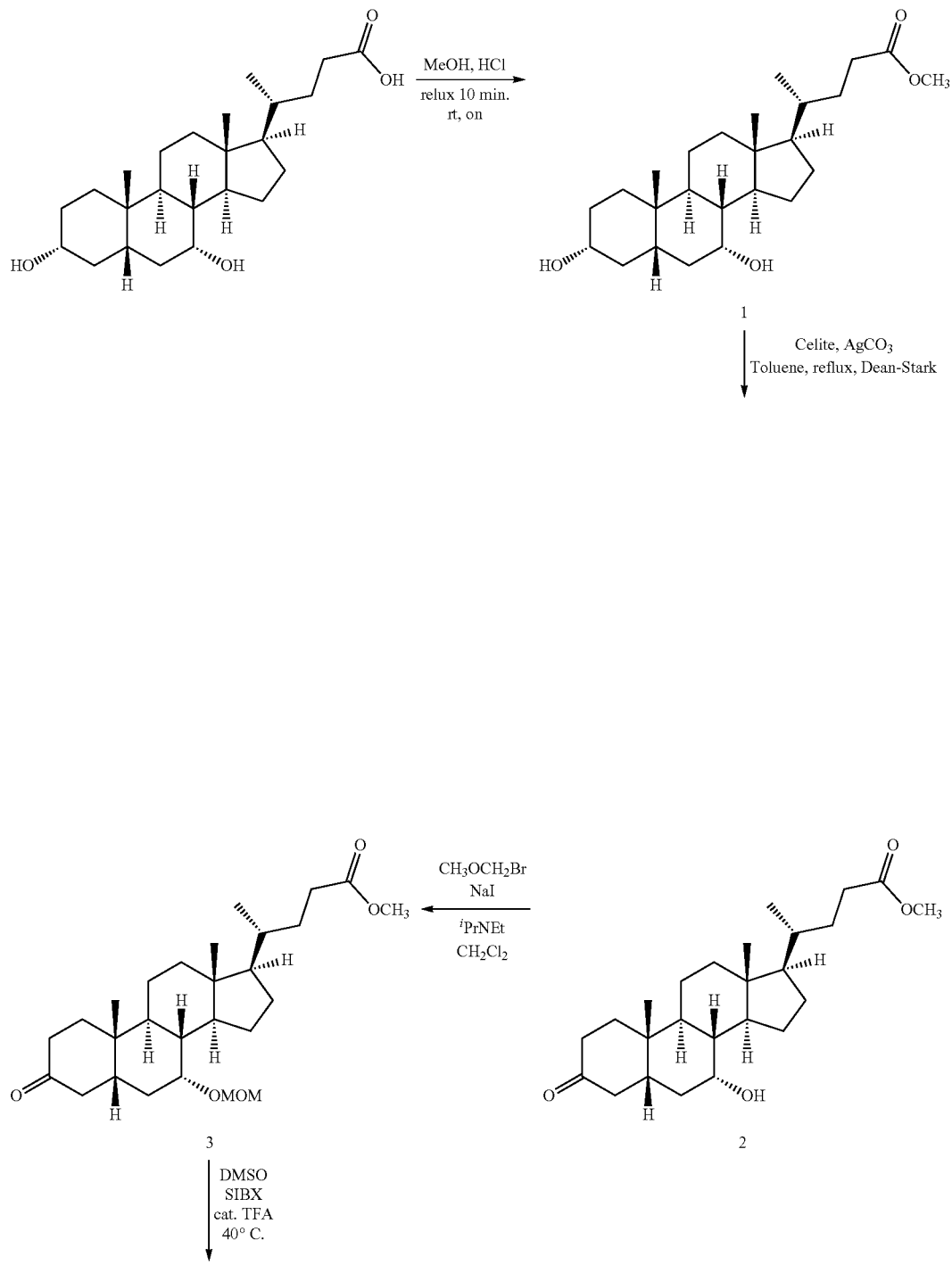

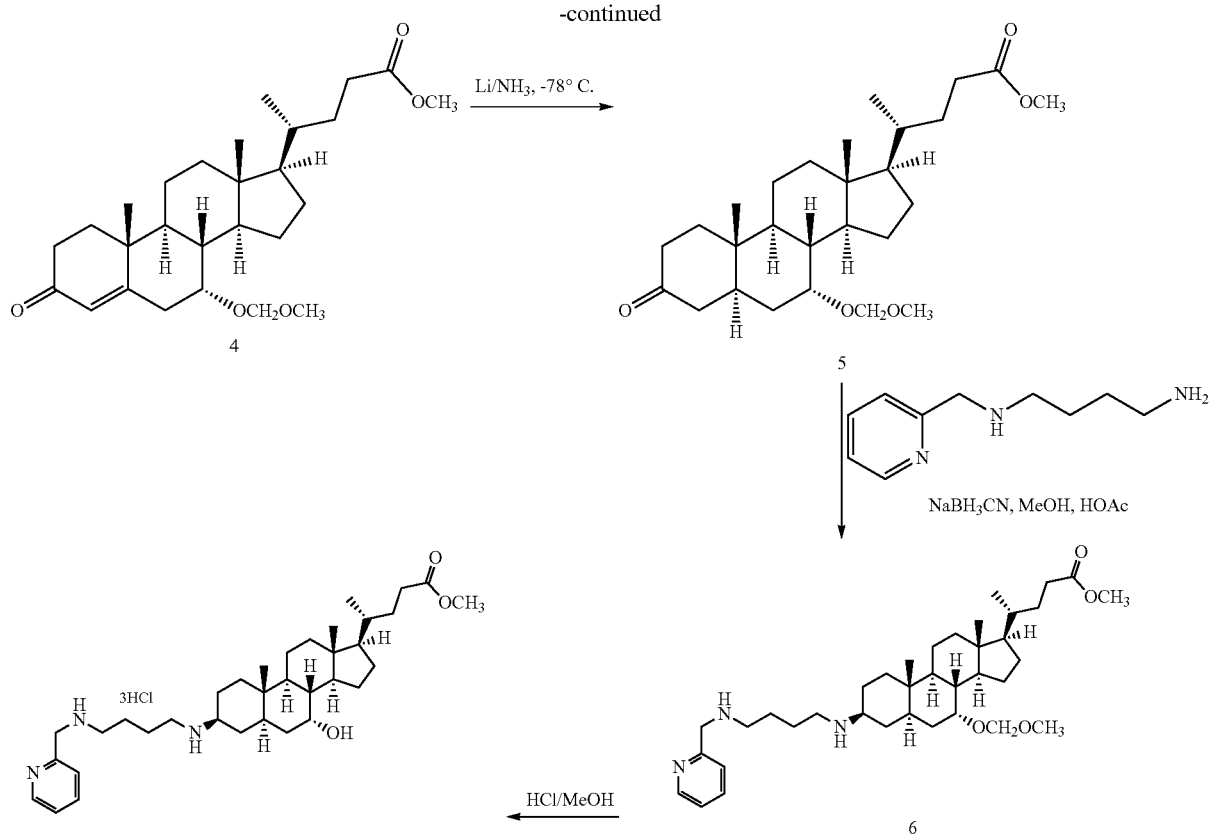
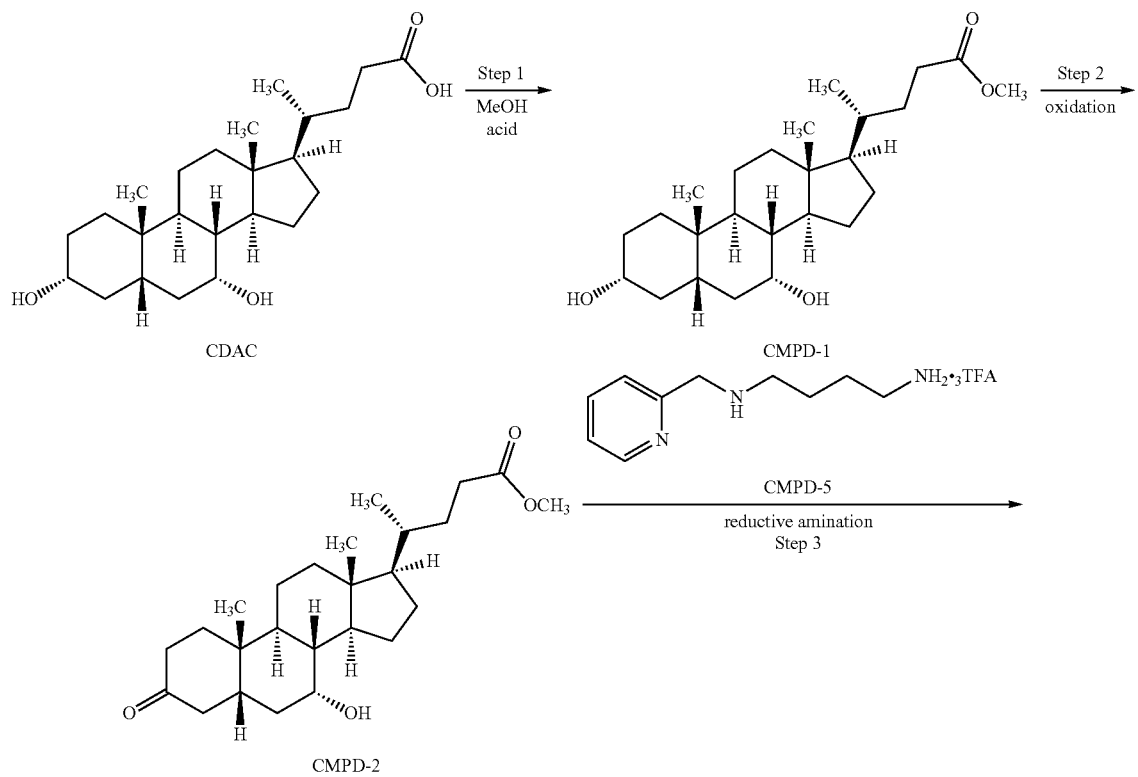
Preparation of 4

-continued
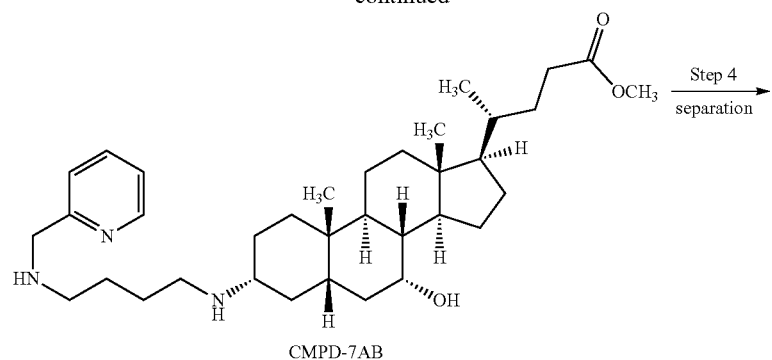
CMPD-7AB
Step 4
separation
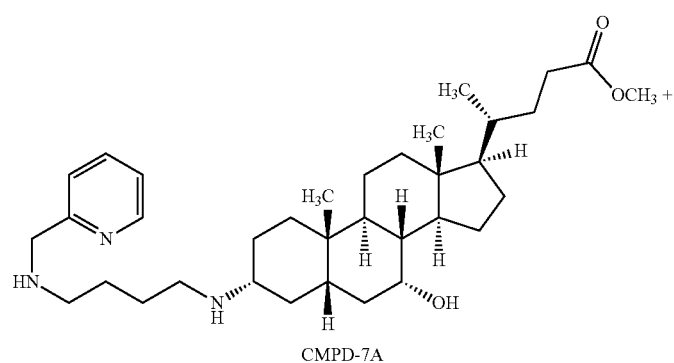
CMPD-7A
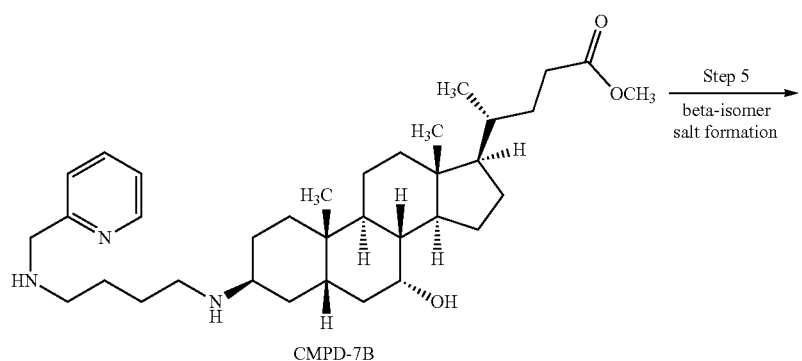
CMPD-7B
Step 5
beta-isomer salt formation
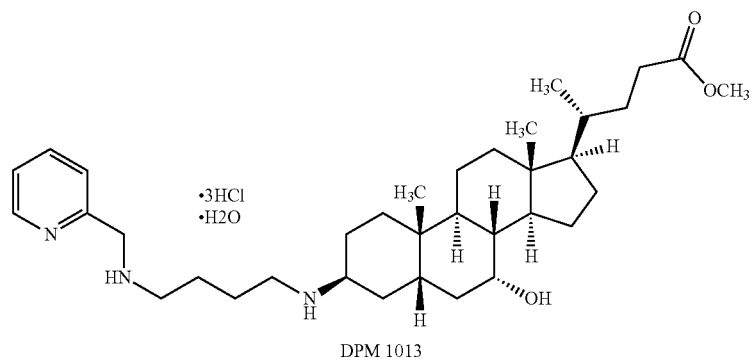
DPM 1013
·3HCl
·H2O Mixtures of isomers may then be separated by column chromatograph (similar to DPM-1001) to separate the β-cis- and α-cis analogs (i.e., DPM-1013 and DPM-1014, respectively), to a relative purity of 9500, as follows:
Scheme 1
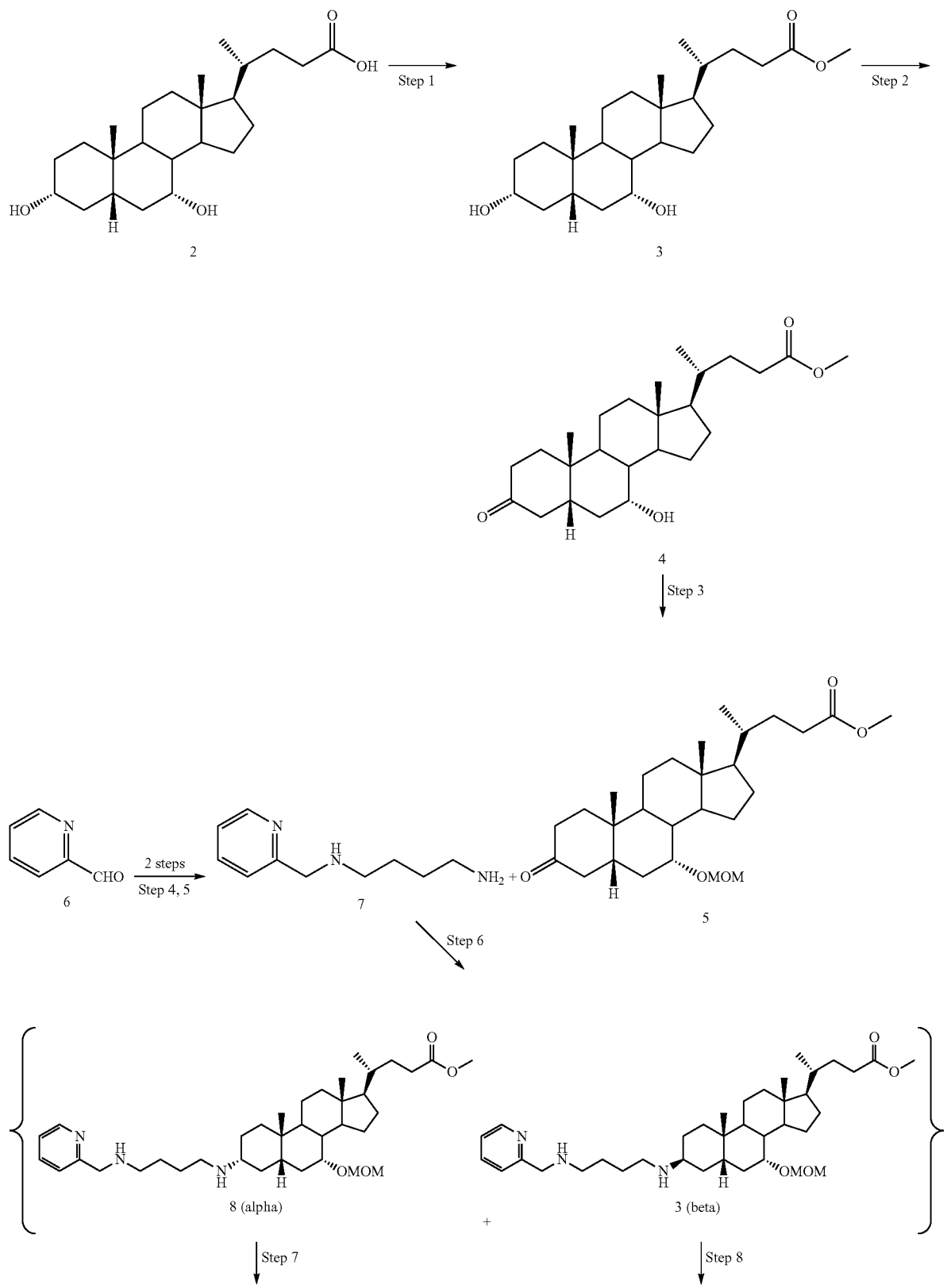

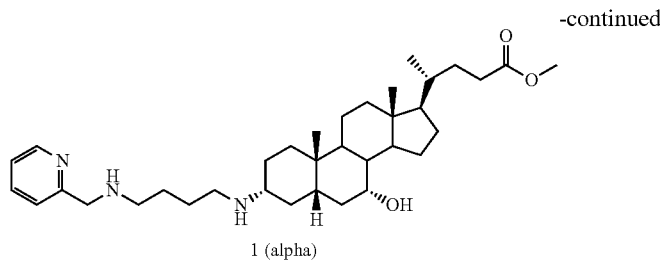

1 (alpha)

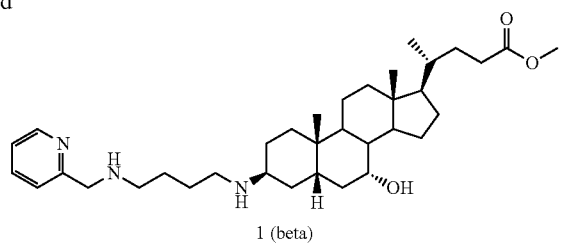

1 (beta)

Compound of Formula I Bind Copper and Improve Leptin and Insulin Signaling and Obesity Methods Reagents All common reagents were obtained from Thermo Fisher Scientific (Waltham, MA) or Sigma-Aldrich (St. Louis, MO). Difluoro-4-methylumbelliferyl phosphate (DiFMUP) was obtained from Invitrogen (cat #D22065). Solid black 384-well plates (cat #3573) for phosphatase assays were from Corning Incorporated (Corning, NY).

Antibodies

The antibodies used in the study were purchased from: Upstate Biotechnology (pTyr, catalog 05-321, clone 4G10); Invitrogen (pY1162/1163-IR-β, catalog 700393, clone 97H9L7); Santa Cruz Biotechnology Inc. (IR-β, catalog sc-711, clone C711); Cell Signaling Technology (JAK2, catalog 3230, clone D2E12; p-T308 AKT (catalog 13038, clone D25E6); AKT (catalog 4691, clone C67E7) and Sigma-Aldrich (actin, catalog A2228, clone AC-74).

Purification of PTP1B

Wild-type PTP1B containing a His-tag was expressed in *Escherichia coli* BL21 (DE3)-RIL using LB. Cells were resuspended in lysis buffer (50 mM Hepes pH 7.2, 150 mM NaCl, 10 mM imidazole, 2 mM TCEP) with cOmplete EDTA-free Protease Inhibitor Cocktail (Roche), and then lysed using a sonicator at 4° C. Lysates were clarified by centrifugation. Initial protein purification was by gravity flow, nickel column chromatography. Protein was used immediately or stored at −80° C. in in 50 mM HEPES pH 7.4, 100 mM NaCl, 2 mM dithiothreitol and 25% glycerol.

Gel Filtration

PTP1B (5 μM) was incubated with 10 μM MSI1436 in a final volume of 200 μl buffer (50 mM HEPES, pH 7.0, 100 mM NaCl, 0.2 mM EDTA, 2 mM DTT) at 4° C. The reaction mixture was then subjected to gel filtration on a Superdex 200 column (HR30/10; Pharmacia Biotech Inc.). Prior to loading the MSI1436-saturated protein sample, the column was equilibrated with 50 mM HEPES, pH 7.0, 100 mM NaCl, 0.2 mM EDTA and 2 mM DTT. The void volume ($V_o$) and total volume ($V_t$) were measured using blue dextran and Coomassie blue dye, respectively. Fractions of 0.5 ml were collected, and the protein concentration in each sample was determined by Bradford assay or by recording the UV absorption spectrum at 280 nm.

Copper-Binding Assays

Direct binding assays were performed using radiolabelled copper (64 $Cu^{2+}$). Varying concentration of radiolabeled copper (0-100 nM) was incubated with DPM-1001 (100 nM). Excess copper was removed by running the samples through a desalting column. The amount of metal bound to the compound was quantitated directly by scintillation counting. For assays with the protein, His-tagged PTP1B (100 nM) was incubated with varying concentrations of Cu-DPM-1001 complex for 60 min in assay buffer (50 mM Hepes, 100 mM NaCl, 0.1% BSA pH 6.5) at 25° C. Protein-bound and free compound were separated by incubating the protein-inhibitor mixture with 50 μl of 50% Ni-NTA beads for 10 min at 25° C. The beads were washed with assay buffer containing 150 mM NaCl and 25 mM Imidazole three times, and the inhibitor bound to protein was determined by scintillation counting. The amount of bead-bound protein was estimated by BCA protein quantification.

ESI-MS Analysis of DPM-1001-Copper Complex

Eight equivalents of $M(NO_3)_2 \cdot xH_2O$ or $MSO_4 \cdot xH_2O$ (M=Cu, Zn) were reacted with 1 eq. of DPM-1001 (1 mM in $H_2O$). The reaction solutions were stirred at RT, 40° C. and 80° C. for 2 h. Mass spectra were recorded on a Bruker Esquire 6000 HCT quadrupole ion trap instrument (Bruker Daltonik GmbH, Leipzig, Germany), equipped with an electrospray ionization (ESI) source. Generation of the molecular formula of the DPM-1001/Cu(II) species and the comparison between the theoretical (simulated) and the measured isotopic patterns was performed using the DataAnalysis 4.0 software (Bruker).

Animal Experiments.

All protocols were approved by the Institutional Animal Use and Care Committee of Cold Spring Harbor laboratory. 10 week-old male mice fed chow diet or high-fat diet (D12492) were acclimatized for 10 days under standard conditions before experiments. Mice were injected intraperitoneally (i.p.) once daily with vehicle, 5 mg/kg of DPM-1001 intraperitoneally or orally for 50 days. Mice were euthanized after 6 h of fasting, and serum samples were collected to measure the metabolic parameters and tissue samples were collected for studying changes in signaling.

Metabolic Measurements.

Glucose in tail blood was measured using a glucometer (One-Touch Basic; Lifescan, CA). For glucose tolerance tests (GTTs), mice were fasted for 10 hours and then injected 20% D-glucose (2 mg/g body weight) and the blood glucose was monitored immediately before and at 15, 30, 60 and 120 mins following the injection. For insulin tolerance tests (ITTs), 4-h fasted animals were given insulin (0.75 mU/g) and blood glucose was measured immediately before and at 30, 60 and 120 minutes postinjection. Statistical analysis was performed using ANOVA for both GTT and ITT.

Results

Figure 1:
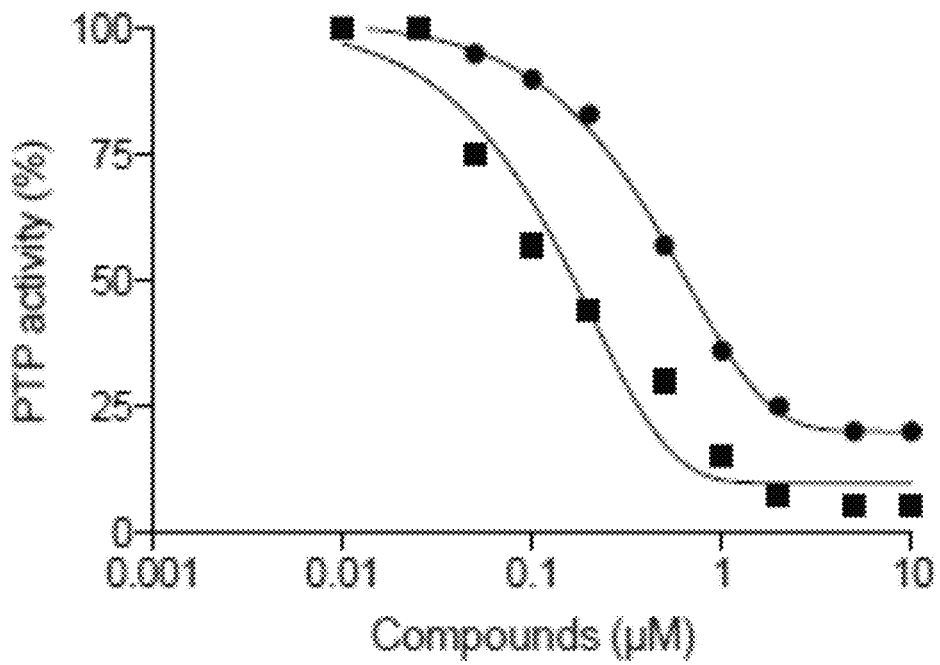
FIG. 1 shows effects of increasing concentrations of DPM-1001 (squares) and MSI-1436 (circles) on inhibition of the long form of the phosphatase, PTP1B$_{1-405}$, using DiFMUP as substrate.
Figure 2:
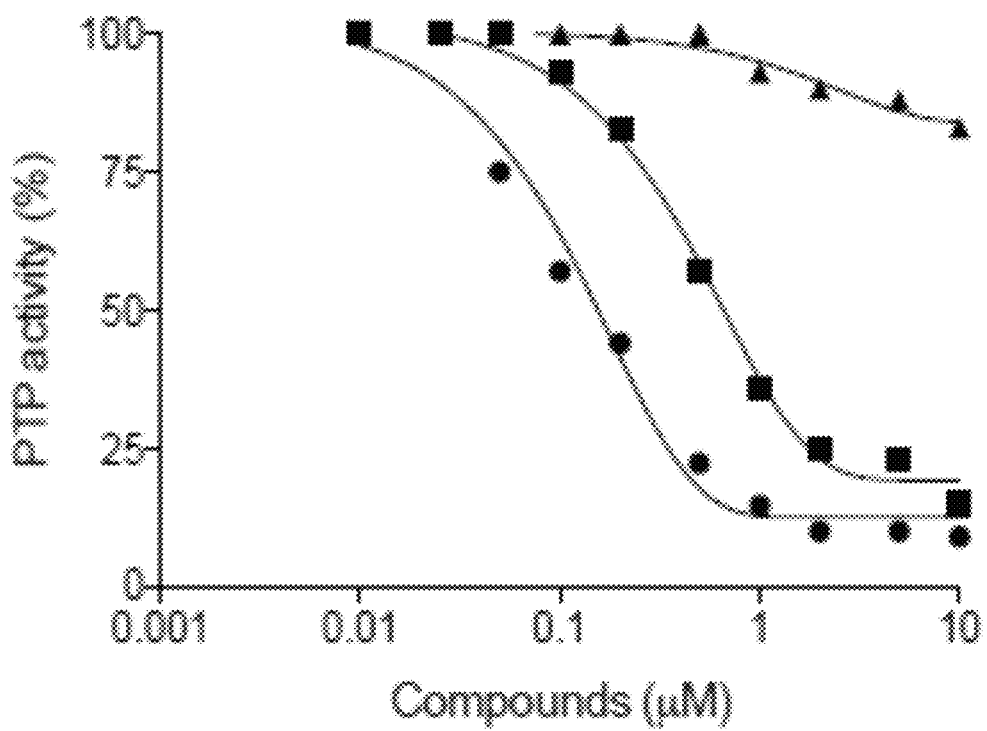
Figure 3:
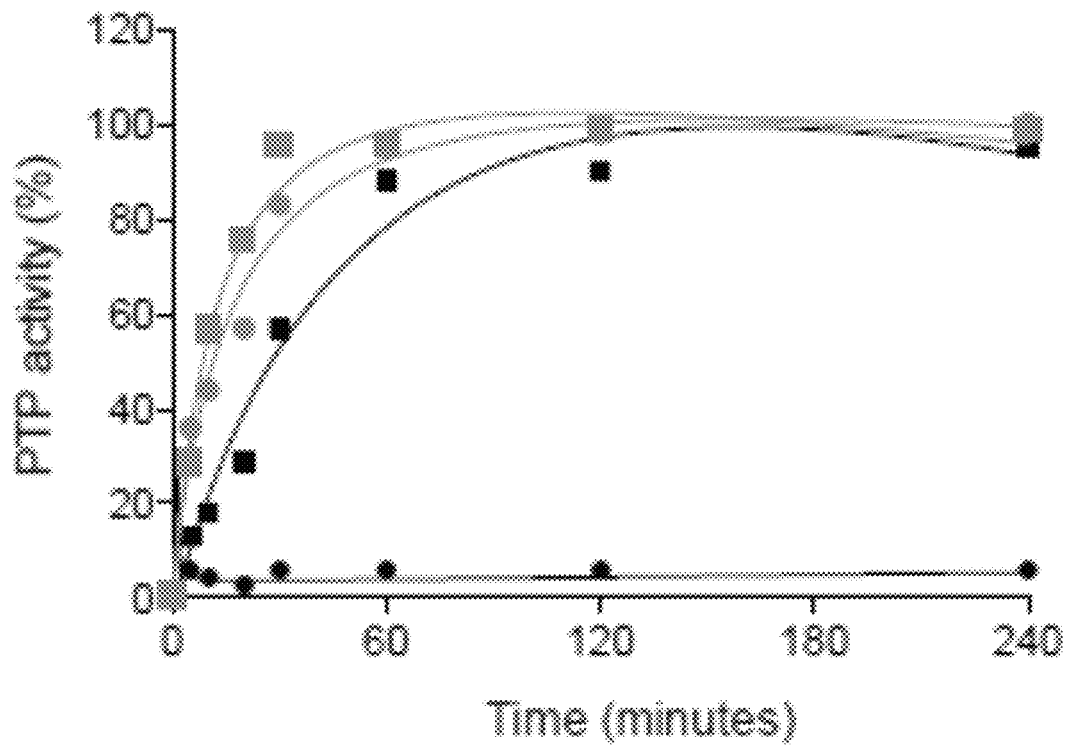
Figure 4:
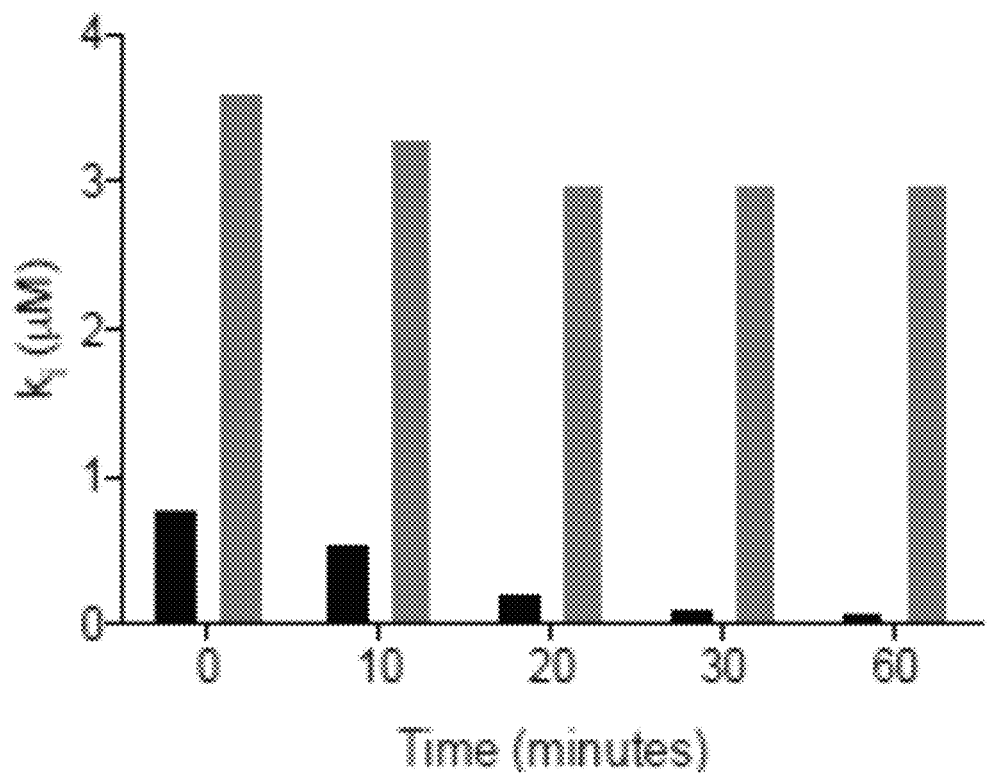

DPM-1001 ($IC_{50}$ 100 nM) was found to be a more potent inhibitor of the phosphatase than MSI-1436 ($IC_{50}$ 600 nM). FIG. 1. To investigate the mechanism of inhibition by DPM-1001, we tested it against PTP1B-L192A/S372P, an MSI-1436-resistant mutant form of the protein. Although PTP1B-L192A/S372P was insensitive to MSI-1436, the mutant enzyme was inhibited by DPM-1001 ($IC_{50}$ of 1 μM), but with decreased sensitivity compared to the wild-type phosphatase. FIG. 2. This indicated differences in the mechanism of inhibition of PTP1B by MSI-1436 compared to DPM-1001. Reversibility of inhibition was examined by diluting the enzyme-inhibitor complex and monitoring the extent to which the phosphatase activity could be recovered. In contrast to MSI-1436, which was found to be a reversible inhibitor of both PTP1B$_{1-405}$ (the long form of PTP1B which contains the extended C-terminal segment) and PTP1B$_{1-321}$, DPM-1001 inhibited the short form of PTP1B reversibly, whereas PTP1B$_{1-405}$ remained inactive over an extended period of time. FIG. 3. To examine the time dependence of inhibition by DPM-1001, the activity of the long and short forms of PTP1B was measured after incubation with DPM-1001 for varying times. The inhibitory potency of DPM-1001 against PTP1B$_{1-405}$ improved with longer incubation of the enzyme and the compound. With no pre-incubation the IC50 for PTP1B$_{1-405}$ was 600 nM, similar to that of MSI-1436; however, after a 30 minute pre-incubation the potency was improved to 100 nM. In contrast, there was no obvious time dependent change in the IC$_{50}$ for PTP1B$_{1-321}$, indicating that the C-terminus of PTP1B was required for the difference in behavior of the two compounds. FIG. 4.

Figure 5:
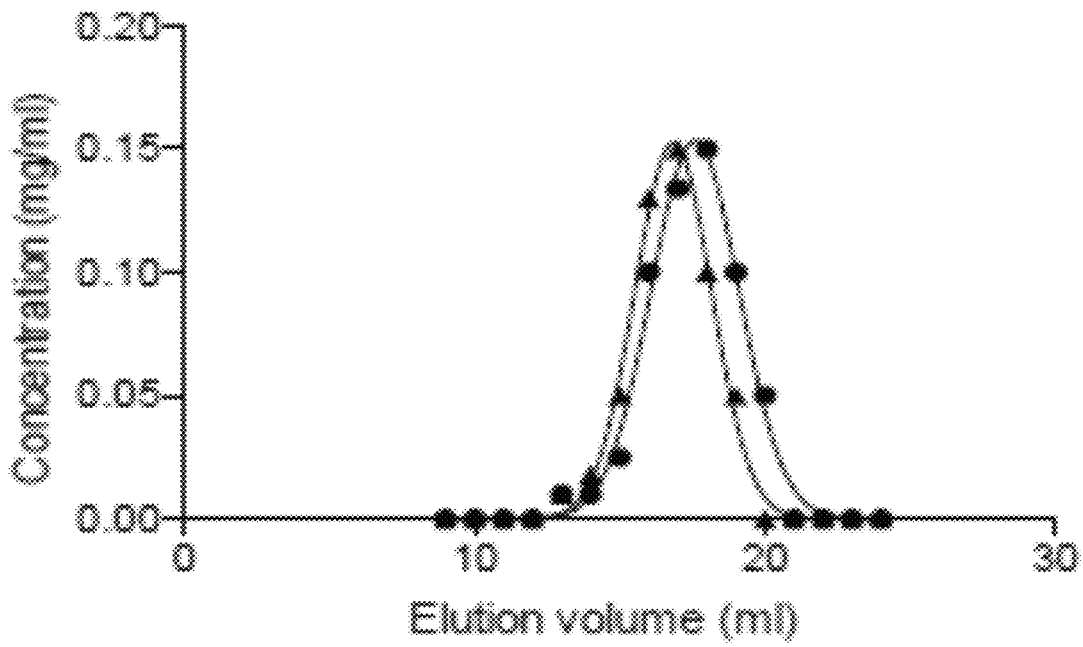
Figure 6:
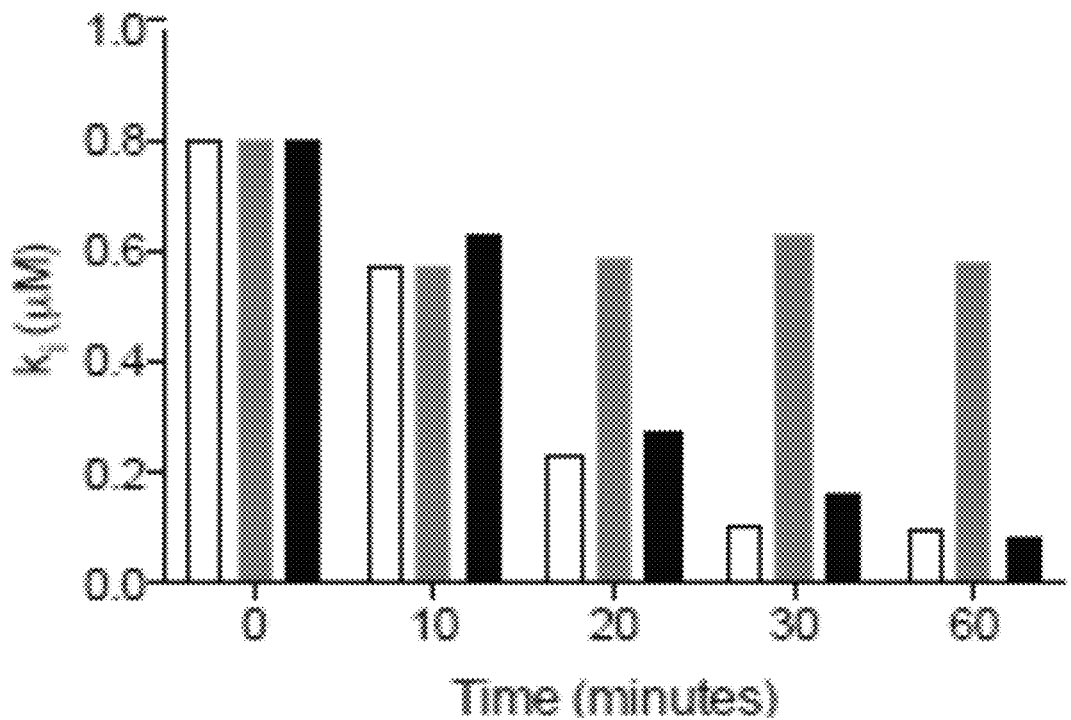

In examining further the basis for time dependence, DPM-1001 did not induce aggregation of PTP1B, thus eliminating this nuisance mechanism. FIG. 5. It is now well established that the active site cysteine in PTP1B is highly susceptible to oxidation and there have been reports that small molecules can promote production of reactive oxygen species in phosphatase assays; therefore, whether DPM-1001 promoted preferential oxidation and inactivation of the long form of the enzyme was tested. DPM-1001-mediated inhibition of PTP1B$_{1-405}$ in the presence or absence of either peroxiredoxin 1 (PRX1) or catalase (CAT) was measured, because both of these enzymes degrade H$_2$O$_2$ to H$_2$O, but by different mechanisms. There was a time-dependent increase in potency for DPM-1001-mediated inhibition of PTP1B$_{1-405}$ in the presence or absence of PRX1 (FIG. 6), suggesting that this effect was not due to oxidation and inactivation of the phosphatase mediated by the compound. There was no obvious time dependence of inhibition in the presence of catalase (FIG. 6). Unlike PRX1, catalase is a metal-dependent enzyme. Therefore, catalase may bind to metal ions present in the assay buffer as impurities and, therefore, prevent DPM-1001 from inhibiting PTP1B in a metal ion-dependent manner.

DPM-1001 Formed a Stable Complex with Copper(II)

Figure 7:
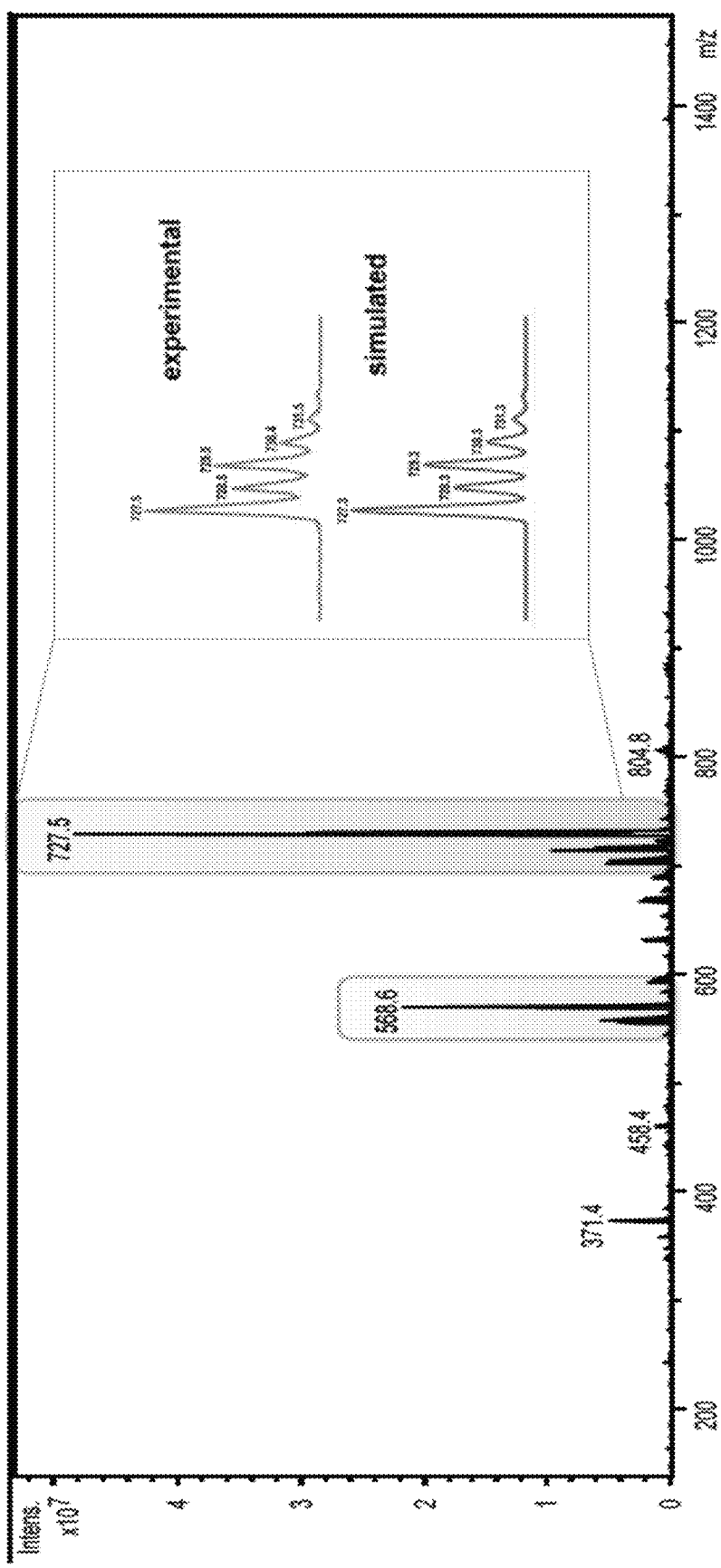
Figure 8A:
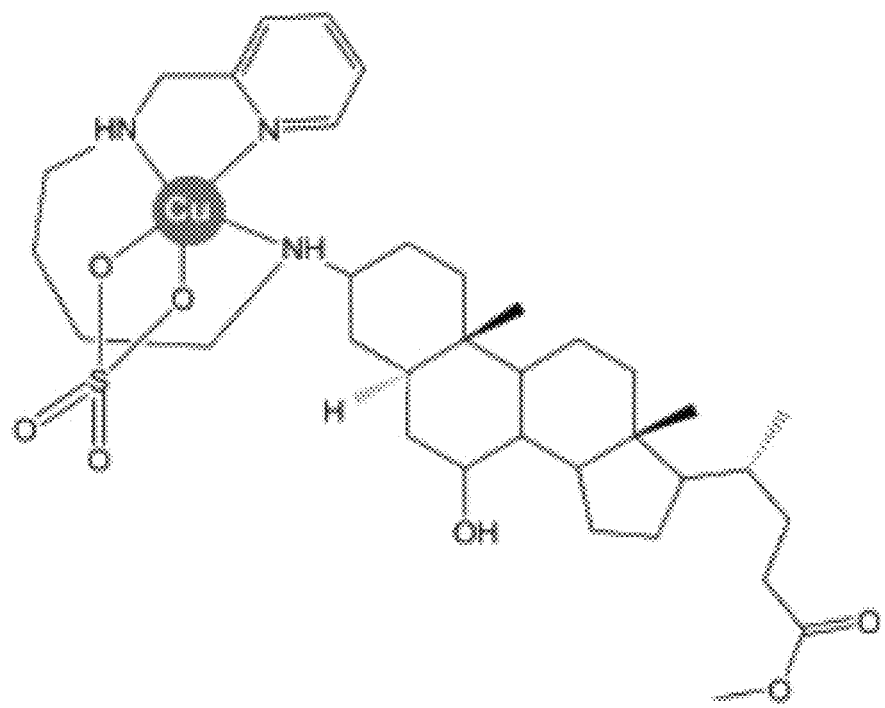

DPM-1001 was reacted with an excess of CuSO$_4$ or Cu(NO$_3$)$_2$ and subjected to ESI-MS analysis. The ESI-MS spectra of the DPM-1001/CuSO$_4$ reaction mixture revealed two major peaks at m/z 568.6 and 727.5, consistent with the free DPM-1001 and a Cu(II) complex bound to both DPM-1001 and a sulphate anion, respectively. After analyzing the isotopic pattern, the latter was identified as [Cu(DPM-1001)(SO$_4$)+H+]$^+$ (FIG. 7). In the presence of copper nitrate, spectral peaks at m/z 692.5 and 755.5 were detected, which correspond to the structures of [Cu(DPM-1001)(NO$_3$)]$^+$ and [Cu(DPM-1001)(NO$_3$)$_2$+H$^+$]$^+$. Without being limited to any particular binding mechanism or structure, DPM-1001 may act as a tridentate ligand forming one seven-membered and one five-membered chelate ring, while the environment around the Cu (II) is most likely to be five-coordinate displaying either a square pyramidal or a trigonal bipyramidal geometry (FIG. 8A). Square planar geometry, although rather typical for Cu (II), is not favored in this case due to the nature of the DPM-1001 ligand, whereas tetrahedral geometry is quite rare (the structure normally goes through solvent/counteranion coordination or ligand rearrangement affording thermodynamically more stable compounds with higher coordination numbers).

Figure 9:
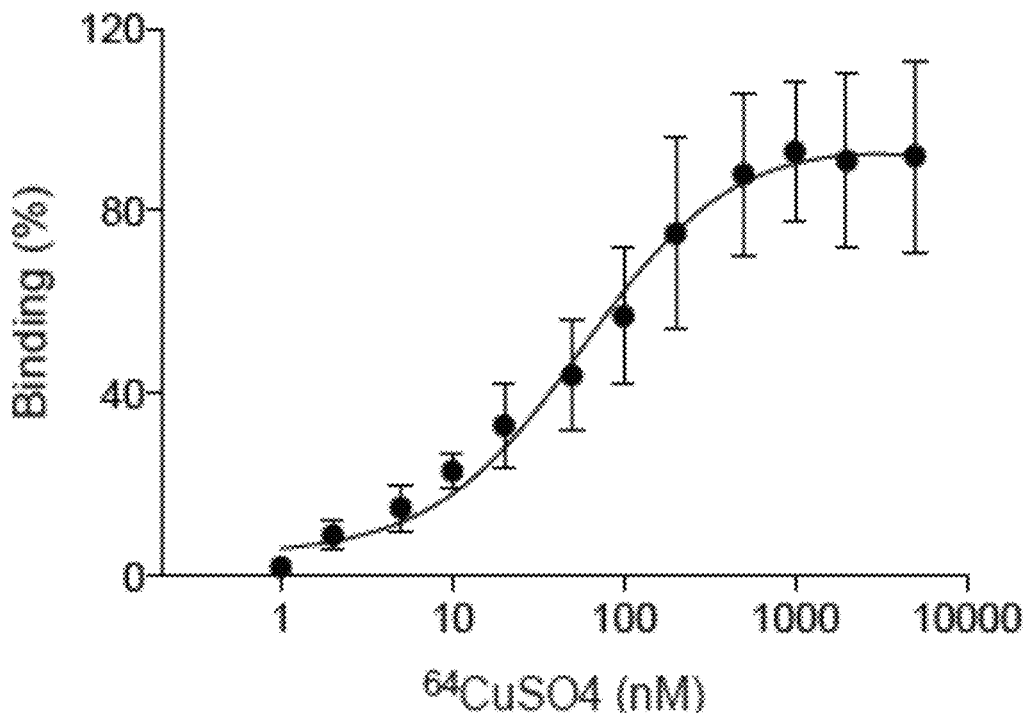

To examine further the chelation properties of DPM-1001, radiolabelled copper ($^{64}$Cu) was used to determine the affinity of DPM-1001 for the metal. By titrating DPM-1001 against increasing concentration of $^{64}$Cu, a Kd of 75 nM and a stoichiometry of 1 mol/mol were measured. FIG. 9. Other known Cu$^{2+}$ chelators have been shown also to chelate Zn$^{2+}$ ions; therefore, DPM-1001 was reacted with ZnSO$_4$ or Zn(NO$_3$)$_2$ and subjected the solution to ESI-MS analysis. In all cases, only a major peak was detected at m/z 568.6 corresponding to DPM-1001; there was no complexation of DPM-1001 with Zn(II).

DPM-1001 Bound to the C-Terminus of PTP1B and Inhibited the Enzyme

To define the mechanism by which a Cu-DPM-1001 complex inhibited PTP1B, truncation mutations were generated in which varied the lengths of the C-terminal segment of the phosphatase were varied. Similar to MSI-1436, the inhibitory potency of DPM-1001 was lower for three truncation mutants PTP1B$_{1-367}$, PTP1B$_{1-346}$ and PTP1B$_{1-321}$ than it was for PTP1B$_{1-405}$ and PTP1B$_{1-394}$. Furthermore, the time dependence in inhibition was observed only for PTP1B$_{1-405}$ and PTP1B$_{1-394}$. This highlights the importance of the extended C-terminus for time-dependent inhibition of PTP1B.

Figure 10:
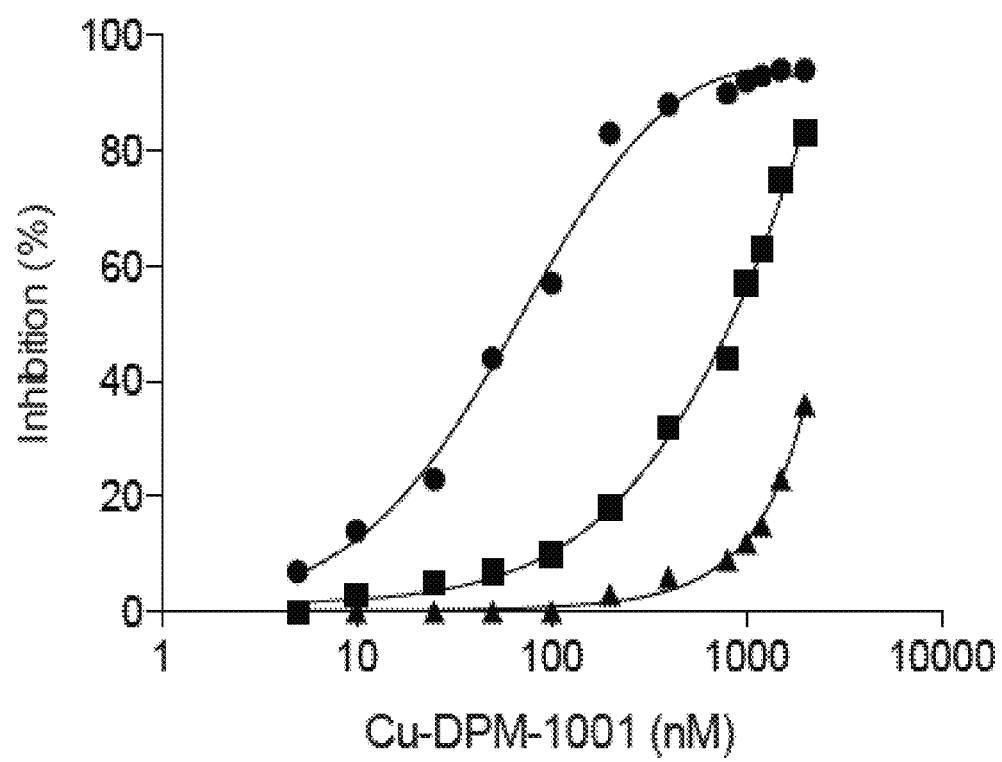

Considering the documented importance of His residues in copper binding sites in proteins, effects of mutating His residues to Ala in the C-terminal segment of PTP1B on time-dependent inhibition mediated by the Cu-DPM-1001 complex was tested. In particular, mutation of His residues H320 and H331 resulted in a marked reduction in the inhibitory potency of Cu-DPM-1001. FIG. 10. Furthermore, combining the H320A/H331A mutations with S372P/L192A, which desensitized PTP1B to MSI-1436, produced a further rightward shift in the potency of Cu-DPM-1001-mediated inhibition of PTP1B, from nanomolar to micromolar. FIG. 10.

Figure 11:
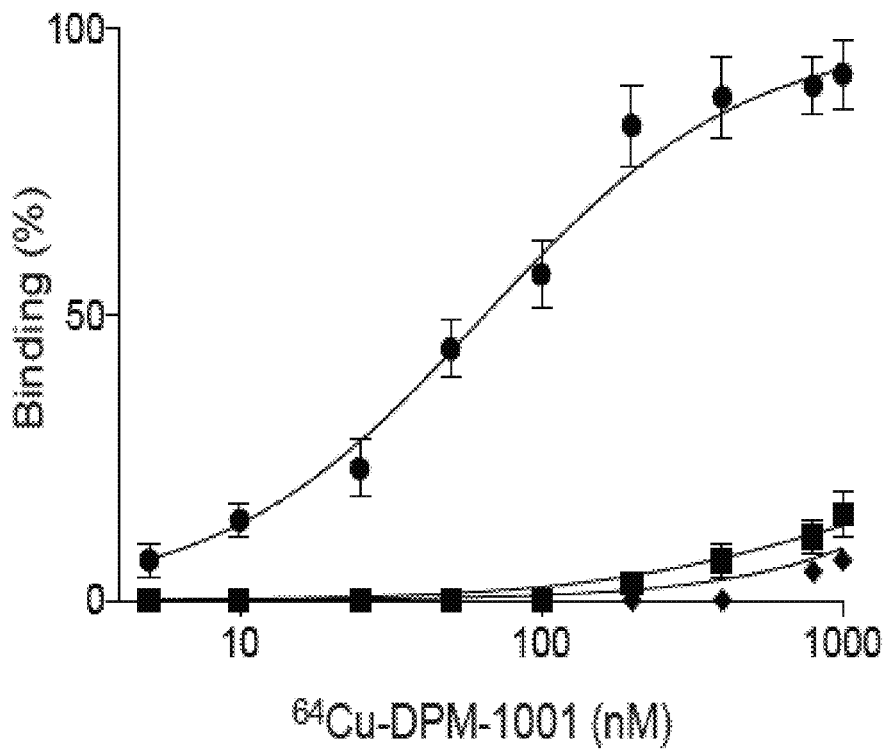
Figure 12:
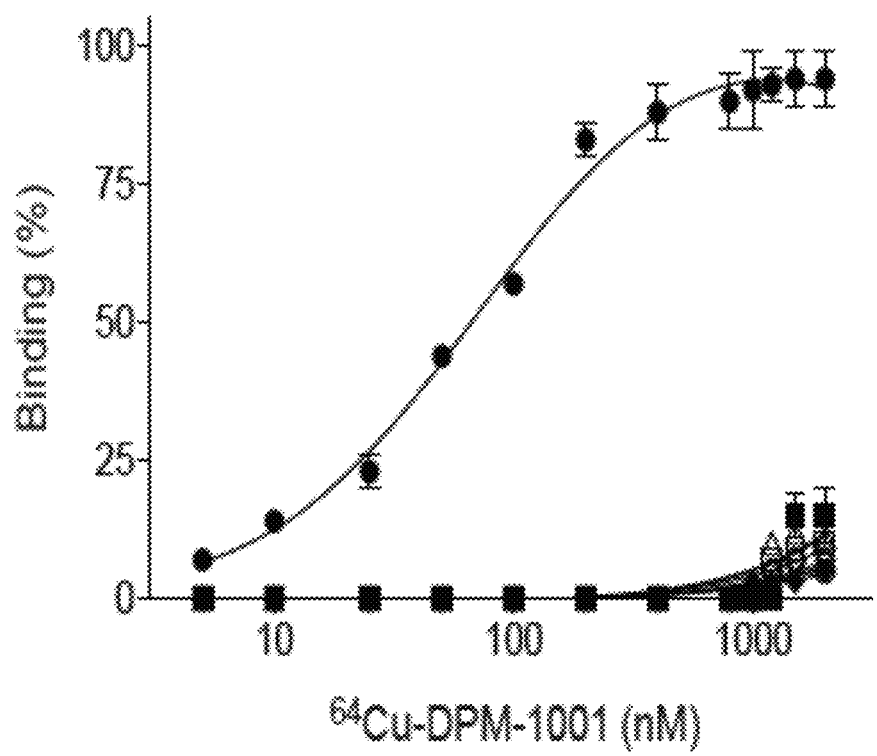

The Cu-DPM-1001 complex was tested against a panel of six PTPs and observed, again similar to MSI-1436, that there was preferential inhibition of the long form of PTP1B, containing the C-terminal segment, compared to the other PTPs tested. There was a direct interaction between Cu-DPM-1001 and PTP1B. Using radiolabelled copper ($^{64}$Cu), a complex of $^{64}$Cu and DPM-1001 was generated and binding assays were conducted with wild-type and mutant forms of PTP1B. Free radiolabelled copper was titrated against long and short forms of PTP1B and copper, at high concentration, could bind to PTP1B without a preference for the long and short form of the enzyme. All subsequent assays were conducted at copper concentrations below 0.1 mM to minimize direct interaction between Cu and PTP1B. Wild-type PTP1B$_{1-405}$ was tested against $^{64}$Cu-DPM-1001 complex, which revealed a K$_d$ of 75 nM for the interaction. FIG. 11. This was consistent with the observed IC$_{50}$ in in vitro phosphatase activity assays. In contrast, little binding of the $^{64}$Cu-DPM-1001 complex to the C-terminally truncated PTP1B (1-321) was detected. Similarly, the binding of the $^{64}$Cu-DPM-1001 complex to the H320A/H331A double mutant form of PTP1B was dramatically decreased relative to wild type, even at high concentrations of the complex. FIG. 11. As seen in activity assays, the specificity of the Cu-DPM-1001 complex for PTP1B over other members of the PTP family was recapitulated in these binding assays. FIG. 12. Without being limited to any particular mechanism of an inhibition of activity of PTP1B, these data reveal a novel mechanism for inhibition of PTP1B that incorporates features of the allosteric site that is targeted by MSI-1436, but superimposes an additional feature of copper-dependent binding.

DPM-1001 Inhibited Diet-Induced Obesity in Mice by Improving Insulin and Leptin Signaling PTP1B is a negative regulator of insulin and leptin signaling; consequently, an inhibitor of PTP1B, such as DPM-1001, would be expected to promote signaling through insulin and leptin receptors. High-fat diet-fed C57Bl6/J mice were used to examine the effects of DPM-1001 on obesity, metabolism and signal transduction in animals. High fat diet- and chow diet-fed mice were treated with DPM-1001. The effect of the compound delivered orally or intraperitoneally was compared to saline-treated mice. In contrast to saline, DPM-1001-treated, high fat diet-fed mice started losing weight within five days of treatment. The weight loss continued for approximately three weeks, after which no further decrease in body weight was observed. Overall, treatment with DPM-1001 led to an ~5% decrease in body weight. FIG. 13. Importantly, the same effects were observed when the compound was delivered orally or intraperitoneally. Furthermore no weight loss was noted with chow fed mice, suggesting that the weight loss observed is a consequence of improved energy metabolism in the obese animals.

In contrast to administration of saline, treatment with DPM-1001, either orally or intraperitoneally, improved glucose tolerance and insulin sensitivity in glucose tolerance (FIG. 14) and insulin tolerance (FIG. 15) tests. These data suggest that the compound led to enhanced insulin signaling in the high fat diet-fed mice. In order to examine this further, the effect of the compound on tyrosine phosphorylation of the insulin receptor β subunit and activation of downstream signaling, through phosphorylation of AKT in the liver, were measured. A marked increase in β-subunit phosphorylation following administration of the compound either orally or intraperitoneally was observed, which was not observed with saline. FIG. 16. Consistent with this, we enhanced AKT phosphorylation was observed following DPM-1001 treatment, indicating improved insulin signaling in response to the compound.

Considering also the important role of leptin in the control of glucose homeostasis and obesity, the effects of the compound on leptin signaling in the hypothalamus was tested. Similar to the improvement in insulin signaling, treatment with DPM-1001, but not saline, led to enhanced phosphorylation of JAK2, consistent with enhanced leptin signaling. FIG. 17.

Compound of Formula I Binds Copper and Ameliorated Deficits in a Mouse Model of Wilsons Disease Methods ESI-MS Analysis of DPM-1001-Copper Complex Eight equivalents of $M(NO_3)_2 \cdot xH_2O$ or $MSO_4 \cdot xH_2O$ were reacted with 1 eq. of DPM-1001, DPM-1003 or analog 2 (1 mM in $H_2O$). The reaction solutions were stirred at RT, 40° C. and 80° C. for 2 h. Each sample was diluted 5-fold in 50% methanol, 0.1% formic acid and loaded into a 500 µL syringe. A Thermo Vantage triple quadrupole mass spectrometer (Thermo Scientific), equipped with an HESI spray source was coupled to an Accela HPLC system (Thermo Scientific). Mobile phase A consisted of 0.1% formic acid and mobile phase B consisted of 0.1% formic acid in methanol. Isocratic flow was set to 50% B at 200 µL/min. 200 µl samples were injected into the LC flow line via syringe pump at 10 µL/min and electrosprayed into the Vantage triple quadrupole mass spectrometer. A spray voltage of 4.3 kV was used along with a capillary temperature of 350° C. Each full MS scan was 0.5 s and data were collected with a scan range of 200 m/z to 900 m/z over 1 min.

Copper-Binding Assays

Direct binding assays were performed using radiolabelled copper (64 $Cu^{2+}$). Varying concentrations of radiolabeled copper was incubated with DPM-1001 (100 nM). Excess copper was removed by running the samples through a C18 column. The amount of metal bound to the compound was quantitated directly by scintillation counting. For assays with the protein, His-tagged PTP1B (100 nM) was incubated with varying concentrations of Cu-DPM-1001 complex for 60 min in assay buffer (50 mM Hepes, 100 mM NaCl, 0.1% BSA pH 6.5) at 25° C. Protein-bound and free compound were separated by incubating the protein-inhibitor mixture with 50 µl of 50% Ni-NTA beads for 10 min at 25° C. The beads were washed with assay buffer containing 150 mM NaCl and 25 mM Imidazole three times by centrifuging the samples at 5000×g for 10 minutes. The inhibitor bound to protein was determined by scintillation counting. The amount of bead-bound protein was estimated by BCA protein quantification. For protein quantitation the bead bound protein was precipitated with TCA (25% final) on ice for 30 minutes. The precipitant was solubilized in 200 µl of 8M Urea and the protein concentration was estimated using BCA protein quantification method.

Cell Culture

HepG2 cells purchased from ATCC were cultured in RPMI media containing 10% FBS, 5% $CO_2$ at 37 C. Control (AG09319) and Wilson's disease patient-derived fibroblasts (GM00032, GM00033, GM05257, GM12158, GM05798 and GM11778) were obtained from Coriell Biorepository and cultured in DMEM, 10% FBS, 5% $CO_2$ at 37° C.

Cell Based Assays

For cell survival assays, 10,000 cells were seeded in a 96 well plate and cultured until fully confluent (90%). To these cells, ATP7B siRNAs or scrambled siRNA (negative control) purchased from Qiagen and Santa Cruz Biotechnology were transfected. Lipofectamine RNAiMAX reagent (Thermofischer) and siRNAs were diluted into a final volume of 100 µl in Opti-MEM (Gibco). The mixture was incubated at room temperature for 30 min, following which 800 µl of Opti-MEM was added to the mixture. The above transfection solution was overlaid onto cells at a final concentration of 5 nM siRNA. Transfection of HepG2 cells with scrambled siRNA served as negative control. Twelve hours after the transfection, complete media was added to each well. Following which, knockdown efficiency was checked (24 hours later) and cells were exposed to varying concentration of copper (0-1 mM) for 12 h and cell viability was determined using the MTT assay as previously described (37). To test the ability of DPM-1001 to prevent copper-induced toxicity, cells were preincubated with the compound at 2 µM for an hour prior to exposing cells to copper.

Animal Experiments.

C3He-Atp7b$^{tx-j}$ were obtained from the Jackson laboratory. All animal experiments were performed according to protocols approved by the Institutional Animal Use and Care Committee of Cold Spring Harbor laboratory. Mice were injected intraperitoneally (i.p.) with vehicle, or administered DPM-1001 intraperitoneally or orally at 5 mg/kg once every third day, for over a year. At the end of the study animals were euthanized and tissue samples were removed for biochemical studies.

Inductively Coupled Plasma Mass Spectrometry.

Tissue samples from wild-type or TX mice treated with saline, DPM-1001 or tetrathiomolybdate was washed three times with PBS containing 1 mM EDTA (to remove non-specifically bound copper). Then, 215 µl of concentrated nitric acid (BDH Aristar Ultra) was added to each sample and incubated overnight. Samples were boiled at 95° C. for 1 h. and approximately 150 µl of each sample was further diluted in 2 ml 2% nitric acid (made freshly from concentrated nitric acid and Milli-Q water) Samples were analyzed on a Thermo Fisher iCAP Qc ICP mass spectrometer in kinetic energy discrimination (KED) mode against a calibration curve of known copper and phosphorus concentrations, with Ga (20 µg/l, Inorganic Ventures) as an internal standard, Each experiment was carried out twice and each condition was repeated in at least triplicate.

Metallothionein Quantitation

Tissue samples (100 mg liver or 25 mg brain) were rinsed in PBS to remove excess blood and homogenized using a dounce homogenizer on ice (PBS, 1% tween). The samples were centrifuged at 5000×g for 5 minutes and the supernatant was collected. Total protein in the supernatant was measured using Bradford reagent and an equal amount of each sample (based on protein concentration) was used to measure metallothionein levels. Mouse metallothionein Elisa kit was purchased from Lifespan Biosciences, Inc and the assay was performed according to the users manual.

Histology

Liver tissues from wild-type and TX mice from untreated and DPM-1001-treated mice were sectioned and stained with H&E or rhodanine. Whole-slide, digitized images of H&E-stained tissue were captured using the Aperio ScanScope XT automated scanning system (Vista, CA). Image J software was used to quantitate rhodanine staining.

Results

DPM-1001 is a Specific Copper Chelator

To examine chelation of copper by DPM-1001, whether DPM-1001 displayed specificity for copper was tested by incubating the compound with a series of metal ions, then subjecting the complexes to ESI-MS analysis. The ESI-MS spectra of the compound in the presence of $CuSO_4$ revealed three peaks, at 568.6, 620 and 727.5 m/z. The peak at 568.6 corresponded to free compound, whereas the peaks at 620 and 727.5 corresponded to the Cu- and $CuSO_4$-bound forms, respectively. FIG. 18. When incubated DPM-1001 was incubated with a variety of other metals, none formed a complex with the compound. FIG. 18. This includes silver, which is isoelectronic and similar in size to $Cu^+$, highlighting the exquisite specificity of DPM-1001 for copper.

Using radiolabelled copper ($^{64}Cu$), and titrating DPM-1001 against increasing concentration of $^{64}Cu$ in a binding assay, a $K_d$ of 75 nM was measured. To investigate the mechanism by which DPM-1001 chelated copper, a series of analogs were generated. Removal of the $N^1$-(pyridin-2-ylmethyl)butane-1,4-diamine tail from the 3 position of the A ring in the cholesterol group was sufficient to abrogate copper binding, focusing attention on the importance of this tail. Substitution of the pyridyl group with either piperidine or benzene, or generating a 4-amino substituent with an ether, to produce 4-(pyridin-2-ylmethoxy)butan-1-amine, also impaired binding. Within the pyridyl group, the N-atom was moved from the 2-position in DPM-1001 to the 3-position, to generate compound DPM-1003. Interestingly, despite their identical chemical composition, DPM-1003, in contrast to DPM-1001, displayed limited binding to radiolabelled $^{64}Cu$ and to any of the metals tested.

In addition, $N^1,N^4$-bis(pyridin-2-ylmethyl)butane-1,4-diamine was generated (Analog 2), which is a symmetrical compound in which the steroid moiety seen in DPM-1001 was replaced by a second pyridine ring. When incubated in the presence of $CuSO_4$, this analog yielded a distinct peak at 332 on ESI-MS analysis that corresponded to the Cu(II)-bound form of the compound. When titrated against $^{64}Cu$, a Kd of 57 nM was obtained. In addition, when we incubated Analog 2 against the panel of metals, in contrast to DPM-1001, this analog bound to all the metals tested. Overall, these data illustrate that within DPM-1001 the $N^1$-(pyridin-2-ylmethyl)butane-1,4-diamine tail was responsible for copper chelation, whereas the steroid moiety conferred selectivity in copper binding.

DPM-1001 Improved Viability of Cells Exposed to High Copper

As DPM-1001 was a potent copper chelator in vitro, its ability to bind copper in a cellular context was tested. HepG2 cells were used as a model, including cells in which ATP7B, a P-type Cu-ATPase that functions in copper excretion, was suppressed. Unlike wild-type cells, ATP7B-knockdown cells were observed to be sensitive to exposure to copper. At copper concentrations greater than 0.5 mM, the survival of ATP7B-KD1 was less than 20% (FIG. 19), highlighting the importance of ATP7B in protecting cells from the effects of excess copper. When viability was tested in the presence of DPM-1001 (2 µM), the compound was able to rescue cells from copper-induced cell death (FIG. 19).

The significance of this observation was explored further by testing a panel of six different skin fibroblasts derived from Wilson's disease patients. These cells have been reported to express different mutant forms of ATP7B and to display elevated levels of free copper relative to normal fibroblasts. The survival of these cells in the presence of increasing concentrations of copper was measured and compared to the response to that observed in normal skin fibroblasts. Although a varying response to copper in the mutant cells was observed, all were found to be more sensitive to copper-induced cell death than the wild-type cells. Interestingly, DPM-1001 also inhibited copper-induced cell death in the fibroblasts derived from Wilson's disease patients. FIGS. 20-22, 26-28.

DPM-1001 Lowered Copper Levels in an Animal Model of Wilson's Disease.

The TX mouse is a naturally occurring genetic and phenotypic model of Wilson's disease. A Gly to Asp substitution (G775D) renders the ATP7B protein dysfunctional and results in copper accumulation. This has been used widely as a model to understand the human disease. TX and wild-type mice exhibit different longevities. Survival in TX and wild-type mice treated with DPM-1001 or saline was therefore assessed. Wild-type mice treated with saline or DPM-1001 survived until the end of the study, with 100% survival at one year of age. In contrast, only 60% of saline-treated TX mice survived at one year of age. Interestingly, 90% of DPM-1001 treated TX mice survived at one year of age. FIG. 29. Prolonged treatment with DPM-1001 did not have overt toxic side-effects in either wild-type or TX mice.

Tissue copper levels were assessed by two separate methods. Liver tissue was excised from wild-type and TX mice that had been treated with saline or DPM-1001, then fixed and stained with rhodanine, a dye that stains for copper-binding proteins. No signal was detected in liver samples obtained from saline- or DPM-1001-treated wild-type mice. In saline-treated TX mice, bright staining with the dye was observed, indicative of elevated copper levels. In contrast, no obvious staining for rhodanine was observed in liver samples obtained from DPM-1001 treated mice. FIG. 23. ICP-MS was used to obtain a quantitative measure of copper levels. Elevated levels of copper in liver of saline-treated TX mice were observed compared to control animals, and treatment with DPM-1001 lowered the levels of copper in both tissues. FIG. 24. Interestingly, the 3-pyridyl analog, DPM-1003, which has the same chemical composition as DPM-1001 but does not chelate copper, did not suppress the levels of the metal in liver of TX mice, suggesting that the effects of DPM-1001 on tissue copper levels were direct. FIG. 30. Effect of DPM-1001 were then compared with the drug candidate chelator, tetrathiomolybdate (TTM), and that DPM-1001 was as effective as tetrathiomolybdate in removing copper from the liver and brain, but at both a lower dose and lower frequency of administration. FIG. 24

The mechanism by which DPM-1001 cleared tissue copper levels was also investigated. Penicillamine as "decoppering" agents promotes excretion of the metal in the urine. Therefore, copper levels in kidney samples obtained from saline-treated or DPM-1001-treated, wild-type and TX mice were measured and no significant differences were observed. In contrast, treatment with tetrathiomolybdate resulted in dramatically elevated copper levels in the kidney. FIG. 24. Fecal material were collected from the mice and copper levels thereof analyzed. In contrast to TX mice treated with saline, the levels of copper in the feces of DPM-1001-treated TX mice were dramatically elevated. Unlike DPM-1001 treatment, treatment with tetrathiomolybdate resulted in only a small increase in levels of fecal copper. FIG. 24.

DPM-1001 Ameliorated Hepatic Complications Associated with WD

In light of the fact that liver damage and hepatic complications are among the hallmarks of Wilson's disease, morphological analyses of the liver obtained from wild-type and TX mice, following treatment with saline or DPM-1001, were conducted. In wild-type liver, treated with saline or DPM-1001, then sectioned and stained for morphological analysis, no obvious abnormalities were detected; normal hepatocyte size, shape and arrangement was observed. In contrast, liver sections obtained from TX mice treated with saline revealed enlarged hepatocytes with irregular shape and arrangement, as well as large cytoplasmic lipid droplets. Interestingly, liver sections obtained from TX mice treated with DPM-1001, appeared similar to those from wild-type mice with normal hepatocyte size, shape and arrangement. Furthermore, no large lipid droplets were observed, in contrast to liver sections from saline-treated TX mice.

In addition, metallothionein levels were measured in the liver and brain. Metallothionein levels were significantly elevated in both tissues in TX mice, compared to wild-type. Furthermore, DPM-1001 treatment lowered metallothionein levels in the liver and the brain. FIG. 25. The data demonstrated that DPM-1001 lowered tissue copper levels and ameliorated symptoms associated with Wilson's disease.

Anticancer Effects of a Compound of Formula I and Inhibition of Kinase Activity

Methods

Cell Proliferation Assay

The MTT assay was used to evaluate cell survival in the absence and presence of different compounds. The thiazolyl blue tetrazolium bromide (MTT) was dissolved in phosphate buffered saline (PBS) at a concentration of 5 mg/ml, filtered, and stored at 4° C. About 10,000 cells were seeded into a 96-well plate and cultured in growth medium containing serum. After 24 hours, cells were treated with the indicated concentrations of DPM-1001 or DPM-1003 (0-100 uM) for 2 hrs. Following which 20 µl MTT was added into each well. An ELISA plate reader (Biotek, Winooski, Vermont, USA) was used to measure the optical density at 490 nm.

Crystal Violet Staining

MDA-MB-231 cells ($1\times10^5$) were seeded in 6 cm plates in growth medium. The cells were untreated or treated with DPM-1001 (0.5, 1, 2 and 5 µM), DPM-1003 (0.5, 1, 2 and 5 µM) or TTM (25, 50, 100 µM) for 1 h. Following which, media was gently aspirated and cells were washed with PBS. To each plate 0.5 ml of crystal violet (0.5%) was added and incubated in dark for 10 minutes at room temperature. The staining solution was removed and plates were washed with PBS (three times). The cells stained with the dye were imaged.

Annexin V and Propidium Iodide (PI) Staining

Cells ($1\times10^5$) were plated in six-well plates in growth medium. The cells were untreated or treated with DPM-1001 (2 µM). Following which, cells were washed with cold PBS twice and resuspended in 0.1 M Hepes/NaOH (pH 7.4), 1.4 M NaCl, 25 mM CaCl2). To the cell suspension 5 µl of fluorescein isothiocynate (FITC)-conjugated annexin V (0.1 mg/ml) and propidium iodide (1 mg/ml) were added and the samples were incubated in dark for 30 minutes at room temperature. The samples were analyzed by flow cytometry (Becton Dickinson LSRII Cell Analyzer).

Inductively Coupled Plasma Mass Spectrometry

TNBC cells ($1\times10^6$) were plated in a 10-cm culture dish in growth medium. About 24 h after seeding cells, they were untreated or treated with DPM-1001 (2 uM) or DPM-1003 (2 uM) for 2 h. Following which, cells were washed three times with PBS. Then, 215 µl of concentrated nitric acid (BDH Aristar Ultra) was added to each sample and incubated overnight. Samples were boiled at 95° C. for 1 h. and approximately 150 µl of each sample was further diluted in 2 ml 2% nitric acid (made freshly from concentrated nitric acid and Milli-Q water). Samples were analyzed on a Thermo Fisher iCAP Qc ICP mass spectrometer in kinetic energy discrimination (KED) mode against a calibration curve of known copper and phosphorus concentrations, with Ga (20 µg/l, Inorganic Ventures) as an internal standard. Each experiment was carried out twice and each condition was repeated in at least triplicate.

CTR1 siRNA Transfection

Four distinct small interfering RNAs (siRNAs) were used to target human CTR1 transcripts. Individual siRNAs were reconstituted in nuclease-free water to achieve a 10 µM solution. The siRNAs were transfected using siRNA-Oligofectamine (Invitrogen), when cells were about 70% confluent. The Ctrl_AllStars_1 siRNA was reconstituted to 10 µM and used as negative control. Briefly, 7500 cells were seeded in a 96 well plate in complete growth media. About 24 h after seeding cells, oligofectamine (0.5%) and siRNA (50 nM) were incubated in 200 µl of serum free media at room temperature for 15 minutes and 100 µl of the siRNA-oligofectamine complex was added per well. After incubation at 37° C. in 5% $CO_2$ for 6 h, media was removed from the cells and replaced with regular growth media. Cell density was measured in the absence and presence of DPM-1001 (2 µM) by MTT assay every 12 hours.

Identification of Kinases Regulated by Copper

Triple-negative breast cancer (TNBC) cells ($1\times10^6$) were plated in a 10-cm culture dish in growth medium. About 24 h after seeding, cells were washed twice using cold PBS. After which, cells were resuspended in 100 µl of 50 mM HEPES, pH 6.5, 100 mM NaCl, 0.05% Tween-20 and lysed on ice by sonication (15 s pulse-on and 45 s pulse-off (2 cycles)). Total lysate was centrifuged at 3000×g for 10 minutes and supernatant was collected and quantitated using bradford protein quantitation assay. About 1 mg of the lysate was incubated with biotinylated ATP-probe (Pierce) for 90 minutes at 4 C with constant shaking. To the reaction 50 μl (50% slurry) of streptavidin beads were added and incubated for 30 minutes at 4 C. Beads were centrifuged and washed (50 mM HEPES, pH 6.5, 100 mM NaCl, 0.05% Tween-20) three times. Kinase bound to the beads were eluted using 250 mM phosphate solution. This was further incubated with Cu-pentadentate resin (Affiland) for 90 minutes at 4 C. The resin was centrifuged and washed using 50 mM HEPES, pH 6.5, 100 mM NaCl, 25 mM Imidazole twice. Protein bound to the resin was analyzed by mass spectrometry.

Kinase Activity Assay

In brief, recombinant PAK1 (20 nM) or recombinant MEK1 (20 nM) were incubated for 30 min in 180 μl of kinase buffer in the presence or absence of $CuSO_4$ (5 μM). The activity of the kinase was monitored using MBP as substrate by ADP-Glow assay (Promega) as per user's manual.

Cu-Binding Assay

Direct binding assays were performed using radiolabelled copper (64 $Cu^{2+}$). Varying concentration of radiolabeled copper (0-10 uM) was incubated with recombinant PAK1 (100 nM). Excess copper was removed by running the samples through a desalting column. The amount of metal bound to the protein was quantitated directly by scintillation counting.

Xenograft Studies

MDA-MB-231 cells ($2 \times 10^6$) were injected orthotopically into mammary fat pads of SCID-beige mice (Tectonic lab) in 15 μl of a 1:1 mixture with DMEM and growth factor-reduced Matrigel (BD Biosciences). The animals were randomly assigned to three groups to receive saline (control), DPM-1001 (5 mg/kg) or DPM-1003 (5 mg/kg) intraperitoneally everyday once the tumors reached about 200 $mm^3$. Tumor growth was monitored every third day and volume in $mm^3$ was measured three times weekly by palpation using the formula: volume=$width^2 \times length/2$. Once the tumor volume reached above 500 $mm^3$ in saline treated mice, the study was terminated. Tumors from all mice were removed for biochemical analysis.

Immunoblotting

Equal quantities of lysates were isolated from indicated cell lines and then resolved by SDS-PAGE and immunoblotted with one of the following primary antibodies: mouse anti-MEK1/2, rabbit anti-p-PAK1, rabbit anti-PAK1, rabbit anti-ERK1/2, rabbit anti-phospho(Ser 217/221)-MEK1/2, rabbit anti-phospho(Thr 202/Tyr 204)-ERK1/2, rabbit anti-phospho (Ser 338)-c-RAF, rabbit anti-RAF, rabbit anti-phospho (Ser 112)-BAD and rabbit anti-BAD (Cell Signaling Technology), mouse anti-β-actin (Sigma), followed by detection with one of the following horseradish peroxidase-conjugated secondary antibodies: goat anti-rabbit IgG, goat anti-mouse IgG (Invitrogen), mouse anti-rabbit light-chain-specific IgG (Jackson ImmunoResearch Laboratories) using enhanced chemiluminescence (ECL; GE Healthcare) or SuperSignal West Femto Chemiluminescent substrate (Pierce) detection reagents.

Results

As shown in FIGS. 31-39, DPM-1001 inhibited survival of many different breast cancer cell lines that do not express HER2, estrogen receptors, or progesterone receptors (known to those skilled in the relevant field as triple-negative breast cancer, TNBC) at doses at which DPM-1003 did not affect survival of these cancer cell lines. In contrast, effects of DPM-1001 and DPM-1003 on survival of several non-TNBC cell lines did not differ from each other. FIGS. 40-42 and FIG. 46.

As shown in FIG. 43, treatment of numerous cancer cell lines, including TNBC cell lines, depleted cellular copper levels, as assessed by inductively coupled plasma mass spectrometry.

As shown in FIGS. 44 and 45, DPM-1001 reduced tumor volume in mice receiving transplanted TNBC cells, whereas a comparable dose of DPM-1003 was without effect. Effects of DPM-1001 on inhibiting survival of the TNBC cell line MDA-MB-231 is also shown in FIG. 46. Annexin V and propidium iodide staining confirmed that the reduction of cell survival of TNBC cells by DPM-1001 was due to promoting death of these cells.

Treatment of TNBC cell lines MDA-MB-231 and SUM159 also caused a reduction in levels of phospho-Erk, indicating inhibition of MEK/ERK signalling. Other copper chelators also had this effect, though at substantially higher doses than required for DPM-1001. For example, high levels of reduction of phsopho-Erk were achieven with 1-2 μM of DPM-1001, and this inhibition was greater than that seen with 50 μM of bathocuproine disulfonate or 25 μM of TTM.

Survival of TNBC cells in response to DPM-1001 treatment was also tested in TNBC cells that are and are not sensitive to effects of the MEK inhibitor AZD6244 on cell survival. In several cell lines (MDA-MB-231, MCF-7, and SUM159), treatment with AZD6244 inhibited cell survival, whereas AZD6244 was without effect on survival of several other cells (HCC70, MDA-MB-468, and SUM149). In the AZD6244-sensitive cells, 1-2 μM AZD6244 reduced phospho-MEK and phospho-Erk but was without effect in the AZD6244-insensitive cells. Furthermore, as shown in FIGS. 47-49, treatment of the AZD6244-resistant cells with AZD6244 in combination with DPM-1001 inhibited cell survival. Such combined treatment also reduced phospho-MEK and phospho-Erk levels in these cells.

Analysis of copper binding proteins from several TNBC cell lines, including MDA-MB-231, CAL-120, SUM-159, HCC-70, SUM-149, and HS578T cells, identified numerous copper-binding proteins, including pyruvate kinase M (PKM), mitochondrial adenylate kinase 2 (AK2), creatine kinase B (CKB), p21-activated kinase (PAK), TP53-regulating kinase (TP53RK), phosphoglycerate kinase 1 (PGK1), pyridoxal kinase (PDXK), mitochondrial creatine kinase U-type (CKMT1B), mitogen-activated protein kinase kinase (MEK), tyrosine kinase CSK. Binding to copper was further confirmed for MEK1 and PAK1 in a copper binding assay (Kd=5 nM and 15 nM, respectively) and PAK1 kinase activity was higher in the presence of copper ($V_{max}$ and $K_m$ in the absence of Cu(II)=361.8 and 36.21, respectively, and in the presence of Cu(II) were 834.4 and 35.08, respectively). Adding copper to culture media also increased levels of phospho-PAK1 in TNBC cells, and effect blocked by co-administration with DPM-1001.

CTR1 expression was also upregulated in TNBC cells. Furthermore, addition of 5-10 μM copper to cell culture media lead to increased pS338-RAF1 and pS112-BAD levels in several TNBC lines, effects reduced or blocked by co-administration of DPM-1001. These results indicate that copper may enhance cell survival of TNBC cells, such as through activation of PAK, MEK, and cell-survival-promoting signaling pathways, and that a compound of Formula I, such as DPM-1001, can promote TNBC cell death, such as by blocking copper-induced stimulation of such signaling pathways and functions.

An inhibitory effect of DPM-1001 on cell survival was not limited to TNBC cancer cells. DPM-1001 also inhibited survival of several gastric cancer cell lines, including SNU116, KATOIII, SNU5, AGS, SNU1, and N87 cells. FIGS. 50-55. In comparison, DPM-1001 had no effect on survival of NIH 3T3 cells, indicating that DPM-1001 is not a general or universal cytotoxin.

Binding of compounds of Formula I other than DPM-1001 was also confirmed. In an ESI-MS test, compound DPM-1013 as hydrochloride salt was dissolved in distilled water at a concentration of 2 mM freshly before testing. It was then mixed with an equal volume copper sulfate (16 mM) or copper chloride solution (16 mM) for 2 h, rendering a concentration of DPM-1013 at 1 mM and the copper salt 8 mM. The mixture was then further diluted 100-fold before injection into an ESI-MS, making a final concentration of DPM-1013 of 10 μM and Cu 80 μM in the test.

Mixed with $CuSO_4$, DPM-1013 formed complexes with free Cu, $CuSO_4$, and other adducts such as $CuCl_2$ (Cl from DPM-1013 chloride salt) and $Cu(OH)_2$, shown as the peaks in FIG. 56A. The binding percentage at this concentration rate (DPM-1013: Cu=1:8) was calculated as:

Binding percentage=peak intensity of all DPM-1013-Cu complex/(peak intensity of all DPM-1013-Cu complex+ peak intensity of free DPM-1013).

Mixed with $CuCl_2$, DPM-1013 formed complexes with free Cu, $CuCl_2$ and other adducts such as Cu(OH)2, shown as the peaks FIG. 56B. The binding percentage at this concentration rate (DPM-1013: Cu=1:8) was calculated in the same manner as $CuSO_4$.

Data from FIGS. 56A and 56B can be summarized according to the following Table 1:

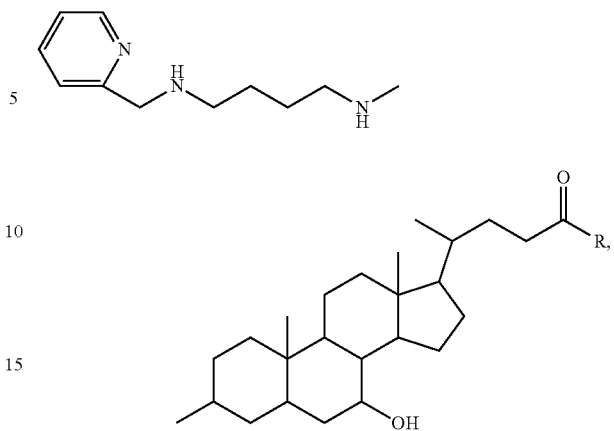

wherein R is —OH or —O—$CH_3$.

TABLE I

Copper binding of DPM-1013

| Peak Intensity | Compound | Compound + Metal | Compound + Metal + Salt | Compound + Metal + other | Compound + Metal + other | Percentage |
|---|---|---|---|---|---|---|
| 1013 – $CuSO_4$ | 2.80E+06 | 1.73E+06 | 6.78E+06 | 3.12E+06 | 1.33E+06 | 82.23% |
| 1013 – $CuCl_2$ | 5.34E+06 | 7.24E+05 | 6.69E+06 | 8.02E+06 | | 74.29% |

Figure 8B:
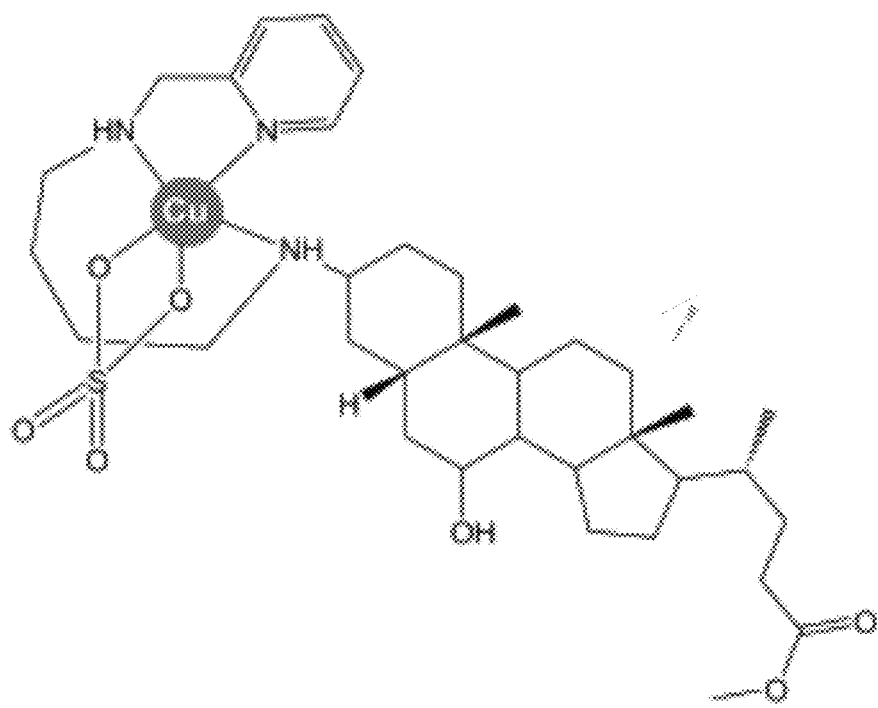

Without being limited to any particular binding mechanism or structure, DPM-1013, like DPM-1001 (see FIG. 8A), may act as a tridentate ligand forming one seven-membered and one five-membered chelate ring, while the environment around the Cu (II) is most likely to be five-coordinate displaying either a square pyramidal or a trigonal bipyramidal geometry (FIG. 8B). Square planar geometry, although rather typical for Cu (II), is not favored in this case due to the nature of the DPM-1013 ligand, whereas tetrahedral geometry is quite rare (the structure normally goes through solvent/counteranion coordination or ligand rearrangement affording thermodynamically more stable compounds with higher coordination numbers).

The invention claimed is:

1. A method of treating cancer in a subject in need of such treatment, wherein the cancer is a triple negative breast cancer and the method comprises administering to the subject a compound of Formula I:

2. The method of claim 1, further comprising administering to said subject AZD6244.

3. The method of claim 1, wherein the subject was previously-administered AZD6244 before the administering of the compound of Formula I.

4. A method of administering to a subject a pharmaceutical composition comprising copper complexed with a compound of Formula I:

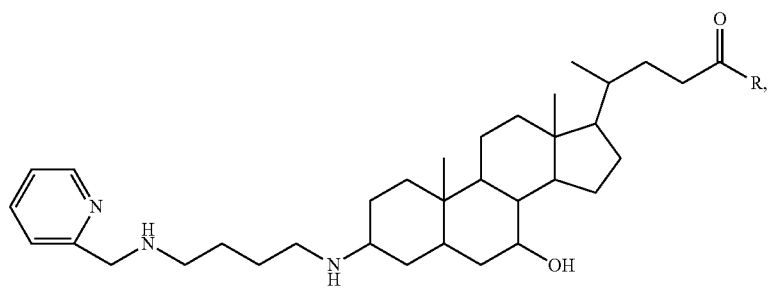

wherein R is —OH or —O—$CH_3$, the subject has cancer and the cancer is gastric cancer or HER2-negative breast cancer, and administering the pharmaceutical composition comprises inhibiting tumor growth, inhibiting cancer cell metastasis, stimulating cancer cell death, or any combination of two or more of the foregoing.

5. The method of claim 4 wherein the cancer is HER2-negative breast cancer wherein the HER2-negative breast cancer is estrogen-receptor negative, progesterone-receptor negative, or triple-negative breast cancer.

6. The method of claim 5, wherein the cancer is triple-negative breast cancer.

7. The method of claim 4, further comprising administering to said subject AZD6244.

8. The method of claim 4, wherein the subject was administered AZD6244, before the administering of the pharmaceutical composition.

* * * * *

UNITED STATES PATENT AND TRADEMARK OFFICE
CERTIFICATE OF CORRECTION

| | | |
|---|---|---|
| PATENT NO. | : 12,178,825 B2 | Page 1 of 1 |
| APPLICATION NO. | : 17/866724 | |
| DATED | : December 31, 2024 | |
| INVENTOR(S) | : Tonks et al. | |

It is certified that error appears in the above-identified patent and that said Letters Patent is hereby corrected as shown below:

In the Claims

Column 60, Line 36: Claim 3, Delete "previously"

Signed and Sealed this
Fourth Day of February, 2025

Coke Morgan Stewart
*Acting Director of the United States Patent and Trademark Office*